(12) United States Patent
Alshaiba Saleh Ghannam Almazrouei et al.

(10) Patent No.: US 12,201,144 B2
(45) Date of Patent: *Jan. 21, 2025

(54) HOOKAH DEVICE

(71) Applicant: SHAHEEN INNOVATIONS HOLDING LIMITED, Abu Dhabi (AE)

(72) Inventors: Mohammed Alshaiba Saleh Ghannam Almazrouei, Abu Dhabi (AE); Sajid Bhatti, Abu Dhabi (AE); Jeff Machovec, Abu Dhabi (AE); Clement Lamoureux, Abu Dhabi (AE); Imad Lahoud, Abu Dhabi (AE)

(73) Assignee: Shaheen Innovations Holding Limited, Abu Dhabi (AE)

( * ) Notice: Subject to any disclaimer, the term of this patent is extended or adjusted under 35 U.S.C. 154(b) by 0 days.

This patent is subject to a terminal disclaimer.

(21) Appl. No.: 17/835,923

(22) Filed: Jun. 8, 2022

(65) Prior Publication Data

US 2022/0361565 A1 Nov. 17, 2022
US 2024/0148053 A9 May 9, 2024

Related U.S. Application Data

(63) Continuation of application No. 17/300,931, filed on Dec. 15, 2021, now Pat. No. 11,730,191, which is a
(Continued)

(30) Foreign Application Priority Data

Apr. 6, 2020 (EP) .................................... 20168231
Apr. 6, 2020 (EP) .................................... 20168245
Apr. 9, 2020 (EP) .................................... 20168938

(51) Int. Cl.
*A24F 1/30* (2006.01)
*A24F 40/05* (2020.01)
(Continued)

(52) U.S. Cl.
CPC ................ *A24F 1/30* (2013.01); *A24F 40/05* (2020.01); *A24F 40/10* (2020.01); *A24F 40/42* (2020.01);
(Continued)

(58) Field of Classification Search
None
See application file for complete search history.

(56) References Cited

U.S. PATENT DOCUMENTS 4,119,096 A 10/1978 Drews
4,334,531 A 6/1982 Reichl
(Continued)

FOREIGN PATENT DOCUMENTS

CN 2648836 Y 10/2004
CN 101648041 A 2/2010
(Continued)

OTHER PUBLICATIONS

Liu Xiaosen et al: "An Automatic Resonance Tracking Scheme With Maximum Power Transfer for Piezoelectric Transducers", IEEE Transactions on Industrial Electronics, IEEE Service Center Piscataway, NJ, USA, vol. 62, No. 11, Nov. 1, 2015, pp. 7136-7145, XP011586142, ISSN: 0278-0046, DOI: 10.1109/TIE.2015.2436874.

(Continued)

*Primary Examiner* — Katherine A Will

(74) *Attorney, Agent, or Firm* — Amedeo F. Ferraro, Esq.

(57) ABSTRACT

A hookah device (202) which attaches to a hookah (246). The hookah device (202) comprises a plurality of ultrasonic mist generator devices (201) for generating a mist for inhalation by a user. The hookah device (202) comprises a driver device (202) which controls the mist generator devices (201) to maximize the efficiency of mist generation (Continued)

by the mist generator devices (201) and optimize mist output from the hookah device (202).

24 Claims, 48 Drawing Sheets

Related U.S. Application Data continuation-in-part of application No. 17/223,846, filed on Apr. 6, 2021, now Pat. No. 11,730,193, which is a continuation-in-part of application No. 16/889,667, filed on Jun. 1, 2020, now Pat. No. 11,254,979, and a continuation-in-part of application No. 17/065,992, filed on Oct. 8, 2020, now abandoned, said application No. 17/223,846 is a continuation-in-part of application No. 17/122,025, filed on Dec. 15, 2020, now Pat. No. 11,672,928, which is a continuation-in-part of application No. PCT/IB2019/060808, filed on Dec. 15, 2019, and a continuation-in-part of application No. PCT/IB2019/060810, filed on Dec. 15, 2019, and a continuation-in-part of application No. PCT/IB2019/060811, filed on Dec. 15, 2019, and a continuation-in-part of application No. PCT/IB2019/060812, filed on Dec. 15, 2019, said application No. 17/223,846 is a continuation-in-part of application No. 17/220,189, filed on Apr. 1, 2021, said application No. 17/300,931 is a continuation-in-part of application No. 17/122,025, filed on Dec. 15, 2020, now Pat. No. 11,672,928, said application No. 17/300,931 is a continuation-in-part of application No. 17/220,189, filed on Apr. 1, 2021.

(60) Provisional application No. 63/064,386, filed on Aug. 11, 2020.

(51) Int. Cl.
| | |
|---|---|
| *A24F 40/10* | (2020.01) |
| *A24F 40/42* | (2020.01) |
| *A24F 40/44* | (2020.01) |
| *A24F 40/48* | (2020.01) |
| *A24F 40/51* | (2020.01) |
| *A24F 40/53* | (2020.01) |
| *A61M 11/00* | (2006.01) |
| *B05B 17/06* | (2006.01) |
| *B06B 1/06* | (2006.01) |
| *H02J 7/00* | (2006.01) |
| *H03L 7/081* | (2006.01) |
| *H03M 1/12* | (2006.01) |

(52) U.S. Cl.
CPC ............. *A24F 40/44* (2020.01); *A24F 40/48* (2020.01); *A24F 40/51* (2020.01); *A24F 40/53* (2020.01); *A61M 11/005* (2013.01); *B05B 17/0653* (2013.01); *B05B 17/0669* (2013.01); *B05B 17/0684* (2013.01); *A61M 2205/3368* (2013.01); *A61M 2205/3576* (2013.01); *A61M 2205/52* (2013.01); *B06B 1/06* (2013.01); *H02J 7/0042* (2013.01); *H03L 7/081* (2013.01); *H03M 1/124* (2013.01)

(56) References Cited

U.S. PATENT DOCUMENTS

| | | |
|---|---|---|
| 5,355,873 A | 10/1994 | Del Bon |
| 5,518,179 A | 5/1996 | Humberstone et al. |
| 5,551,416 A | 9/1996 | Stimpson |
| 5,894,841 A | 4/1999 | Voges |
| 5,950,619 A | 9/1999 | van der Linden |
| 6,011,345 A | 1/2000 | Murray |
| 6,040,560 A | 3/2000 | Fleischhauer |
| 6,402,046 B1 | 6/2002 | Loeser |
| 6,601,581 B1 | 8/2003 | Babaev |
| 6,679,436 B1 | 1/2004 | Onishi |
| 7,129,619 B2 | 10/2006 | Yang |
| 8,991,722 B2 | 3/2015 | Friend |
| 9,242,263 B1 | 1/2016 | Copeman |
| 9,278,365 B2 | 3/2016 | Banco |
| 9,415,412 B2 | 8/2016 | Kawashima |
| 9,687,029 B2 | 6/2017 | Liu |
| 9,687,627 B2 | 6/2017 | Gallem |
| 9,718,078 B1 | 8/2017 | Chau |
| 9,867,398 B2 | 1/2018 | Guo |
| 9,980,140 B1 | 5/2018 | Spencer |
| 10,034,495 B2 | 7/2018 | Alarcon |
| 10,071,391 B2 | 9/2018 | Yu |
| 10,195,368 B2 | 2/2019 | Wang |
| 10,300,225 B2 | 5/2019 | Terry |
| 10,327,479 B2 | 6/2019 | Popplewell |
| 10,328,218 B2 | 6/2019 | Reed |
| 10,412,996 B2 | 9/2019 | Bright |
| 10,506,827 B2 | 12/2019 | Liu |
| 10,561,803 B2 | 2/2020 | Liu |
| 10,617,150 B2 | 4/2020 | Cameron |
| 10,757,971 B2 | 9/2020 | Liu |
| 11,039,641 B2 | 6/2021 | Liu |
| 11,207,711 B2 | 12/2021 | Hejazi |
| 11,219,245 B2 | 1/2022 | Liu |
| 11,278,055 B2 | 3/2022 | Liu |
| 11,304,451 B2 | 4/2022 | Hejazi |
| 11,324,253 B2 | 5/2022 | Liu |
| 11,431,242 B2 | 8/2022 | Liu |
| 11,517,685 B2 | 12/2022 | Danek |
| 11,589,609 B2 | 2/2023 | Liu |
| 11,641,876 B2 | 5/2023 | Liu |
| 11,690,963 B2 | 7/2023 | Danek |
| 11,700,881 B2 | 7/2023 | Liu |
| 11,730,896 B2 | 8/2023 | Hutchins |
| 11,744,282 B2 | 9/2023 | Liu |
| 11,744,284 B2 | 9/2023 | Liu |
| 11,771,133 B2 | 10/2023 | Lin |
| 11,771,137 B2 | 10/2023 | Liu |
| 11,796,732 B2 | 10/2023 | Novak, III |
| 11,877,600 B2 | 1/2024 | Liu |
| 11,964,301 B2 | 4/2024 | Hejazi |
| 2002/0129813 A1 | 9/2002 | Litherland |
| 2003/0192532 A1 | 10/2003 | Hopkins |
| 2003/0209005 A1 | 11/2003 | Fenn |
| 2006/0243277 A1 | 11/2006 | Denyer |
| 2006/0243820 A1 | 11/2006 | Ng |
| 2007/0125370 A1 | 6/2007 | Denyer |
| 2008/0054091 A1 | 3/2008 | Babaev |
| 2008/0088202 A1 | 4/2008 | Duru |
| 2008/0156320 A1 | 7/2008 | Low |
| 2008/0164339 A1 | 7/2008 | Duru |
| 2009/0022669 A1 | 1/2009 | Waters |
| 2009/0065600 A1 | 3/2009 | Tranchant |
| 2010/0084488 A1 | 4/2010 | Mahoney, III |
| 2010/0139652 A1 | 6/2010 | Lipp |
| 2012/0126041 A1 | 5/2012 | Mahito et al. |
| 2013/0220315 A1 | 8/2013 | Conley |
| 2014/0007864 A1 | 1/2014 | Gordon |
| 2014/0151457 A1 | 6/2014 | Wilkerson |
| 2014/0261414 A1 | 9/2014 | Weitzel |
| 2014/0270727 A1 | 9/2014 | Ampolini |
| 2015/0069146 A1 | 3/2015 | Lowy |
| 2015/0122275 A1 | 5/2015 | Wu |
| 2015/0202387 A1 | 7/2015 | Yu |
| 2015/0230522 A1 | 8/2015 | Horn |
| 2015/0231347 A1 | 8/2015 | Gumaste |
| 2015/0272214 A1 | 10/2015 | Giller |
| 2016/0001316 A1 | 1/2016 | Friend |
| 2016/0066619 A1 | 3/2016 | Di Carlo |
| 2016/0089508 A1 | 3/2016 | Smith |
| 2016/0198770 A1 | 7/2016 | Alarcon |
| 2016/0199594 A1 | 7/2016 | Finger |

(56) References Cited

U.S. PATENT DOCUMENTS

| | | |
|---|---|---|
| 2016/0206001 A1 | 7/2016 | Eng |
| 2016/0213866 A1 | 7/2016 | Tan |
| 2016/0264290 A1 | 9/2016 | Hafer |
| 2016/0324212 A1 | 11/2016 | Cameron |
| 2016/0331022 A1 | 11/2016 | Cameron |
| 2016/0338407 A1 | 11/2016 | Kerdemelidis |
| 2017/0042242 A1 | 2/2017 | Hon |
| 2017/0119052 A1 | 5/2017 | Williams |
| 2017/0119059 A1 | 5/2017 | Zuber |
| 2017/0135411 A1 | 5/2017 | Cameron |
| 2017/0136194 A1 | 5/2017 | Cameron |
| 2017/0136484 A1 | 5/2017 | Wilkerson |
| 2017/0251718 A1 | 9/2017 | Armoush |
| 2017/0265521 A1 | 9/2017 | Do |
| 2017/0281883 A1 | 10/2017 | Li |
| 2017/0303594 A1 | 10/2017 | Cameron |
| 2017/0368273 A1 | 12/2017 | Rubin |
| 2018/0042306 A1 | 2/2018 | Atkins |
| 2018/0153217 A1 | 6/2018 | Liu |
| 2018/0160737 A1 | 6/2018 | Verleur |
| 2018/0166981 A1 | 6/2018 | Leppard |
| 2018/0192702 A1 | 7/2018 | Li |
| 2018/0269867 A1 | 9/2018 | Terashima |
| 2018/0029677 A1 | 10/2018 | Terry |
| 2018/0286207 A1 | 10/2018 | Baker |
| 2018/0296777 A1 | 10/2018 | Terry |
| 2018/0296778 A1 | 10/2018 | Hacker |
| 2018/0310625 A1 | 11/2018 | Alarcon |
| 2018/0338532 A1 | 11/2018 | Verleur |
| 2018/0343926 A1 | 12/2018 | Wensley |
| 2018/0375436 A1 | 12/2018 | Wagner |
| 2019/0056131 A1 | 2/2019 | Warren |
| 2019/0098935 A1 | 4/2019 | Phan |
| 2019/0116863 A1 | 4/2019 | Dull |
| 2019/0133186 A1 | 5/2019 | Fraser |
| 2019/0158938 A1 | 5/2019 | Bowen |
| 2019/0166913 A1 | 6/2019 | Trzecieski |
| 2019/0167923 A1 | 6/2019 | Kessler |
| 2019/0216135 A1 | 7/2019 | Guo |
| 2019/0255554 A1 | 8/2019 | Selby |
| 2019/0289914 A1 | 9/2019 | Liu |
| 2019/0289915 A1 | 9/2019 | Heidl |
| 2019/0289918 A1 | 9/2019 | Hon |
| 2019/0321570 A1 | 10/2019 | Rubin |
| 2019/0329281 A1 | 10/2019 | Lin |
| 2019/0335580 A1 | 10/2019 | Lin |
| 2019/0336710 A1 | 11/2019 | Yamada |
| 2019/0037473 A1 | 12/2019 | Chen |
| 2019/0373679 A1 | 12/2019 | Fu |
| 2019/0374730 A1 | 12/2019 | Chen |
| 2019/0387795 A1 | 12/2019 | Fisher |
| 2020/0000143 A1 | 1/2020 | Anderson |
| 2020/0000146 A1 | 1/2020 | Anderson |
| 2020/0009600 A1 | 1/2020 | Tan |
| 2020/0016344 A1 | 1/2020 | Scheck |
| 2020/0022416 A1 | 1/2020 | Alarcon |
| 2020/0046030 A1 | 2/2020 | Krietzman |
| 2020/0068949 A1 | 3/2020 | Rasmussen |
| 2020/0085100 A1 | 3/2020 | Hoffman |
| 2020/0120989 A1 | 4/2020 | Danek |
| 2020/0120991 A1 | 4/2020 | Hatton |
| 2020/0146361 A1 | 5/2020 | Silver |
| 2020/0178598 A1 | 6/2020 | Mitchell |
| 2020/0178606 A1 | 6/2020 | Liu |
| 2020/0214349 A1 | 7/2020 | Liu |
| 2020/0221771 A1 | 7/2020 | Atkins |
| 2020/0221776 A1 | 7/2020 | Liu |
| 2020/0245692 A1 | 8/2020 | Cameron |
| 2020/0345058 A1 | 11/2020 | Bowen |
| 2020/0404975 A1 | 12/2020 | Chen |
| 2021/0015957 A1 | 1/2021 | Bush |
| 2021/0076733 A1 | 3/2021 | Liu |
| 2021/0112858 A1 | 4/2021 | Liu |
| 2021/0120880 A1 | 4/2021 | Liu |
| 2021/0153548 A1 | 5/2021 | Twite |
| 2021/0153549 A1 | 5/2021 | Twite |
| 2021/0153564 A1 | 5/2021 | Hourmand |
| 2021/0153565 A1 | 5/2021 | Twite |
| 2021/0153566 A1 | 5/2021 | Hourmand |
| 2021/0153567 A1 | 5/2021 | Twite |
| 2021/0153568 A1 | 5/2021 | Twite |
| 2021/0153569 A1 | 5/2021 | Twite |
| 2021/0177056 A1 | 6/2021 | Yilmaz |
| 2021/0212362 A1 | 7/2021 | Liu |
| 2021/0378303 A1 | 12/2021 | Liu |
| 2021/0401061 A1 | 12/2021 | Davis |
| 2022/0030942 A1 | 2/2022 | Lord |
| 2022/0069703 A1 | 3/2022 | Krishnamurthy |
| 2022/0151301 A1 | 5/2022 | Liu |
| 2022/0240589 A1 | 8/2022 | Liu |
| 2022/0273037 A1 | 9/2022 | Liu |
| 2022/0279857 A1 | 9/2022 | Liu |
| 2022/0287361 A1 | 9/2022 | Kim |
| 2022/0295876 A1 | 9/2022 | Liu |
| 2022/0395023 A1 | 12/2022 | Liu |
| 2022/0400747 A1 | 12/2022 | Liu |
| 2023/0001107 A1 | 1/2023 | Connolly |
| 2023/0013741 A1 | 1/2023 | Liu |
| 2023/0020762 A1 | 1/2023 | Liu |
| 2023/0165303 A1 | 6/2023 | Liu |
| 2023/0292839 A1 | 9/2023 | Kim |

FOREIGN PATENT DOCUMENTS

| | | | |
|---|---|---|---|
| CN | 104055225 | A | 9/2014 |
| CN | 104082853 | A | 10/2014 |
| CN | 204070580 | U | 1/2015 |
| CN | 104640708 | | 5/2015 |
| CN | 204499481 | U | 7/2015 |
| CN | 105747277 | A | 7/2016 |
| CN | 105768238 | A | 7/2016 |
| CN | 105795526 | A | 7/2016 |
| CN | 105876873 | A | 8/2016 |
| CN | 205432145 | U | 8/2016 |
| CN | 106108118 | A | 11/2016 |
| CN | 205831074 | A | 12/2016 |
| CN | 106422005 | | 2/2017 |
| CN | 205947130 | U | 2/2017 |
| CN | 206025223 | U | 3/2017 |
| CN | 206043451 | U | 3/2017 |
| CN | 206079025 | U | 4/2017 |
| CN | 206119183 | U | 4/2017 |
| CN | 206119184 | U | 4/2017 |
| CN | 106617319 | A | 5/2017 |
| CN | 206303211 | U | 7/2017 |
| CN | 206333372 | U | 7/2017 |
| CN | 107048479 | A | 8/2017 |
| CN | 206586397 | U | 10/2017 |
| CN | 206949536 | U | 2/2018 |
| CN | 107822195 | | 3/2018 |
| CN | 207185926 | | 4/2018 |
| CN | 105476071 | | 5/2018 |
| CN | 207383536 | | 5/2018 |
| CN | 207400330 | | 5/2018 |
| CN | 108283331 | A | 7/2018 |
| CN | 108355210 | A | 8/2018 |
| CN | 105876873 | B | 12/2018 |
| CN | 109619655 | A | 1/2019 |
| CN | 208354603 | | 1/2019 |
| CN | 208434721 | U | 1/2019 |
| CN | 106108118 | B | 4/2019 |
| CN | 208837110 | U | 5/2019 |
| CN | 209060228 | U | 7/2019 |
| CN | 110150760 | A | 8/2019 |
| CN | 209255084 | U | 8/2019 |
| CN | 105876870 | B | 11/2019 |
| CN | 209900345 | U | 1/2020 |
| CN | 210076566 | U | 2/2020 |
| CN | 210225387 | | 3/2020 |
| CN | 110946315 | A | 4/2020 |
| CN | 111229528 | | 6/2020 |
| CN | 111838775 | | 10/2020 |
| CN | 211675730 | U | 10/2020 |
| CN | 212441811 | | 2/2021 |

(56) References Cited

FOREIGN PATENT DOCUMENTS

| | | |
|---|---|---|
| CN | 214289213 | 9/2021 |
| CN | 214483267 | 10/2021 |
| CN | 215819888 | 2/2022 |
| CN | 217342045 | 9/2022 |
| CN | 217609513 | 10/2022 |
| CN | 217643921 U | 10/2022 |
| CN | 115336802 | 11/2022 |
| CN | 217826736 | 11/2022 |
| CN | 116807059 | 9/2023 |
| CN | 116850853 | 10/2023 |
| DE | 2656370 A1 | 6/1978 |
| DE | 1 528 391 A | 10/1978 |
| DE | 2656370 B2 | 11/1978 |
| DE | 2656370 C3 | 7/1979 |
| DE | 100 51 792 A1 | 5/2002 |
| DE | 10122065 A1 | 12/2002 |
| EP | 0 258 637 A1 | 3/1988 |
| EP | 0 295 122 A2 | 12/1988 |
| EP | 0 258 637 B1 | 6/1990 |
| EP | 0 442 510 A1 | 8/1991 |
| EP | 0 442 510 B1 | 1/1995 |
| EP | 0 516 565 B1 | 4/1996 |
| EP | 0 824 927 A | 2/1998 |
| EP | 0 833 695 A1 | 4/1998 |
| EP | 0 845 220 A1 | 6/1998 |
| EP | 0 893 071 A1 | 1/1999 |
| EP | 0 970 627 A1 | 1/2000 |
| EP | 1083952 B1 | 12/2005 |
| EP | 1 618 803 B1 | 12/2008 |
| EP | 2 605 616 A2 | 6/2013 |
| EP | 3 088 007 A1 | 11/2016 |
| EP | 3 192 381 A1 | 7/2017 |
| EP | 3 278 678 A1 | 2/2018 |
| EP | 3 298 912 A1 | 3/2018 |
| EP | 3 088 007 B1 | 11/2018 |
| EP | 3 434 118 A1 | 1/2019 |
| EP | 3 469 927 A1 | 4/2019 |
| EP | 3 505 098 | 7/2019 |
| EP | 3 520 634 A1 | 8/2019 |
| EP | 3 278 678 B1 | 10/2019 |
| EP | 3 545 778 A1 | 10/2019 |
| EP | 3 574 902 A1 | 12/2019 |
| EP | 3 516 971 | 3/2021 |
| EP | 3 528 651 | 5/2021 |
| EP | 3 837 999 A1 | 6/2021 |
| EP | 3 574 778 | 7/2021 |
| EP | 3 593 656 | 10/2021 |
| EP | 4252561 | 10/2023 |
| EP | 4033927 | 11/2023 |
| FR | 3043576 A1 | 5/2017 |
| FR | 3064502 A1 | 5/2018 |
| GB | 2566766 A | 3/2019 |
| GB | 2570439 A | 7/2019 |
| JP | 05093575 U | 12/1993 |
| JP | 2579614 Y2 | 8/1998 |
| JP | 2001069963 A | 3/2001 |
| JP | 2005288400 A | 10/2005 |
| JP | 2008-104966 A | 5/2008 |
| JP | 2011-500160 | 1/2011 |
| JP | 2012-507208 | 3/2012 |
| JP | 2014-004042 | 1/2014 |
| JP | 2019515684 | 6/2019 |
| JP | 2019521671 A | 8/2019 |
| JP | 2019-524113 | 9/2019 |
| JP | 2019-526240 | 9/2019 |
| JP | 2019-526241 | 9/2019 |
| JP | 2020535846 A | 12/2020 |
| JP | 2022032444 | 2/2022 |
| KR | 20120107219 A | 10/2012 |
| KR | 210-2013-0052119 | 5/2013 |
| KR | 10-2013-0095024 | 8/2013 |
| KR | 20230024816 | 2/2023 |
| KR | 20230115452 | 8/2023 |
| KR | 20230123537 | 8/2023 |
| KR | 102584559 | 10/2023 |
| KR | 102587103 | 10/2023 |
| WO | WO 92/21332 A1 | 12/1992 |
| WO | WO9309881 | 5/1993 |
| WO | WO 2000/050111 A | 8/2000 |
| WO | 2002/055131 A2 | 7/2002 |
| WO | WO 02094342 A2 | 11/2002 |
| WO | 2003/055486 A | 7/2003 |
| WO | 2003/101454 A | 12/2003 |
| WO | WO 2004/080216 | 9/2004 |
| WO | 2007/083088 A1 | 7/2007 |
| WO | 2008/076717 A1 | 6/2008 |
| WO | 2009/096346 A1 | 8/2009 |
| WO | 2012/062600 A1 | 5/2012 |
| WO | WO 2012/138835 A2 | 10/2012 |
| WO | 2013/028934 A1 | 2/2013 |
| WO | 2014/182736 A1 | 11/2014 |
| WO | 2015/128499 A1 | 3/2015 |
| WO | WO2015/084544 A1 | 6/2015 |
| WO | 2015/115006 A1 | 8/2015 |
| WO | WO 2015/157824 A1 | 10/2015 |
| WO | 2016/010864 A1 | 1/2016 |
| WO | 2016/118941 A1 | 7/2016 |
| WO | WO 2016/116386 | 7/2016 |
| WO | 2016/175720 A1 | 11/2016 |
| WO | 2016/196915 A1 | 12/2016 |
| WO | WO 2017/076590 A1 | 5/2017 |
| WO | WO 2017/108268 A1 | 6/2017 |
| WO | WO 2017/143515 A1 | 8/2017 |
| WO | WO 2017/177159 A3 | 10/2017 |
| WO | WO 2017/197704 A1 | 11/2017 |
| WO | WO 2017/205692 | 11/2017 |
| WO | WO 2017/206022 A1 | 12/2017 |
| WO | WO 2017/206212 A1 | 12/2017 |
| WO | WO 2017/215221 A1 | 12/2017 |
| WO | WO 2018/000761 A1 | 1/2018 |
| WO | WO 2018/000829 A1 | 1/2018 |
| WO | WO 2018/023920 A1 | 2/2018 |
| WO | WO2018/027189 A2 | 2/2018 |
| WO | WO 2018/032672 A1 | 2/2018 |
| WO | WO 2018/040380 A1 | 3/2018 |
| WO | WO 2018/041106 A1 | 3/2018 |
| WO | WO 2018/058884 A1 | 4/2018 |
| WO | WO 2018/111843 | 6/2018 |
| WO | WO 2018/113669 A1 | 6/2018 |
| WO | WO 2018/115781 A1 | 6/2018 |
| WO | WO 2018/163366 A1 | 9/2018 |
| WO | WO 2018/167066 | 9/2018 |
| WO | WO 2018/188616 A1 | 10/2018 |
| WO | WO 2018/188638 A1 | 10/2018 |
| WO | WO 2018/211252 A1 | 11/2018 |
| WO | WO 2018/220586 A2 | 12/2018 |
| WO | WO2018/220599 A1 | 12/2018 |
| WO | WO 2019/016681 | 1/2019 |
| WO | WO 2019/048749 A1 | 3/2019 |
| WO | WO 2019/052506 A1 | 3/2019 |
| WO | WO 2019/052574 A1 | 3/2019 |
| WO | WO 2019/069160 A1 | 4/2019 |
| WO | WO 2019/138076 A1 | 7/2019 |
| WO | WO 2019/173923 | 9/2019 |
| WO | WO 2019/198688 | 10/2019 |
| WO | WO 2019/211324 | 11/2019 |
| WO | WO 2019/238064 | 12/2019 |
| WO | WO 2019/242746 A1 | 12/2019 |
| WO | WO 2020/019030 A1 | 1/2020 |
| WO | WO 2020/048437 A1 | 3/2020 |
| WO | WO 2020/057636 A2 | 3/2020 |
| WO | WO2020187138 A1 | 9/2020 |
| WO | WO 2020/225534 A1 | 11/2020 |
| WO | WO 2020/254862 A1 | 12/2020 |
| WO | WO 2021/036827 A1 | 3/2021 |
| WO | WO2022/104246 | 5/2022 |
| WO | WO2022/200151 | 9/2022 |
| WO | WO2022/203187 | 9/2022 |
| WO | WO 2023/018059 | 2/2023 |
| WO | WO2023/143058 | 8/2023 |

(56) References Cited

FOREIGN PATENT DOCUMENTS

| WO | WO2023/179691 | 9/2023 |
|---|---|---|
| WO | WO2023/249371 | 12/2023 |

OTHER PUBLICATIONS

UKIPO Search Report for corresponding GB Application No. GB2201641.4 dated May 30, 2022.
UKIPO Search Report for GB Application No. GB2118196.1 dated May 30, 2022.
ISR and Written Opinion for International Application No. PCT/GB2021/053316 mailed Mar. 22, 2022.
ISR and Written Opinion mailed Mar. 10, 2022 for Intl. Appl. No. PCT/GB2021053312.
ISR and Written Opinion mailed Mar. 10, 2022 for Intl. Appl. No. PCT/GB2021053311.
ISR and Written Opinion mailed Mar. 10, 2022 for Intl. Appl. No. PCT/GB2021053316.
UKIPO Search Report dated Nov. 24, 2021 for Application No. GB2111261.0.
UKIPO Search Report dated Nov. 24, 2021 for Application No. GB2113658.5.
UKIPO Search Report dated Nov. 24, 2021 for Application No. GB2113623.9.
EPO Search Report dated Nov. 12, 2021 for corresponding European Application No. 19870060.1.
EPO Search Report dated Oct. 27, 2021 for corresponding European Application No. 19870058.5.
International Search Report and Written Opinion for International Appl. No. PCT/GB2021/050842 mailed Jul. 5, 2021.
International Search Report and Written Opinion for International Appl. No. PCT/GB2021/050817 mailed Jun. 17, 2021.
UKIPO Search Report for UK Appl. No. GB2104872.3 dated Jun. 25, 2021.
EPO Search Report and Search Opinion for International Appl. No. PCT/IB2019/060812 dated Jun. 22, 2021.
Extended European Search Report and Search Opinion for corresponding EP Application No. 20214228.7 dated May 26, 2021.
International Search Report and Written Opinion for International Appl. No. PCT/IB2019/055192 dated Apr. 29, 2020.
International Search Report for corresponding PCT Appl. No. PCT/GB2020/053219 mailed Mar. 31, 2021.
Written Opinion mailed Nov. 10, 2020 for corresponding International Application No. PCT/IB2019/060812.
International Search Report mailed Nov. 10, 2020 for corresponding International Application No. PCT/IB2019/060812.
EPO Search Report mailed Nov. 9, 2020 for corresponding EPO Application No. 19870059.3 (PCT/IB2019/060808).
Written Opinion mailed Nov. 4, 2020 for corresponding International Application No. PCT/IB2019/060806.
International Search Report mailed Nov. 4, 2020 for corresponding International Application No. PCT/IB2019/060806.
Written Opinion mailed Nov. 4, 2020 for corresponding International Application No. PCT/IB2019/060807.
International Search Report mailed Nov. 4, 2020 for corresponding International Application No. PCT/IB2019/060807.
Written Opinion mailed Oct. 20, 2020 for corresponding International Application No. PCT/IB2019/060811.
International Search Report mailed Oct. 20, 2020 for corresponding International Application No. PCT/IB2019/060811.
ISR and Written Opinion mailed Oct. 20, 2020 for International Application No. PCT/IB2019/060809.
Written Opinion mailed Oct. 19, 2020 for corresponding International Application No. PCT/IB2019/060810.
International Search Report mailed Oct. 19, 2020 for corresponding International Application No. PCT/IB2019/060810.
EPO Search Report dated Sep. 16, 2020 for corresponding EPO Application No. 20168231.
Extended EPO Search Report mailed Sep. 15, 2020 for corresponding EPO Application No. 20168938.7.
Written Opinion mailed Jun. 25, 2020 for corresponding International Application No. PCT/IB2019/060808.
International Search Report mailed Jun. 25, 2020 for corresponding International Application No. PCT/IB2019/060808.
Written Opinion mailed Apr. 29, 2020 for corresponding International Application No. PCT/IB2019/055192.
International Search Report mailed Apr. 29, 2020 for corresponding International Application No. PCT/IB2019/055192.
EPO search report dated Sep. 20, 2017 for corresponding EPO Application No. 20168245.7.
EPO Supplementary Search Report for EPO Application No. EP 3 278 678 A4 dated Oct. 4, 2018.
International Search Report for International Appl. No. WO 2017/177159 A3 mailed Sep. 26, 2017.
EPO Supplementary Search Report for EPO Application No. EP 1 618 803 A4 dated Jul. 27, 2007.
Japanese Exam Report mailed Dec. 6, 2022, for co-pending Japanese application No. 2022-543531.
Search Report, co-pending CL Application No. 202201809 dated Dec. 20, 2023; 10 pages.(with English translation).
Akira Kubo, Part 1: What is Personal Authentication?—The Last Resort for Internet Security-Series: Re-Introduction to PKI, Japan, @IT, Apr. 5, 2003; https://atmarkit.itmedia.co.jp/fsecurity/rensai/re_pki01/re_pki01.html (newly cited reference showing well-known technique) (No English version).
Extended European Search Report, co-pending EP Application No. 24159329.2 dated May 8, 2024; 7 pages.
Extended European Search Report, co-pending EP Application No. 24159332.6 dated May 13, 2024; 7 pages.
Official Action issued Jul. 14, 2024 for co-pending EG Application No. EG/2022/1483; 8 pages.
Notice of Allowance issued Jul. 11, 2024 for co-pending KR Application No. 10-2023-7030275; 7 pages.
Notice of Allowance issued Jun. 7, 2024 for co-pending KR Application No. 10-2023-7030279; 7 pages.
Extended European Search Report dated May 8, 2024 for co-pending EP Application No. 24159329.2; 7 pages.
Extended European Search Report dated May 13, 2024 for co-pending EP Application No. 24159332.6; 7 pages.

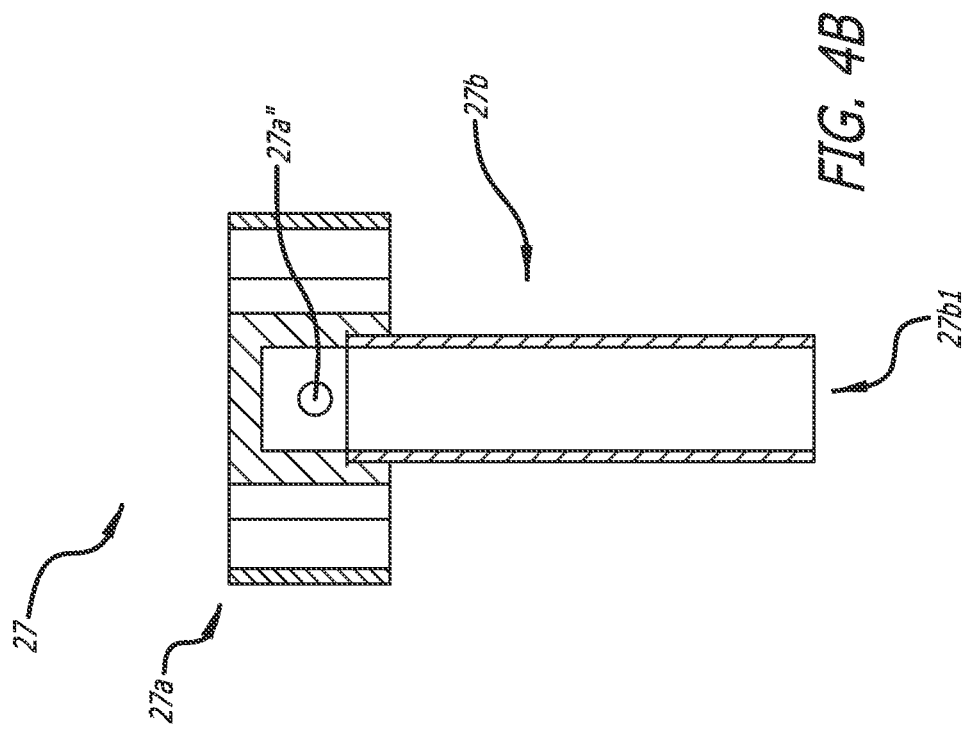
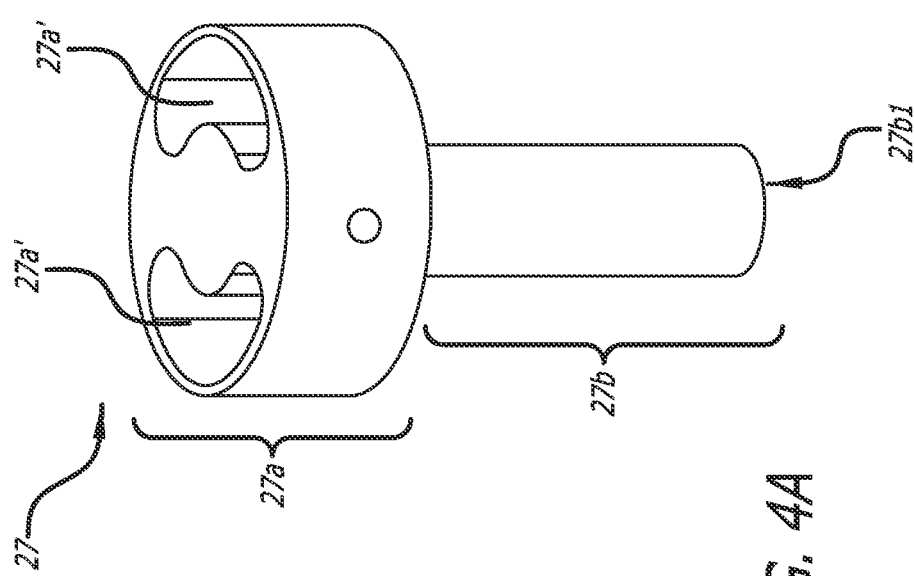
FIG. 4B
FIG. 4A

| Port # | Primary Function | Secondary Function |
|---|---|---|
| GPIO.0 | digital GPIO | used for chip test |
| GPIO.1 | digital GPIO | ADC channel 0 |
| GPIO.2 | digital GPIO | ADC channel 1 |
| GPIO.3 | rms current | digital GPIO |
| GPIO.4 | digital GPIO | used for chip test |
| GPIO.5 | digital GPIO | I2C address select ADR0 |
| GPIO.6 | digital GPIO | I2C address select ADR1 |
| GPIO.7 | digital GPIO | I2C address select ADR2 |

FIG. 35

HOOKAH DEVICE

CROSS REFERENCES TO RELATED APPLICATIONS

The present application is a continuation of U.S. application Ser. No. 17/300,931, filed Dec. 15, 2021, which claims the benefit of priority to and incorporates by reference herein the entirety of all the following applications:

U.S. application Ser. No. 17/223,846 filed on 6 Apr. 2021 (the '846 application), which claims the benefit of priority to and incorporates by reference herein the entirety of each of: European patent application no. 20168245.7, filed on 6 Apr. 2020; European patent application no. 20168231.7, filed on 6 Apr. 2020; and European patent application no. 20168938.7, filed on 9 Apr. 2020; the '846 application is a continuation in part of U.S. application Ser. No. 16/889,667, filed on 1 Jun. 2020; the '846 application is also a continuation in part of U.S. application Ser. No. 17/065,992, filed on 8 Oct. 2020, which itself is a continuation in part of U.S. application Ser. No. 16/889,667, filed on 1 Jun. 2020 and claims the benefit of priority to U.S. provisional patent application No. 63/064,386, filed on 11 Aug. 2020; the '846 application is also a continuation in part of U.S. patent application Ser. No. 17/122,025, filed on 15 Dec. 2020 which itself claims the benefit of priority to International patent application nos. PCT/IB2019/060808, PCT/IB2019/060810, PCT/IB2019/060811, and PCT/IB2019/060812, all filed on 15 Dec. 2019; and the '846 application is also a continuation in part of U.S. application Ser. No. 17/220,189, filed on 1 Apr. 2021;

U.S. application Ser. No. 17/122,025 filed on 15 Dec. 2020 which claims the benefit of priority to International patent application no. PCT/IB2019/060808, filed on 15 Dec. 2019, International patent application no. PCT/IB2019/060810, filed on 15 Dec. 2019, International patent application no. PCT/IB2019/060811, filed on 15 Dec. 2019, International patent application no. PCT/IB2019/060812, filed on 15 Dec. 2019, European patent application no. 20168245.7, filed on 6 Apr. 2020, European patent application no. 20168231.7, filed on 6 Apr. 2020, and European patent application no. 20168938.7, filed on 9 Apr. 2020;

U.S. application Ser. No. 17/220,189 filed on 1 Apr. 2021 which claims the benefit of priority to European Patent Application No. 20168231.7, filed on 6 Apr. 2020; and GB patent application no. 2104872.3, filed 6 Apr. 2021, all of the foregoing applications are incorporated herein by reference in their entirety.

FIELD

The present invention relates to a hookah device. The present invention more particularly relates to a hookah device which generates a mist using ultrasonic vibrations.

BACKGROUND

The traditional hookah is a smoking device which burns tobacco leaves that have been crushed and prepared specifically to be heated using charcoal. The heat from the charcoal causes the crushed tobacco leaves to burn, producing smoke that is pulled through water in a glass chamber and to the user by inhalation. The water is used to cool the hot smoke for ease of inhalation.

Hookah use began centuries ago in ancient Persia and India. Today, hookah cafés are gaining popularity around the world, including the United Kingdom, France, Russia, the Middle East and the United States.

A typical modern hookah has a head (with holes in the bottom), a metal body, a water bowl and a flexible hose with a mouthpiece. New forms of electronic hookah products, including steam stones and hookah pens, have been introduced. These products are battery or mains powered and heat liquid containing nicotine, flavorings and other chemicals to produce smoke which is inhaled.

Although many users consider it less harmful than smoking cigarettes, hookah smoking has many of the same health risks as cigarette smoking.

Thus, a need exists in the art for an improved hookah device which seeks to address at least some of the problems described herein.

The present invention seeks to provide an improved hookah device.

SUMMARY

The present invention provides a hookah device as claimed in claim 1 and a hookah as claimed in claim 19. The present invention also provides preferred embodiments as claimed in the dependent claims.

The various examples of this disclosure which are described below have multiple benefits and advantages over conventional hookah devices and hookahs. These benefits and advantages are set out in the description below.

The hookah device of examples of this disclosure has an environmental benefit since the hookah device does not emit any smoke and hookah device removes the need to burn charcoal.

According to some arrangements, there is provided a hookah device comprising: a plurality of ultrasonic mist generator devices which are each provided with a respective mist outlet port; a driver device which is connected electrically to each of the mist generator devices and configured to activate the mist generator devices; and a hookah attachment arrangement which is configured to attach the hookah device to a hookah, the hookah attachment arrangement having a hookah outlet port which provides a fluid flow path from the mist outlet ports of the mist generator devices and out of the hookah device such that, when at least one of the mist generator devices is activated by the driver device, mist generated by each activated mist generator device flows along the fluid flow path and out of the hookah device to the hookah.

In some arrangements, the driver device is connected electrically to each of the mist generator devices by a data bus and the driver device is configured to identify and control each mist generator device using a respective unique identifier for the mist generator device.

In some arrangements, each mist generator device comprises: an identification arrangement comprising: an integrated circuit having a memory which stores a unique identifier for the mist generator device; and an electrical connection which provides an electronic interface for communication with the integrated circuit.

In some arrangements, the driver device is configured to control each respective mist generator device to activate independently of the other mist generator devices.

In some arrangements, the driver device is configured to control the mist generator devices to activate in a predetermined sequence.

In some arrangements, each mist generator device comprises: a manifold having a manifold pipe which is in fluid communication with the mist outlet ports of the mist generator devices, wherein mist output from the mist outlet ports combines in the manifold pipe and flows through the manifold pipe and out from the hookah device.

In some arrangements, the hookah device comprises four mist generator devices which are releasably coupled to the manifold at 90° relative to one another.

In some arrangements, each mist generator device is releasably attached to the driver device so that each mist generator device is separable from the driver device.

In some arrangements, each mist generator device comprises: a mist generator housing which is elongate and comprises an air inlet port and the said mist outlet port; a liquid chamber provided within the mist generator housing, the liquid chamber containing a liquid to be atomized; a sonication chamber provided within the mist generator housing; a capillary element extending between the liquid chamber and the sonication chamber such that a first portion of the capillary element is within the liquid chamber and a second portion of the capillary element is within the sonication chamber; an ultrasonic transducer having a generally planar atomization surface which is provided within the sonication chamber, the ultrasonic transducer being mounted within the mist generator housing such that the plane of the atomization surface is substantially parallel with a longitudinal length of the mist generator housing, wherein part of the second portion of the capillary element is superimposed on part of the atomization surface, and wherein the ultrasonic transducer is configured to vibrate the atomization surface to atomize a liquid carried by the second portion of the capillary element to generate a mist comprising the atomized liquid and air within the sonication chamber; and an airflow arrangement which provides an air flow path between the air inlet port, the sonication chamber and the air outlet port.

In some arrangements, each mist generator device further comprises: a transducer holder which is held within the mist generator housing, wherein the transducer element holds the ultrasonic transducer and retains the second portion of the capillary element superimposed on part of the atomization surface; and a divider portion which provides a barrier between the liquid chamber and the sonication chamber, wherein the divider portion comprises a capillary aperture through which part of the first portion of the capillary element extends.

In some arrangements, the capillary element is 100% bamboo fiber.

In some arrangements, the airflow arrangement is configured to change the direction of a flow of air along the air flow path such that the flow of air is substantially perpendicular to the atomization surface of the ultrasonic transducer as the flow of air passes into the sonication chamber.

In some arrangements, the liquid chamber contains a liquid having a kinematic viscosity between 1.05 Pa·s and 1.412 Pa·s and a liquid density between 1.1 g/ml and 1.3 g/ml.

In some arrangements, the liquid chamber contains a liquid comprising approximately a 2:1 molar ratio of levulinic acid to nicotine.

In some arrangements, the driver device comprises: an AC driver which is configured to generate an AC drive signal at a predetermined frequency to drive a respective ultrasonic transducer in each mist generator device; an active power monitoring arrangement which is configured to monitor the active power used by the ultrasonic transducer when the ultrasonic transducer is driven by the AC drive signal, wherein the active power monitoring arrangement is configured to provide a monitoring signal which is indicative of an active power used by the ultrasonic transducer; a processor which is configured to control the AC driver and to receive the monitoring signal drive from the active power monitoring arrangement; and a memory storing instructions which, when executed by the processor, cause the processor to:

A. control the AC driver to output an AC drive signal to the ultrasonic transducer at a predetermined sweep frequency;
B. calculate the active power being used by the ultrasonic transducer based on the monitoring signal;
C. control the AC driver to modulate the AC drive signal to maximize the active power being used by the ultrasonic transducer;
D. store a record in the memory of the maximum active power used by the ultrasonic transducer and the sweep frequency of the AC drive signal;
E. repeat steps A-D for a predetermined number of iterations with the sweep frequency incrementing with each iteration such that, after the predetermined number of iterations has occurred, the sweep frequency has been incremented from a start sweep frequency to an end sweep frequency;
F. identify from the records stored in the memory the optimum frequency for the AC drive signal which is the sweep frequency of the AC drive signal at which a maximum active power is used by the ultrasonic transducer; and
G. control the AC driver to output an AC drive signal to the ultrasonic transducer at the optimum frequency to drive the ultrasonic transducer to atomize a liquid.

In some arrangements, the active power monitoring arrangement comprises: a current sensing arrangement which is configured to sense a drive current of the AC drive signal driving the ultrasonic transducer, wherein the active power monitoring arrangement is configured to provide a monitoring signal which is indicative of the sensed drive current.

In some arrangements, the memory stores instructions which, when executed by the processor, cause the processor to: repeat steps A-D with the sweep frequency being incremented from a start sweep frequency of 2900 kHz to an end sweep frequency of 2960 kHz.

In some arrangements, the memory stores instructions which, when executed by the processor, cause the processor to: repeat steps A-D with the sweep frequency being incremented from a start sweep frequency of 2900 kHz to an end sweep frequency of 3100 kHz.

In some arrangements, the AC driver is configured to modulate the AC drive signal by pulse width modulation to maximize the active power being used by the ultrasonic transducer.

According to some arrangements, there is provided a hookah comprising: a water chamber; an elongate stem having a first end which is attached to the water chamber, the stem comprising a mist flow path which extends from a second end of the stem, through the stem, to the first end; and a hookah device according to any one of claims 1 to 19 as defined hereinafter, wherein the hookah attachment arrangement of the hookah device is attached to the stem of the hookah at the second end of the stem.

BRIEF DESCRIPTION OF THE DRAWINGS

So that the present invention may be more readily understood, embodiments of the present invention will now be described, by way of example, with reference to the accompanying drawings, in which:

FIG. 4A is an isometric view of an airflow member of the inhaler liquid reservoir structure according to FIGS. 2 and 3.

FIG. 4B is a cross section view of the airflow member shown in FIG. 4A.

FIG. 35 is a table showing port functions of an example of this disclosure.

DETAILED DESCRIPTION

Figure 1:
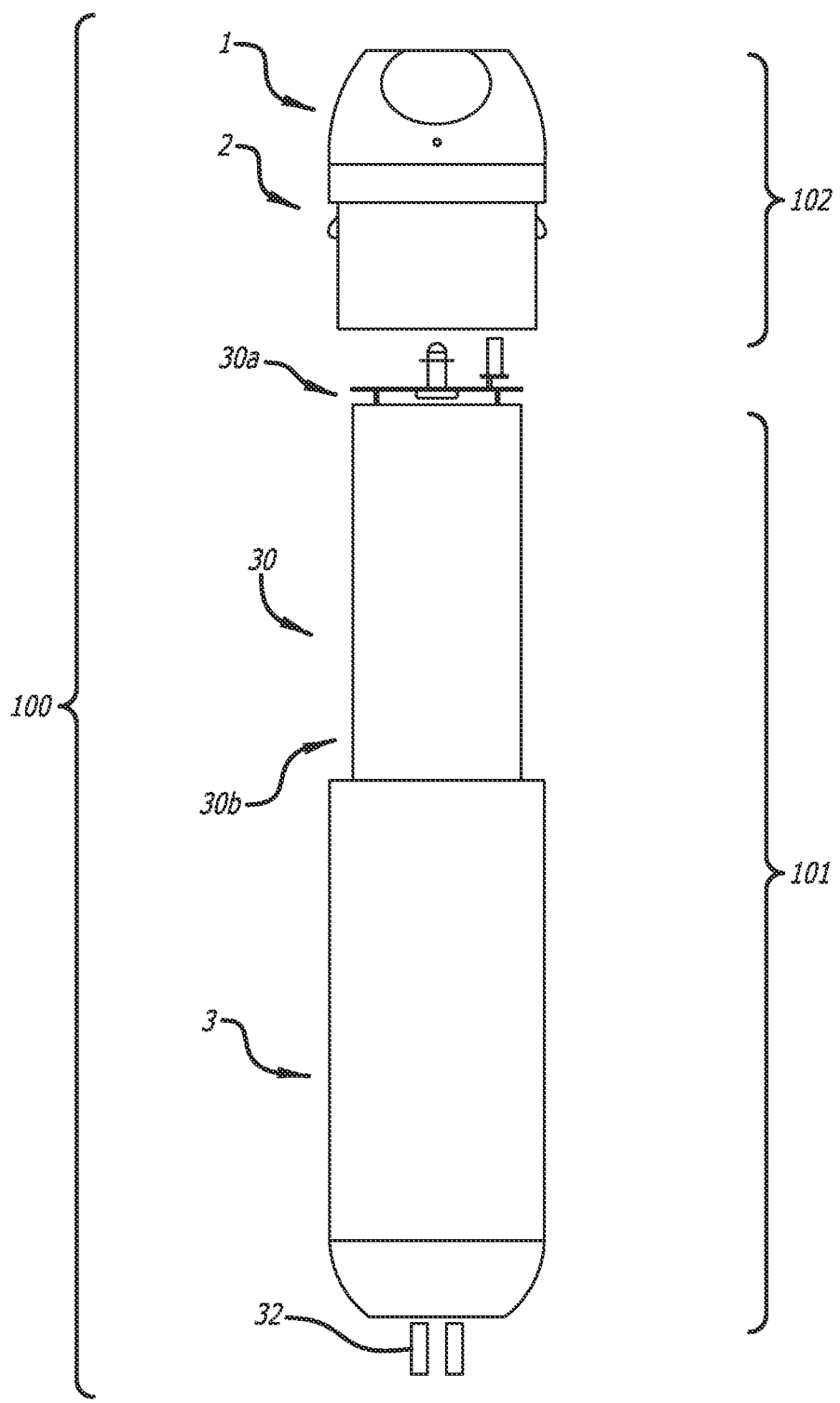
FIG. 1 is an exploded view of components of an ultrasonic mist inhaler.

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

The following disclosure provides many different embodiments, or examples, for implementing different features of the provided subject matter. Specific examples of components, concentrations, applications and arrangements are described below to simplify the present disclosure. These are, of course, merely examples and are not intended to be limiting. For example, the attachment of a first feature and a second feature in the description that follows may include embodiments in which the first feature and the second feature are attached in direct contact, and may also include embodiments in which additional features may be positioned between the first feature and the second feature, such that the first feature and the second feature may not be in direct contact. In addition, the present disclosure may repeat reference numerals and/or letters in the various examples. This repetition is for the purpose of simplicity and clarity and does not in itself dictate a relationship between the various embodiments and/or configurations discussed.

The following disclosure describes representative arrangements or examples. Each arrangement or example may be considered to be an embodiment and any reference to an "arrangement" or an "example" may be changed to "embodiment" in the present disclosure.

A hookah device of some arrangements incorporates ultrasonic aerosolization technology. The hookah device of some arrangements is configured to replace a conventional hookah head (coal-heated or electronically heated). The hookah device of some arrangements releasably attaches to an existing stem or metal body and water chamber/bowl in place of the conventional hookah head which houses the tobacco and the charcoal (or electronic heating element).

In other arrangements, the hookah device is provided with a stem/body and a water chamber/bowl as a complete hookah apparatus.

Hookah water bowls come in various shapes and sizes, ornamented with traditional or futuristic decorations as per individual preferences. The design and development of the ultrasonic aerosolizing hookah device of some arrangements was executed, keeping the tradition in mind, to create a replaceable head that fits onto any existing hookah.

The following disclosure describes the components and functionality of an ultrasonic mist generator device. The disclosure then describes the hookah device of some arrangements which incorporates a plurality of ultrasonic mist generator devices.

Conventional electronic vaporizing inhalers tend to rely on inducing high temperatures of a metal component configured to heat a liquid in the inhaler, thus vaporizing the liquid that can be breathed in. The liquid typically contains nicotine and flavorings blended into a solution of propylene glycol (PG) and vegetable glycerin (VG), which is vaporized via a heating component at high temperatures. Problems with conventional inhalers may include the possibility of burning metal and subsequent breathing in of the metal along with the burnt liquid. In addition, some may not prefer the burnt smell or taste caused by the heated liquid.

FIGS. 1 to 4 illustrate an ultrasonic mist inhaler comprising a sonication chamber. It is noted that the expression "mist" used in the following disclosure means the liquid is not heated as usually in traditional inhalers known from the prior art. In fact, traditional inhalers use heating elements to heat the liquid above its boiling temperature to produce a vapor, which is different from a mist.

When sonicating liquids at high intensities, the sound waves that propagate into the liquid media result in alternating high-pressure (compression) and low-pressure (rarefaction) cycles, at different rates depending on the frequency. During the low-pressure cycle, high-intensity ultrasonic waves create small vacuum bubbles or voids in the liquid. This phenomenon is termed cavitation. When the bubbles attain a volume at which they can no longer absorb energy, they collapse violently during a high-pressure cycle. During the implosion, very high pressures are reached locally. At cavitation, broken capillary waves are generated, and tiny droplets break the surface tension of the liquid and are quickly released into the air, taking mist form.

The following will explain more precisely the cavitation phenomenon.

When the liquid is atomized by ultrasonic vibrations, micro water bubbles are produced in the liquid.

The bubble production is a process of formation of cavities created by the negative pressure generated by intense ultrasonic waves generated by the means of ultrasonic vibrations.

High intensity ultrasonic sound waves leading to rapid growth of cavities with relatively low and negligible reduction in cavity size during the positive pressure cycle.

Ultrasound waves, like all sound waves, consist of cycles of compression and expansion. When in contact with a liquid, Compression cycles exert a positive pressure on the liquid, pushing the molecules together, Expansion cycles exert a negative pressure, puffing the molecules away from another.

Intense ultrasound waves create regions of positive pressure and negative pressure. A cavity can form and grow during the episodes of negative pressure. When the cavity attains a critical size, the cavity implodes.

The amount of negative pressure needed depends on the type and purity of the liquid. For truly pure liquids, tensile strengths are so great that available ultrasound generators cannot produce enough negative pressure to make cavities. In pure water, for instance, more than 1,000 atmospheres of negative pressure would be required, yet the most powerful ultrasound generators produce only about 50 atmospheres of negative pressure. The tensile strength of liquids is reduced by the gas trapped within the crevices of the liquid particles. The effect is analogous to the reduction in strength that occurs from cracks in solid materials. When a crevice filled with gas is exposed to a negative-pressure cycle from a sound wave, the reduced pressure makes the gas in the crevice expand until a small bubble is released into solution.

However, a bubble irradiated with ultrasound continually absorbs energy from alternating compression and expansion cycles of the sound wave. These cause the bubbles to grow and contract, striking a dynamic balance between the void inside the bubble and the liquid outside. In some cases, ultrasonic waves will sustain a bubble that simply oscillates in size. In other cases, the average size of the bubble will increase.

Cavity growth depends on the intensity of sound. High-intensity ultrasound can expand the cavity so rapidly during the negative-pressure cycle that the cavity never has a chance to shrink during the positive-pressure cycle. In this process, cavities can grow rapidly in the course of a single cycle of sound.

For low-intensity ultrasound the size of the cavity oscillates in phase with the expansion and compression cycles. The surface of a cavity produced by low-intensity ultrasound is slightly greater during expansion cycles than during compression cycles. Since the amount of gas that diffuses in or out of the cavity depends on the surface area, diffusion into the cavity during expansion cycles will be slightly greater than diffusion out during compression cycles. For each cycle of sound, then, the cavity expands a little more than it shrinks. Over many cycles the cavities will grow slowly.

It has been noticed that the growing cavity can eventually reach a critical size where it will most efficiently absorb energy from the ultrasound. The critical size depends on the frequency of the ultrasound wave. Once a cavity has experienced a very rapid growth caused by high intensity ultrasound, it can no longer absorb energy as efficiently from the sound waves. Without this energy input the cavity can no longer sustain itself. The liquid rushes in and the cavity implodes due to a non-linear response.

The energy released from the implosion causes the liquid to be fragmented into microscopic particles which are dispersed into the air as mist.

The equation for description of the above non-linear response phenomenon may be described by the "Rayleigh-Plesset" equation. This equation can be derived from the "Navier-Stokes" equation used in fluid dynamics.

The inventors approach was to rewrite the "Rayleigh-Plesset" equation in which the bubble volume, V, is used as the dynamic parameter and where the physics describing the dissipation is identical to that used in the more classical form where the radius is the dynamic parameter.

The equation used derived as follows:

$$\frac{\left|\frac{1}{c^2}\frac{\delta^2 \phi}{\delta t^2}\right|}{\nabla^2 \phi} \sim \left(\frac{R}{\lambda}\right)^2 \ll 1 \frac{1}{4\pi}\left(\frac{4\pi}{3V}\right)^{\frac{1}{3}}\left(\ddot{V} - \frac{\dot{V}^2(t)}{6V}\right) =$$

$$\frac{1}{\rho_0}\left(\left(p_0 + 2\sigma\left(\frac{4\pi}{3V_0}\right)^{\frac{1}{3}} - p_v\right)\left(\frac{V_0}{V}\right)^\kappa + p_v - 2\sigma\left(\frac{4\pi}{3V}\right)^{\frac{1}{3}} - p_0 - P(t)\right)$$

wherein:
V is the bubble volume
$V_0$ is the equilibrium bubble volume
$\rho_0$ is the liquid density (assumed to be constant)
$\sigma$ is the surface tension
$p_V$ is the vapor pressure
$p_0$ is the static pressure in the liquid just outside the bubble wall
$\kappa$ is the polytropic index of the gas
t is the time
R(t) is the bubble radius
P(t) is the applied pressure
c is the speed sound of the liquid
$\phi$ is the velocity potential
$\lambda$ is the wavelength of the insonifying field
In the ultrasonic mist inhaler, the liquid has a kinematic viscosity between 1.05 Pa·sec and 1.412 Pa·sec.

By solving the above equation with the right parameters of viscosity, density and having a desired target bubble volume of liquid spray into the air, it has been found that the frequency range of 2.8 MHz to 3.2 MHz for liquid viscosity range of 1.05 Pa·s and 1.412 Pa·s produce a bubble volume of about 0.25 to 0.5 microns.

The process of ultrasonic cavitation has a significant impact on the nicotine concentration in the produced mist.

No heating elements are involved, thereby leading to no burnt elements and reducing second-hand smoke effects.

In some arrangements, said liquid comprises 57-70% (w/w) vegetable glycerin and 30-43% (w/w) propylene glycol, said propylene glycol including nicotine and optionally flavorings.

In the ultrasonic mist inhaler, a capillary element may extend between the sonication chamber and the liquid chamber.

In the ultrasonic mist inhaler, the capillary element is a material at least partly in bamboo fibers.

The capillary element allows a high absorption capacity, a high rate of absorption as well as a high fluid-retention ratio.

It was found that the inherent properties of the proposed material used for the capillarity have a significant impact on the efficient functioning of the ultrasonic mist inhaler.

Further, inherent properties of the proposed material include a good hygroscopicity while maintaining a good permeability. This allows the drawn liquid to efficiently permeate the capillary while the observed high absorption capacity allows the retention of a considerable amount of liquid thus allowing the ultrasonic mist inhaler to last for a longer time when compared with the other products available in the market.

Another significant advantage of using the bamboo fibers is the naturally occurring antimicrobial bio-agent namely "Kun" inherently present within the bamboo fiber making it antibacterial, anti-fungal and odor resistant, making it suitable for medical applications.

The inherent properties have been verified using numerical analysis regarding the benefits of the bamboo fiber for sonication.

The following formulae have been tested with bamboo fibers material and others material such cotton, paper, or other fiber strands for the use as capillary element and demonstrates that bamboo fibers have much better properties for the use in sonication:

$$C = A + \frac{T}{W_f} - \frac{1}{P_f} + (1-\alpha)\frac{V_d}{W_f}$$

wherein:
C (cc/gm of fluid/gm) is the volume per mass of the liquid absorbed divided by the dry mass of the capillary element,
A (cm$^2$) is the total surface area of the capillary element
T (cm) is the thickness of the capillary element,
$W_f$ (gm) is the mass of the dry capillary element,
$P_f$ (cc/g.sec) is the density of the dry capillary element,
$\alpha$ is the ratio of increase in volume of capillary element upon wetting to the volume of liquid diffused in the capillary element,
$V_d$ (cc) is the amount of liquid diffused in the capillary element, $$\text{Absorbent Rate, } Q = \frac{\pi r \gamma 1 \cos\theta}{2\eta} \cdot \left(\frac{T}{W_f} - \frac{1}{AP_f}\right)$$

Q (cc/sec) is the amount of liquid absorbed per unit time,
r (cm) is the radius of the pores within the capillary element,
$\gamma$ (N/m) is the surface tension of the liquid,
$\theta$ (degrees) is the angle of contact of the fiber,
$\eta$ (m$^2$/sec) is the viscosity of the fluid.
FIG. 1 depicts a disposable ultrasonic mist inhaler 100. As can be seen in FIG. 1, the ultrasonic mist inhaler 100 has a cylindrical body with a relatively long length as compared to the diameter. In terms of shape and appearance, the ultrasonic mist inhaler 100 is designed to mimic the look of a typical cigarette. For instance, the inhaler can feature a first portion 101 that primarily simulates the tobacco rod portion of a cigarette and a second portion 102 that primarily simulates a filter. In the disposable arrangement, the first portion and second portion are regions of a single, but-separable device. The designation of a first portion 101 and a second portion 102 is used to conveniently differentiate the components that are primarily contained in each portion.

As can be seen in FIG. 1, the ultrasonic mist inhaler comprises a mouthpiece 1, a liquid reservoir structure 2 and a casing 3. The first portion 101 comprises the casing 3 and the second portion 102 comprises the mouthpiece 1 and the reservoir structure 2.

The first portion 101 contains the power supply energy.

An electrical storage device 30 powers the ultrasonic mist inhaler 100. The electrical storage device 30 can be a battery, including but not limited to a lithium-ion, alkaline, zinc-carbon, nickel-metal hydride, or nickel-cadmium battery; a super capacitor; or a combination thereof. In the disposable arrangement, the electrical storage device 30 is not rechargeable, but, in the reusable arrangement, the electrical storage device 30 would be selected for its ability to recharge. In the disposable arrangement, the electrical storage device 30 is primarily selected to deliver a constant voltage over the life of the inhaler 100. Otherwise, the performance of the inhaler would degrade over time. Preferred electrical storage devices that are able to provide a consistent voltage output over the life of the device include lithium-ion and lithium polymer batteries.

The electrical storage device 30 has a first end 30a that generally corresponds to a positive terminal and a second end 30b that generally corresponds to a negative terminal. The negative terminal is extending to the first end 30a.

Because the electrical storage device 30 is located in the first portion 101 and the liquid reservoir structure 2 is located in the second portion 102, the joint needs to provide electrical communication between those components. Electrical communication is established using at least an electrode or probe that is compressed together when the first portion 101 is tightened into the second portion 102.

In order for the device to be reusable, the electrical storage device 30 is rechargeable. The casing 3 contains a charging port 32.

The integrated circuit 4 has a proximal end 4a and a distal end 4b. The positive terminal at the first end 30a of the electrical storage device 30 is in electrical communication with a positive lead of the flexible integrated circuit 4. The negative terminal at the second end 30b of the electrical storage device 30 is in electrical communication with a negative lead of the integrated circuit 4. The distal end 4b of the integrated circuit 4 comprises a microprocessor. The microprocessor is configured to process data from a sensor, to control a light, to direct current flow to means of ultrasonic vibrations 5 in the second portion 102, and to terminate current flow after a pre-programmed amount of time.

The sensor detects when the ultrasonic mist inhaler 100 is in use (when the user draws on the inhaler) and activates the microprocessor. The sensor can be selected to detect changes in pressure, air flow, or vibration. In one arrangement, the sensor is a pressure sensor. In the digital device, the sensor takes continuous readings which in turn requires the digital sensor to continuously draw current, but the amount is small and overall battery life would be negligibly affected.

In some arrangements, the integrated circuit 4 comprises a H bridge, which may be formed by 4 MOSFETs to convert a direct current into an alternate current at high frequency.

Referring to FIG. 2 and FIG. 3, illustrations of a liquid reservoir structure 2 according to an arrangement are shown. The liquid reservoir structure 2 comprises a liquid chamber 21 adapted to receive liquid to be atomized and a sonication chamber 22 in fluid communication with the liquid chamber 21.

In the arrangement shown, the liquid reservoir structure 2 comprises an inhalation channel 20 providing an air passage from the sonication chamber 22 toward the surroundings.

As an arrangement of sensor position, the sensor may be located in the sonication chamber 22.

The inhalation channel 20 has a frustoconica element 20*a* and an inner container 20*b*.

As depicted in FIGS. 4A and 4B, further the inhalation channel 20 has an airflow member 27 for providing air flow from the surroundings to the sonication chamber 22.

The airflow member 27 has an airflow bridge 27*a* and an airflow duct 27*b* made in one piece, the airflow bridge 27*a* having two airway openings 27*a*' forming a portion of the inhalation channel 20 and the airflow duct 27*b* extending in the sonication chamber 22 from the airflow bridge 27*a* for providing the air flow from the surroundings to the sonication chamber.

The airflow bridge 27*a* cooperates with the frustoconical element 20*a* at the second diameter 20*a*2.

The airflow bridge 27*a* has two opposite peripheral openings 27*a*" providing air flow to the airflow duct 27*b*.

The cooperation with the airflow bridge 27*a* and the frustoconical element 20*a* is arranged so that the two opposite peripheral openings 27*a*" cooperate with complementary openings 20*a*" in the frustoconical element 20*a*.

The mouthpiece 1 and the frustoconical element 20*a* are radially spaced and an airflow chamber 28 is arranged between them.

As depicted in FIGS. 1 and 2, the mouthpiece 1 has two opposite peripheral openings 1".

The peripheral openings 27*a*", 20*a*", 1" of the airflow bridge 27*a*, the frustoconical element 20*a* and the mouthpiece 1 directly supply maximum air flow to the sonication chamber 22.

The frustoconical element 20*a* includes an internal passage, aligned in the similar direction as the inhalation channel 20, having a first diameter 20*a*1 less than that of a second diameter 20*a*2, such that the internal passage reduces in diameter over the frustoconical element 20*a*.

The frustoconical element 20*a* is positioned in alignment with the means of ultrasonic vibrations 5 and a capillary element 7, wherein the first diameter 20*a*1 is linked to an inner duct 11 of the mouthpiece 1 and the second diameter 20*a*2 is linked to the inner container 20*b*.

The inner container 20*b* has an inner wall delimiting the sonication chamber 22 and the liquid chamber 21.

The liquid reservoir structure 2 has an outer container 20*c* delimiting the outer wall of the liquid chamber 21.

The inner container 20*b* and the outer container 20*c* are respectively the inner wall and the outer wall of the liquid chamber 21.

The liquid reservoir structure 2 is arranged between the mouthpiece 1 and the casing 3 and is detachable from the mouthpiece 1 and the casing 3.

The liquid reservoir structure 2 and the mouthpiece 1 or the casing 3 may include complimentary arrangements for engaging with one another; further such complimentary arrangements may include one of the following: a bayonet type arrangement; a threaded engaged type arrangement; a magnetic arrangement; or a friction fit arrangement; wherein the liquid reservoir structure 2 includes a portion of the arrangement and the mouthpiece 1 or the casing 3 includes the complimentary portion of the arrangement.

In the reusable arrangement, the components are substantially the same. The differences in the reusable arrangement vis-a-vis the disposable arrangement are the accommodations made to replace the liquid reservoir structure 2.

Figure 3:
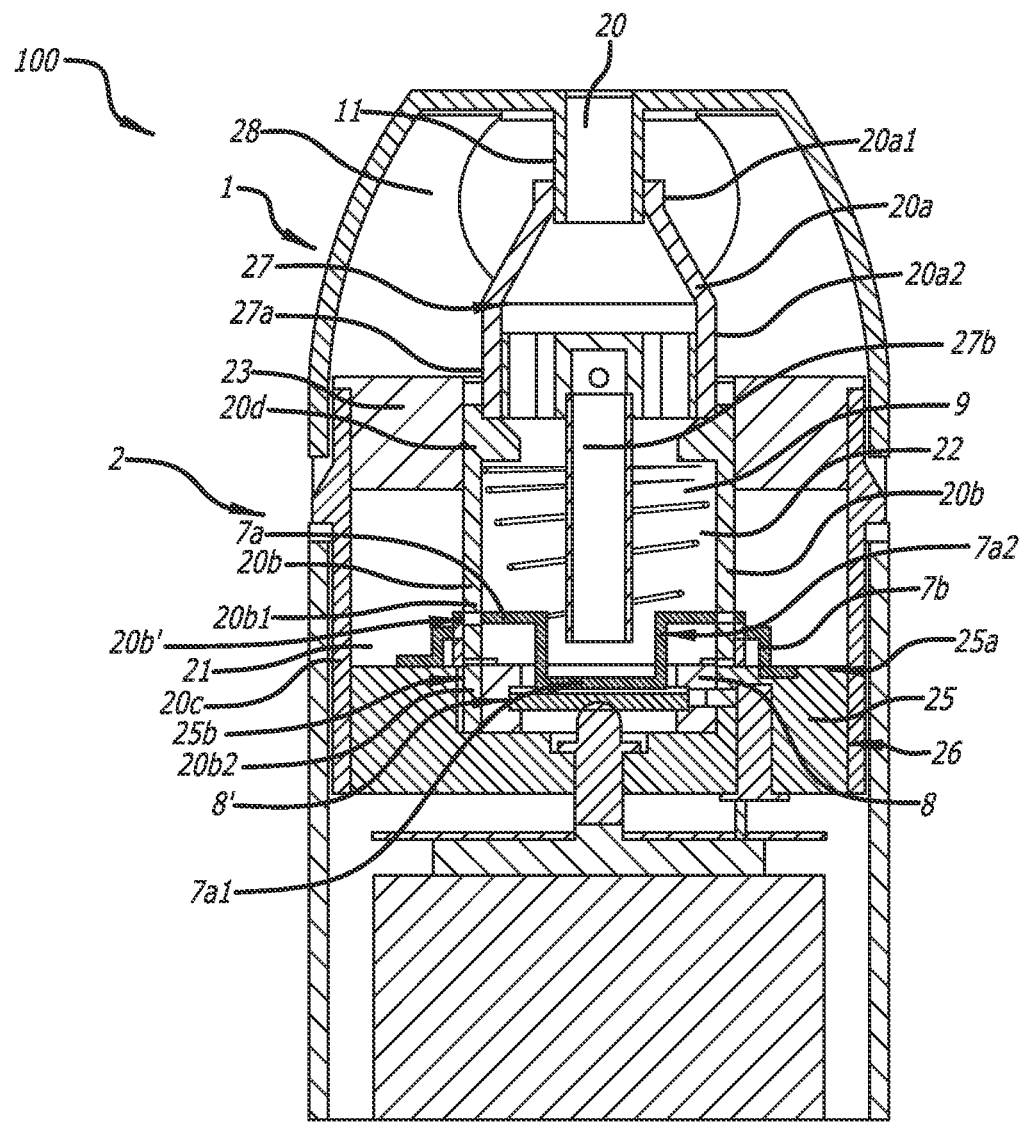
FIG. 3 is a cross section view of components of an inhaler liquid reservoir structure.
Figure 5:
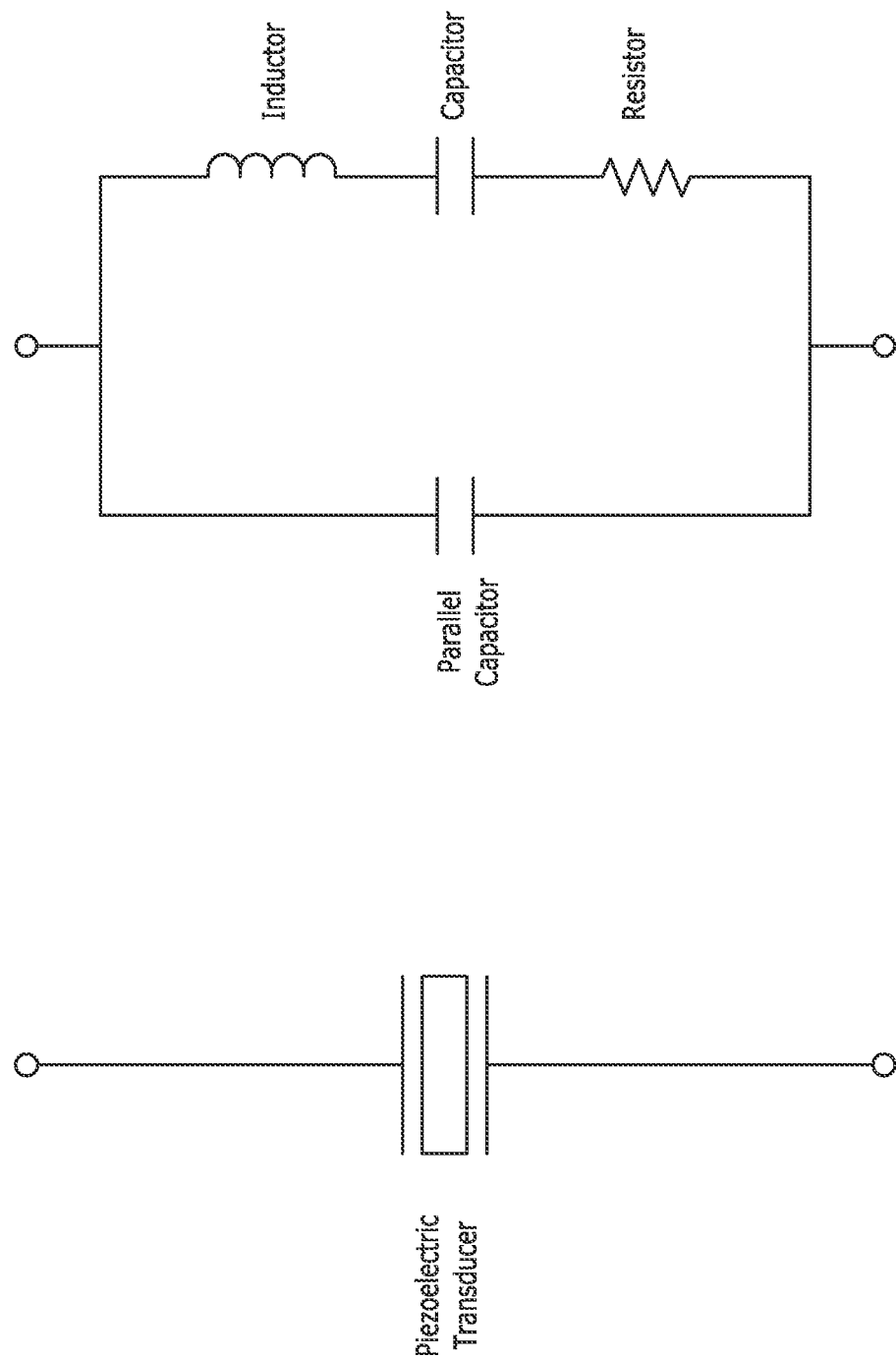
FIG. 5 is schematic diagram showing a piezoelectric transducer modelled as an RLC circuit.
Figure 6:
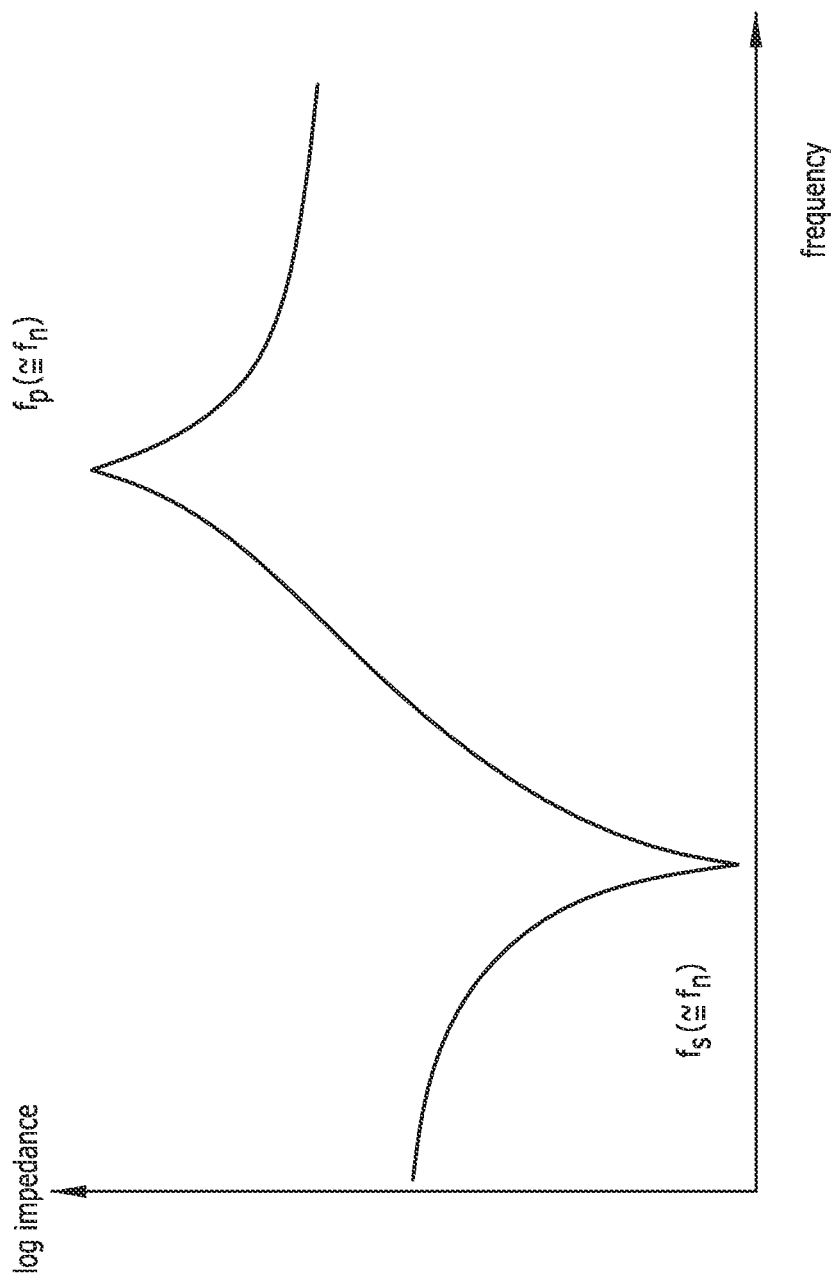
FIG. 6 is graph of frequency versus log impedance of an RLC circuit.
Figure 7:
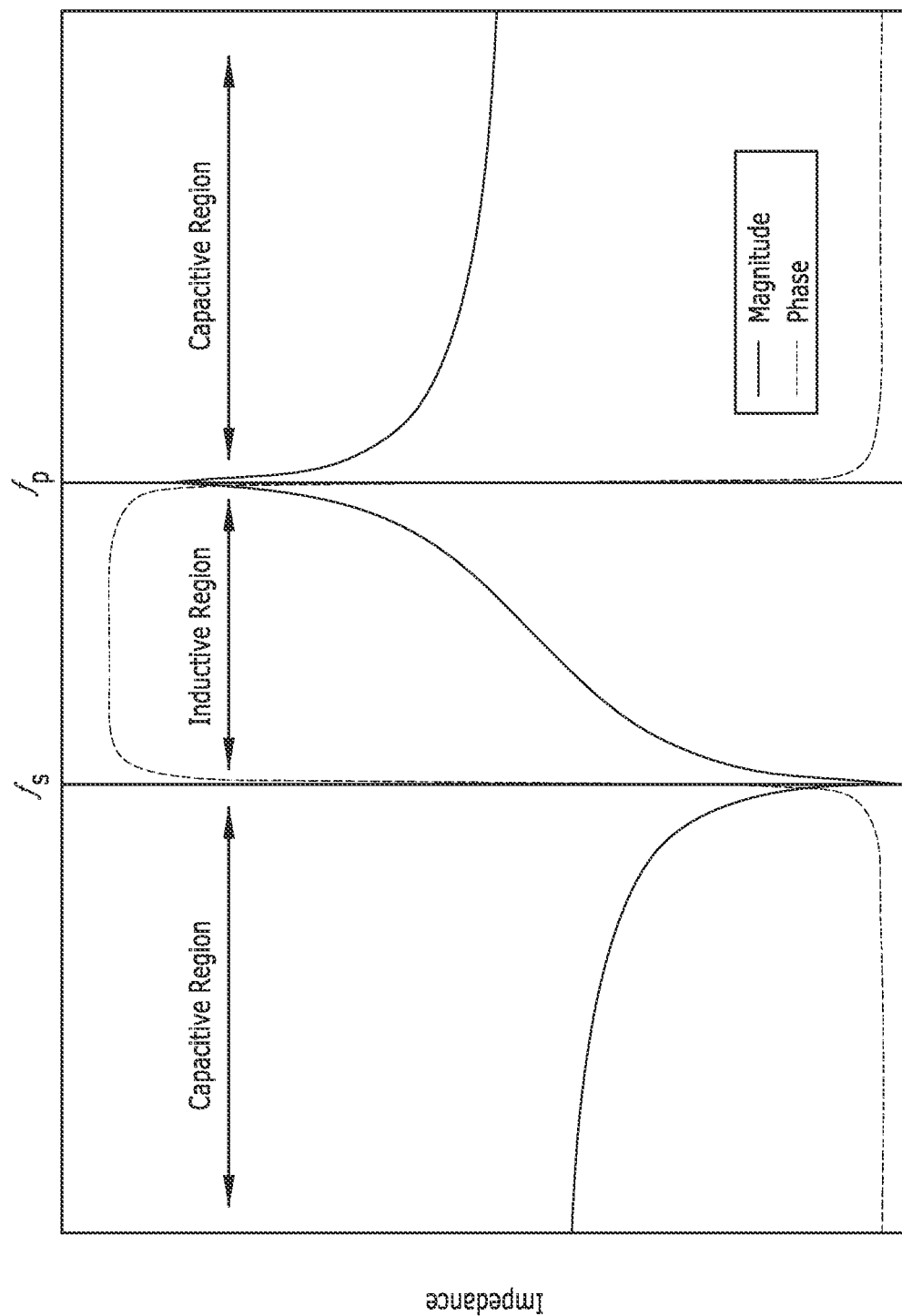
FIG. 7 is graph of frequency versus log impedance showing inductive and capacitive regions of operation of a piezoelectric transducer.
Figure 8:
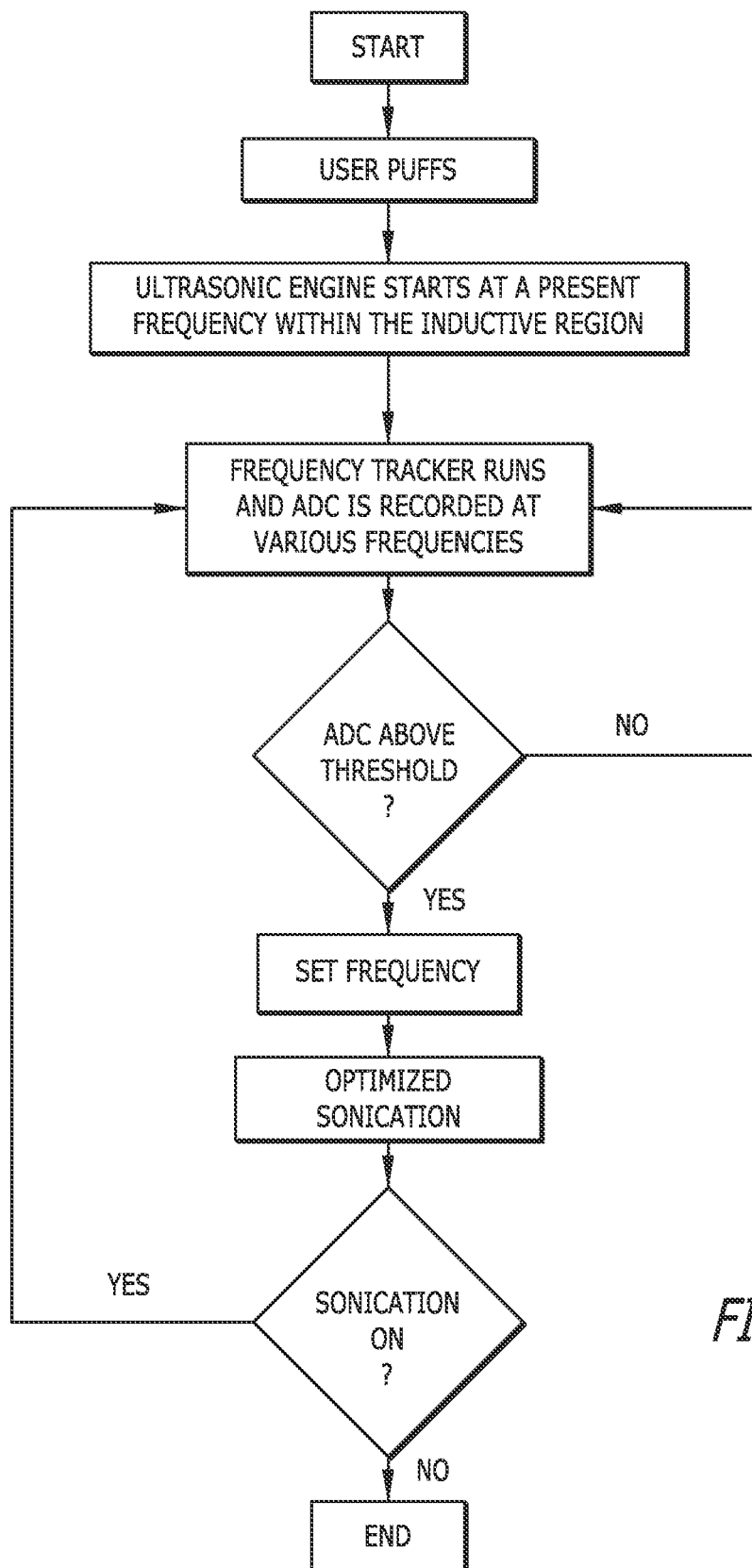
FIG. 8 is flow diagram showing the operation of a frequency controller.
Figure 9:
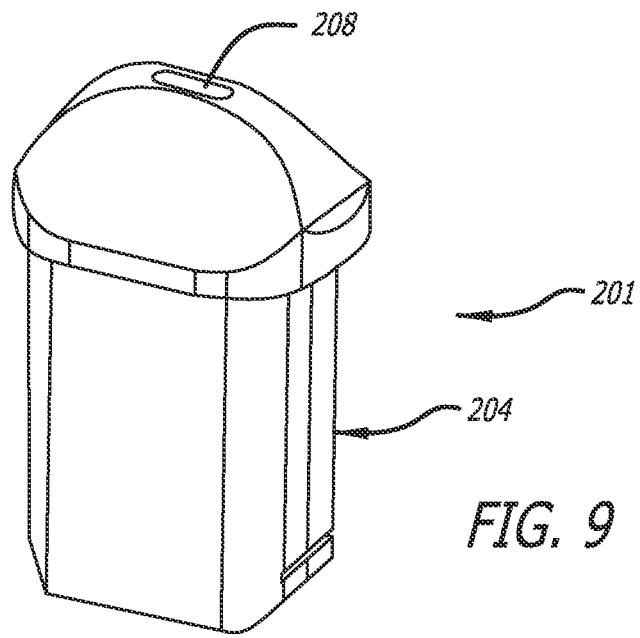
FIG. 9 is a diagrammatic perspective view of a mist generator device of this disclosure.
Figure 10:
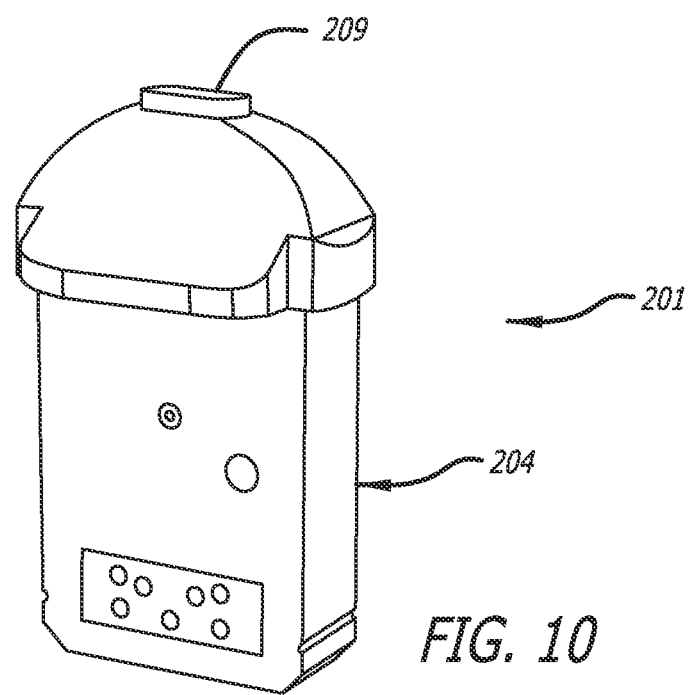
FIG. 10 is a diagrammatic perspective view of a mist generator device of this disclosure.

As shown in FIG. 3, the liquid chamber 21 has a top wall 23 and a bottom wall 25 closing the inner container 20*b* and the outer container 20*c* of the liquid chamber 21.

The capillary element 7 is arranged between a first section 20*b*1 and a second section 20*b*2 of the inner container 20*b*.

The capillary element 7 has a flat shape extending from the sonication chamber to the liquid chamber.

Figure 2:
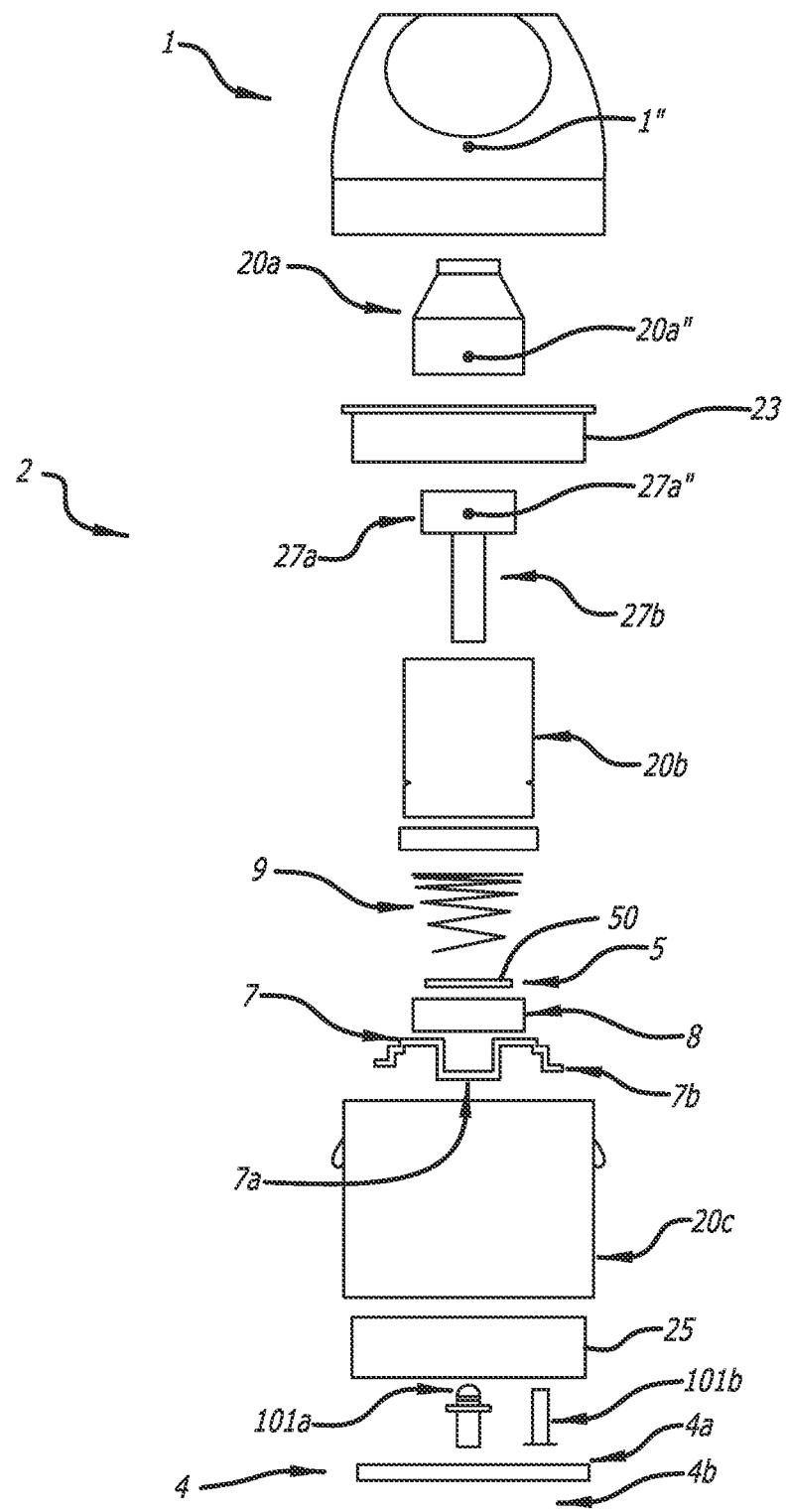
FIG. 2 is an exploded view of components of an inhaler liquid reservoir structure.

As depicted in FIG. 2 or 3, the capillary element 7 comprises a central portion 7*a* in U-shape and a peripheral portion 7*b* in L-shape.

The L-shape portion 7*b* extends into the liquid chamber 21 on the inner container 20*b* and along the bottom wall 25.

The U-shape portion 7*a* is contained into the sonication chamber 21. The U-shape portion 7*a* on the inner container 20*b* and along the bottom wall 25.

In the ultrasonic mist inhaler, the U-shape portion 7*a* has an inner portion 7*a*1 and an outer portion 7*a*2, the inner portion 7*a*1 being in surface contact with an atomization surface 50 of the means of ultrasonic vibrations 5 and the outer portion 7*a*2 being not in surface contact with the means of ultrasonic vibrations 5.

The bottom wall 25 of the liquid chamber 21 is a bottom plate 25 closing the liquid chamber 21 and the sonication chamber 22. The bottom plate 25 is sealed, thus preventing leakage of liquid from the sonication chamber 22 to the casing 3.

The bottom plate 25 has an upper surface 25*a* having a recess 25*b* on which is inserted an elastic member 8. The means of ultrasonic vibrations 5 are supported by the elastic member 8. The elastic member 8 is formed from an annular plate-shaped rubber having an inner hole 8' wherein a groove is designed for maintaining the means of ultrasonic vibrations 5.

The top wall 23 of the liquid chamber 21 is a cap 23 closing the liquid chamber 23.

The top wall 23 has a top surface 23 representing the maximum level of the liquid that the liquid chamber 21 may contain and the bottom surface 25 representing the minimum level of the liquid in the liquid chamber 21.

The top wall 23 is sealed, thus preventing leakage of liquid from the liquid chamber 21 to the mouthpiece 1.

The top wall 23 and the bottom wall 25 are fixed to the liquid reservoir structure 2 by means of fixation such as screws, glue or friction.

As depicted in FIG. 3, the elastic member is in line contact with the means of ultrasonic vibrations 5 and prevents contact between the means of ultrasonic vibrations 5 and the inhaler walls, suppression of vibrations of the liquid reservoir structure are more effectively prevented. Thus, fine particles of the liquid atomized by the atomizing member can be sprayed farther.

As depicted in FIG. 3, the inner container 20*b* has openings 20*b*' between the first section 20*b*1 and the second section 20*b*2 from which the capillary element 7 is extending from the sonication chamber 21, The capillary element 7 absorbs liquid from the liquid chamber 21 through the apertures 20*b*'. The capillary element 7 is a wick. The capillary element 7 transports liquid to the sonication chamber 22 via capillary action. In some arrangements, the capillary element 7 is made of bamboo fibers. In some arrangements, the capillary element 7 may be of a thickness between 0.27 mm and 0.32 mm and have a density between 38 $g/m^2$ and 48 $g/m^2$.

As can be seen in FIG. 3, the means of ultrasonic vibrations 5 are disposed directly below the capillary element 7.

The means of ultrasonic vibrations 5 may be an ultrasonic transducer. For arrangement, the means of ultrasonic vibrations 5 may be a piezoelectric transducer, which may be designed in a circular plate-shape. The material of the piezoelectric transducer may be ceramic.

A variety of transducer materials can also be used for the means of ultrasonic vibrations 5.

The end of the airflow duct 27*b*1 faces the means of ultrasonic vibrations 5, The means of ultrasonic vibrations 5 are in electrical communication with electrical contactors 101*a*, 101*b*. It is noted that, the distal end 4*b* of the integrated circuit 4 has an inner electrode and an outer electrode. The inner electrode contacts the first electrical contact 101*a* which is a spring contact probe, and the outer electrode contacts the second electrical contact 101*b* which is a side pin. Via the integrated circuit 4, the first electrical contact 101*a* is in electrical communication with the positive terminal of the electrical storage device 30 by way of the microprocessor, while the second electrical contact 101*b* is in electrical communication with the negative terminal of the electrical storage device 30.

The electrical contacts 101*a*, 101*b* crossed the bottom plate 25. The bottom plate 25 is designed to be received inside the perimeter wall 26 of the liquid reservoir structure 2. The bottom plate 25 rests on complementary ridges, thereby creating the liquid chamber 21 and sonication chamber 22.

The inner container 20*b* comprises a circular inner slot 20*d* on which a mechanical spring is applied.

By pushing the central portion 7*a*1 onto the means of ultrasonic vibrations 5, the mechanical spring 9 ensures a contact surface between them.

The liquid reservoir structure 2 and the bottom plate 25 can be made using a variety of thermoplastic materials.

When the user draws on the ultrasonic mist inhaler 100, an air flow is drawn from the peripheral openings and penetrates the airflow chamber 28, passes the peripheral openings 27*a*" of the airflow bridge 27*a* and the frustoconical element 20*a* and flows down into the sonication chamber 22 via the airflow duct 27*b* directly onto the capillary element 7. At the same time, the liquid is drawn from the reservoir chamber 21 by capillarity, through the plurality of apertures 20*b*', and into the capillary element 7. The capillary element 7 brings the liquid into contact with the means of ultrasonic vibrations 5 of the inhaler 100. The user's draw also causes the pressure sensor to activate the integrated circuit 4, which directs current to the means of ultrasonic vibrations 5. Thus, when the user draws on the mouthpiece 1 of the inhaler 100, two actions happen at the same time. Firstly, the sensor activates the integrated circuit 4, which triggers the means of ultrasonic vibrations 5 to begin vibrating. Secondly, the draw reduces the pressure outside the reservoir chamber 21 such that flow of the liquid through the apertures 20*b*' begins, which saturates the capillary element 7. The capillary element 7 transports the liquid to the means of ultrasonic vibrations 5, which causes bubbles to form in a capillary channel by the means of ultrasonic vibrations 5 and mist the liquid. Then, the mist liquid is drawn by the user.

In some arrangements, the integrated circuit 4 comprises a frequency controller which is configured to control the frequency at which the means of ultrasonic vibrations 5 operates. The frequency controller comprises a processor and a memory, the memory storing executable instructions which, when executed by the processor, cause the processor to perform at least one function of the frequency controller.

As described above, in some arrangements the ultrasonic mist inhaler 100 drives the means of ultrasonic vibrations 5 with a signal having a frequency of 2.8 MHz to 8.2 MHz in order to vaporize a liquid having a liquid viscosity of 1.05 Pa·s to 1.412 Pa·s in order to produce a bubble volume of about 0.25 to 0.5 microns. However, for liquids with a different viscosity or for other applications it the means of ultrasonic vibrations 5 may be driven at a different frequency.

For each different application for a mist generation system, there is an optimum frequency or frequency range for driving the means of ultrasonic vibrations 5 in order to optimize the generation of mist. In arrangements where the means of ultrasonic vibrations 5 is a piezoelectric transducer, the optimum frequency or frequency range will depend on at least the following four parameters:

1. Transducer Manufacturing Processes

In some arrangements, the means of ultrasonic vibrations 5 comprises a piezoelectric ceramic. The piezoelectric ceramic is manufactured by mixing compounds to make a ceramic dough and this mixing process may not be consistent throughout production. This inconsistency can give rise to a range of different resonant frequencies of the cured piezoelectric ceramic.

If the resonant frequency of the piezoelectric ceramic does not correspond to the required frequency of operation of the device then no mist is produced during the operation of the device. In the case of a nicotine mist inhaler, even a slight offset in the resonant frequency of the piezoelectric ceramic is enough to impact the production of mist, meaning that the device will not deliver adequate nicotine levels to the user.

2. Load on Transducer

During operation, any changes in the load on the piezoelectric transducer will inhibit the overall displacement of the oscillation of the piezoelectric transducer. To achieve optimal displacement of the oscillation of the piezoelectric transducer, the drive frequency must be adjusted to enable the circuit to provide adequate power for maximum displacement.

The types of loads that can affect the oscillator's efficiency can include the amount of liquid on the transducer (dampness of the wicking material), and the spring force applied to the wicking material to keep permanent contact with the transducer. It may also include the means of electrical connection.

3. Temperature

Ultrasonic oscillations of the piezoelectric transducer are partially damped by its assembly in a device. This may include the transducer being placed in a silicone/rubber ring, and the spring exerting pressure onto the wicking material that is above the transducer. This dampening of the oscillations causes rise in local temperatures on and around the transducer.

An increase in temperature affects the oscillation due to changes in the molecular behavior of the transducer. An increase in the temperature means more energy to the molecules of the ceramic, which temporarily affects its crystalline structure. Although the effect is reversed as the temperature reduces, a modulation in supplied frequency is required to maintain optimal oscillation. This modulation of frequency cannot be achieved with a conventional fixed frequency device.

An increase in temperature also reduces the viscosity of the solution (e-liquid) which is being vaporized, which may require an alteration to the drive frequency to induce cavitation and maintain continuous mist production. In the case of a conventional fixed frequency device, a reduction in the viscosity of the liquid without any change in the drive frequency will reduce or completely stop mist production, rendering the device inoperable.

4. Distance to Power Source

The oscillation frequency of the electronic circuit can change depending on the wire-lengths between the transducer and the oscillator-driver. The frequency of the electronic circuit is inversely proportional to the distance between the transducer and the remaining circuit.

Although the distance parameter is primarily fixed in a device, it can vary during the manufacturing process of the device, reducing the overall efficiency of the device. Therefore, it is desirable to modify the drive frequency of the device to compensate for the variations and optimize the efficiency of the device.

A piezoelectric transducer can be modelled as an RLC circuit in an electronic circuit, as shown in FIG. 5. The four parameters described above may be modelled as alterations to the overall inductance, capacitance, and/or resistance of the RLC circuit, changing the resonance frequency range supplied to the transducer. As the frequency of the circuit increases to around the resonance point of the transducer, the log Impedance of the overall circuit dips to a minimum and then rises to a maximum before settling to a median range.

FIG. 6 shows a generic graph explaining the change in overall impedance with increase in frequency in an RLC circuit. FIG. 7 shows how a piezoelectric transducer acts as a capacitor in a first capacitive region at frequencies below a first predetermined frequency $f_s$ and in a second capacitive region at frequencies above a second predetermined frequency $f_p$. The piezoelectric transducer acts as an inductor in an inductive region at frequencies between the first and second predetermined frequencies $f_s$, $f_p$. In order to maintain optimal oscillation of the transducer and hence maximum efficiency, the current flowing through the transducer must be maintained at a frequency within the inductive region.

The frequency controller of the device of some arrangements is configured to maintain the frequency of oscillation of the piezoelectric transducer (the means of ultrasonic vibrations 5) within the inductive region, in order to maximize the efficiency of the device.

The frequency controller is configured to perform a sweep operation in which the frequency controller drives the transducer at frequencies which track progressively across a predetermined sweep frequency range. As the frequency controller performs the sweep, the frequency controller monitors an Analog-to-Digital Conversion (ADC) value of an Analog-to-Digital converter which is coupled to the transducer. In some arrangements the ADC value is a parameter of the ADC which is proportional to the voltage across the transducer. In other arrangements, the ADC value is a parameter of the ADC which is proportional to the current flowing through the transducer.

As will be described in more detail below, the frequency controller of some arrangements determines the active power being used by the ultrasonic transducer by monitoring the current flowing through the transducer.

During the sweep operation, the frequency controller locates the inductive region of the frequency for the transducer. Once the frequency controller has identified the inductive region, the frequency controller records the ADC value and locks the drive frequency of the transducer at a frequency within the inductive region (i.e. between the first and second predetermined frequencies $f_s$, $f_p$) in order to optimize the ultrasonic cavitation by the transducer. When the drive frequency is locked within the inductive region, the electro-mechanical coupling factor of the transducer is maximized, thereby maximizing the efficiency of the device.

In some arrangements, the frequency controller is configured to perform the sweep operation to locate the inductive region each time the oscillation is started or re-started. In the arrangements, the frequency controller is configured to lock the drive frequency at a new frequency within the inductive region each time the oscillation is started and thereby compensate for any changes in the parameters that affect the efficiency of operation of the device.

In some arrangements, the frequency controller ensures optimal mist production and maximizes efficiency of medication delivery to the user. In some arrangements, the frequency controller optimizes the device and improves the efficiency and maximizes nicotine delivery to the user.

In other arrangements, the frequency controller optimizes the device and improves the efficiency of any other device which uses ultrasound. In some arrangements, the frequency controller is configured for use with ultrasound technology for therapeutic applications in order to extend the enhancement of drug release from an ultrasound-responsive drug delivery system. Having precise, optimal frequency during operation, ensures that the microbubbles, nanobubbles, nanodroplets, liposome, emulsions, micelles or any other delivery systems are highly effective.

In some arrangements, in order to ensure optimal mist generation and optimal delivery of compounds as described above, the frequency controller is configured to operate in a recursive mode. When the frequency controller operates in the recursive mode, the frequency controller runs the sweep of frequencies periodically during the operation of the device and monitors the ADC value to determine if the ADC value is above a predetermined threshold which is indicative of optimal oscillation of the transducer.

In some arrangements, the frequency controller runs the sweep operation while the device is in the process of aerosolizing liquid in case the frequency controller is able to identify a possible better frequency for the transducer. If the frequency controller identifies a better frequency, the frequency controller locks the drive frequency at the newly identified better frequency in order to maintain optimal operation of the device.

In some arrangements, the frequency controller runs the sweep of frequencies for a predetermined duration periodically during the operation of the device. In the case of the device of the arrangements described above, the predetermined duration of the sweep and the time period between sweeps are selected to optimize the functionality of the device. When implemented in an ultrasonic mist inhaler device, this will ensure an optimum delivery to a user throughout the user's inhalation.

FIG. 8 shows a flow diagram of the operation of the frequency controller of some arrangements.

The following disclosure discloses further arrangements of mist generator devices which comprise many of the same elements as the arrangements described above, Elements of the arrangements described above may be interchanged with any of the elements of the arrangements described in the remaining part of this disclosure.

The mist generator devices described below are used with or are for use with a hookah device 202 which is also described below. In other arrangements, the hookah device 202 comprises a plurality of other mist generator devices instead of the mist generator device 201 described herein.

To ensure adequate aerosol production, the mist generator device 201 of some arrangements comprises an ultrasonic/piezoelectric transducer of exactly or substantially 16 mm diameter. This transducer is manufactured to specific capacitance and impedance values to control the frequency and power required for desired aerosol volume production.

A horizontally placed disc-shaped 16 mm diameter ultrasonic transducer would result in a large mist generator device. To minimize the size, the ultrasonic transducer of this arrangement is held vertically in the sonication chamber (the planar surface of the ultrasonic transducer is generally parallel with the flow of aerosol mist and/or generally parallel to the longitudinal length of the mist generator device). Put another way, the ultrasonic transducer is generally perpendicular to a base of the mist generator device.

Referring now to FIGS. 9 to 11 of the accompanying drawings, the mist generator device 201 comprises a mist generator housing 204 which is elongate and optionally formed from two housing portions 205, 206 which are attached to one another. The mist generator housing 204 comprises an air inlet port 207 and a mist outlet port 208.

In this arrangement, the mist generator housing 204 is of injection molded plastic, specifically polypropylene that is typically used for medical applications. In this arrangement, the mist generator housing 204 is of a heterophasic copolymer. More particularly a BF970MO heterophasic copolymer, which has an optimum combination of very high stiffness and high impact strength. The mist generator housing parts molded with this material exhibit good anti-static performance.

A heterophasic copolymer such as polypropylene is particularly suitable for the mist generator housing 204 since this material does not cause condensation of the aerosol as it flows from the sonication chamber 219 through the mist outlet port 208. This plastic material can also be directly recycled easily using industrial shredding and cleaning processes.

In FIG. 10, the mist outlet port 208 is closed by a closure element 209. However, it is to be appreciated that when the mist inhaler device 200 is in use, the closure element 209 is removed from the mist outlet port 208, as shown in FIG. 9.

Referring now to FIGS. 12 and 13, the mist generator device 200 comprises a transducer holder 210 which is held within the mist generator housing 204. The transducer holder 210 comprises a body portion 211 which, in this arrangement, is cylindrical or generally cylindrical in shape with circular upper and lower openings 212, 213. The transducer holder 210 is provided with an internal channel 214 for receiving an edge of an ultrasonic transducer 215, as shown in FIG. 13.

The transducer holder 210 incorporates a cutaway section 216 through which an electrode 217 extends from the ultrasonic transducer 215 so that the electrode 217 may be connected electrically to an AC driver of the hookah device 202, as described in more detail below.

Figure 11:
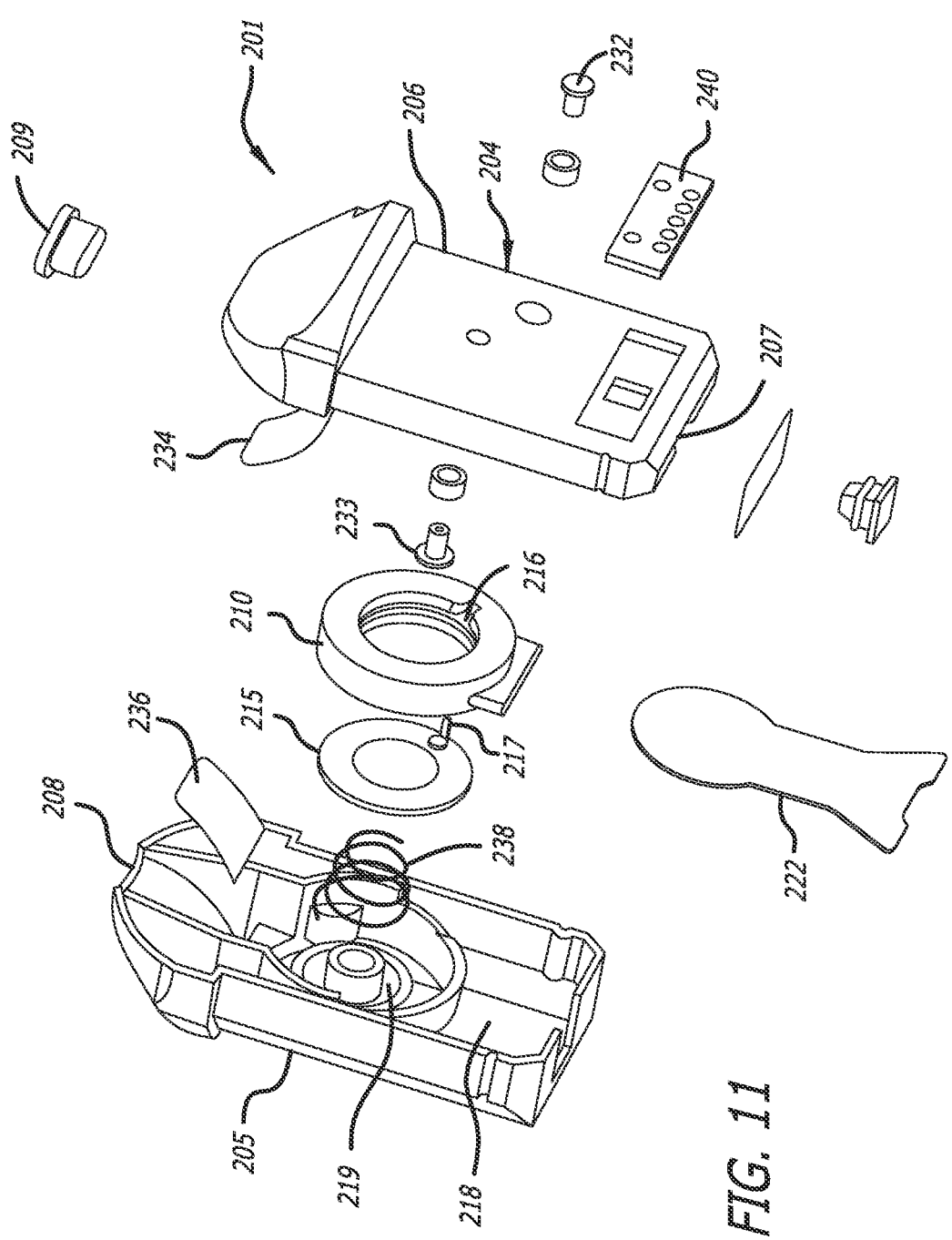
FIG. 11 is a diagrammatic exploded perspective view of a mist generator device of this disclosure.
Figure 12:
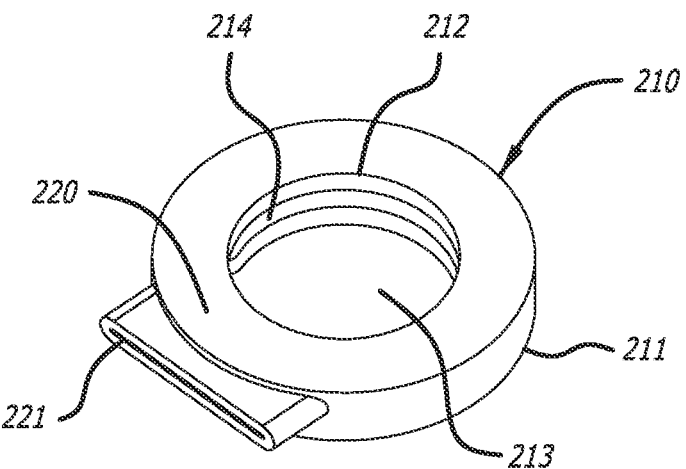
FIG. 12 is a diagrammatic perspective view of a transducer holder of this disclosure.
Figure 13:
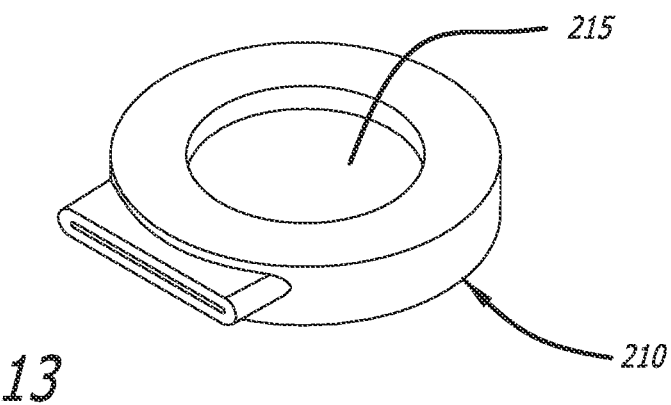
FIG. 13 is a diagrammatic perspective view of a transducer holder of this disclosure.

Referring again to FIG. 11, the mist generator device 201 comprises a liquid chamber 218 which is provided within the mist generator housing 204. The liquid chamber 218 is for containing a liquid to be atomized. In some arrangements, a liquid is contained in the liquid chamber 218. In other arrangements, the liquid chamber 218 is empty initially and the liquid chamber is filled with a liquid subsequently.

A liquid (also referred to herein as an e-liquid) composition suitable for use in an ultrasonic mist generator device 201 of some arrangements consists of a nicotine salt consisting of nicotine levulinate wherein:

The relative amount of vegetable glycerin in the composition is: from 55 to 80% (w/w), or from 60 to 80% (w/w), or from 65 to 75% (w/w), or 70% (w/w); and/or, The relative amount of propylene glycol in the composition is: from 5 to 30% (w/w), or from 10 to 30% (w/w), or from 15 to 25% (w/w), or 20% (w/w); and/or, The relative amount of water in the composition is: from 5 to 15% (wlw), or from 7 to 12% (w/w), or 10% (w/w); and/or, The amount of nicotine and/or nicotine salt in the composition is: from 0.1 to 80 mg/ml, or from 0.1 to 50 mg/ml, or from 1 to 25 mg/ml, or from 10 to 20 mg/ml, or 17 mg/ml.

In some arrangements, the mist generator device 201 contains an e-liquid having a kinematic viscosity between 1.05 Pa·s and 1.412 Pa·s.

In some arrangements, the liquid chamber 218 contains a liquid comprising a nicotine levulinate salt at a 1:1 molar ratio.

In some arrangements, the liquid chamber 218 contains an e-liquid comprising nicotine, propylene glycol, vegetable glycerin, water and flavorings. In some examples, the % concentration of each component in the e-liquid is shown below in Table 1, Table 2, Table 3 or Table 4.

TABLE 1

The % concentration of each component in the e-liquid (e-liquid 1).

| Component | % (w/w) |
| --- | --- |
| Propylene glycol | 15.1 |
| Vegetable glycerin | 70 |
| Water | 10 |
| Nicotine | 1.7 |
| Levulinic acid | 0.2 |
| Flavorings | 3 |

TABLE 2

The % concentration of each component in the e-liquid (e-liquid 2). (Approximately, 2:1 molar ratio of levulinic acid to nicotine.)

| Component | % (w/w) |
| --- | --- |
| Propylene glycol | 12.87 |
| Vegetable glycerin | 70 |
| Water | 10 |
| Nicotine | 1.7 |
| Levulinic acid | 2.43 |
| Flavorings | 3 |

TABLE 3

The % concentration of each component in the e-liquid (e-liquid 3). (Approximately, 1:1 molar ratio of levulinic acid to nicotine.)

| Component | % (w/w) |
| --- | --- |
| Propylene glycol | 14.08 |
| Vegetable glycerin | 70 |
| Water | 10 |
| Nicotine | 1.7 |
| Levulinic acid | 1.22 |
| Flavorings | 3 |

TABLE 4

The % concentration of each component in the e-liquid (e-liquid 4). (Approximately, 3:1 molar ratio of levulinic acid to nicotine.)

| Component | % (w/w) |
| --- | --- |
| Propylene glycol | 11.64 |
| Vegetable glycerin | 70 |
| Water | 10 |
| Nicotine | 1.7 |
| Levulinic acid | 3.66 |
| Flavorings | 3 |

In the non-limiting examples, the nicotine in solution is all or part in the form of nicotine levulinate.

The nicotine levulinate salt is formed by combining nicotine and levulinic acid in solution. This results in the formation of the salt nicotine levulinate, which comprises a levulinate anion and a nicotine cation.

The % concentration of nicotine in the e-liquid shown in Table 1 Table 2, Table 3 and Table 4 is approximately equivalent to 17 mg/ml.

In some arrangements, the liquid chamber 218 contains a liquid having a kinematic viscosity between 1.05 Pa·s and 1.412 Pa·s and a liquid density between 1.1 g/ml and 1.3 g/ml.

In some arrangements, the liquid within the liquid chamber 218 comprises a flavoring (e.g. a fruit flavor) which is tasted by a user when the user inhales mist generated by the hookah device.

By using an e-liquid with the correct parameters of viscosity, density and having a desired target bubble volume of liquid spray into the air, it has been found that the frequency range of 2.8 MHz to 3.2 MHz for liquid viscosity range of 1.05 Pa·s and 1.412 Pa·s and density of approximately 1.1-1.3 g/mL (get density ranges from Hertz) produce a droplet volume where 90% of droplets are below 1 micron and 50% of those are less than 0.5 microns.

The mist generator device 201 comprises a sonication chamber 219 which is provided within the mist generator housing 204.

Returning to FIGS. 12 and 13, the transducer holder 210 comprises a divider portion 220 which provides a barrier between the liquid chamber 218 and the sonication chamber 219. The barrier provided by the divider portion 220 minimizes the risk of the sonication chamber 219 being is flooded with liquid from the liquid chamber 218 or for a capillary element over the ultrasonic transducer 215 becoming oversaturated, either of which would overload and reduce the efficiency of the ultrasonic transducer 215. Moreover, flooding the sonication chamber 219 or over saturating the capillary element could also cause an unpleasant experience with the liquid being sucked in by the user during inhalation. To mitigate this risk, the divider portion 220 of the transducer holder 210 sits as a wall between the sonication chamber 219 and the liquid chamber 218.

The divider portion 220 comprises a capillary aperture 221 which is the only means by which liquid can flow from the liquid chamber 218 to the sonication chamber 219, via a capillary element. In this arrangement, the capillary aperture 221 is an elongate slot having a width of 0.2 mm to 0.4 mm. The dimensions of the capillary aperture 221 are such that the edges of the capillary aperture 221 provide a biasing force which acts on a capillary element extending through the capillary aperture 221 for added control of liquid flow to the sonication chamber 219.

In this arrangement, the transducer holder 210 is of liquid silicone rubber (LSR). In this arrangement, the liquid silicone rubber has a Shore A 60 hardness. This LSR material ensures that the ultrasonic transducer 215 vibrates without the transducer holder 210 dampening the vibrations. In this arrangement, the vibratory displacement of the ultrasonic transducer 215 is 2-5 nanometers and any dampening effect may reduce the efficiency of the ultrasonic transducer 215. Hence, this LSR material and hardness is selected for optimal performance with minimal compromise.

Figure 14:
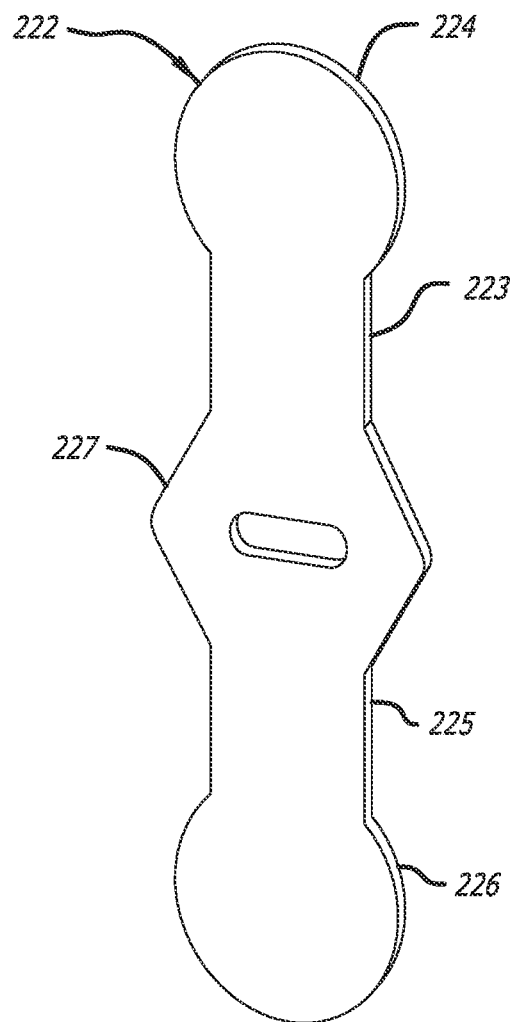
FIG. 14 is a diagrammatic perspective view of a capillary element of this disclosure.
Figure 15:
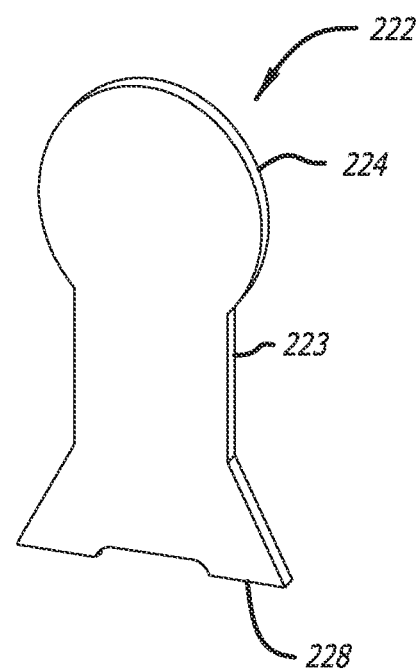
FIG. 15 is a diagrammatic perspective view of a capillary element of this disclosure.

Referring now to FIGS. 14 and 15, the mist generator device 201 comprises a capillary or capillary element 222 for transferring a liquid (containing a drug or other substance) from the liquid chamber 218 to the sonication chamber 219. The capillary element 222 is planar or generally planar with a first portion 223 and a second portion 224. In this arrangement, the first portion 223 has a rectangular or generally rectangular shape and the second portion 224 has a partly circular shape.

In this arrangement, the capillary element 222 comprises a third portion 225 and a fourth portion 226 which are respectively identical in shape to the first and second portions 223, 224. The capillary element 222 of this arrangement is folded about a fold line 227 such that the first and second portions 223, 224 and the third and fourth portions 225, 226 are superimposed on one another, as shown in FIG. 15.

In this arrangement, the capillary element has a thickness of approximately 0.28 mm. When the capillary element 222 is folded to have two layers, as shown in FIG. 15, the overall thickness of the capillary element is approximately 0.56 mm. This double layer also ensures that there is always sufficient liquid on the ultrasonic transducer 215 for optimal aerosol production.

In this arrangement, when the capillary element 222 is folded, the lower end of the first and third parts 223, 225 defines an enlarged lower end 228 which increases the surface area of the capillary element 222 in the portion of the capillary element 222 which sits in liquid within the liquid chamber 218 to maximize the rate at which the capillary element 222 absorbs liquid.

In this arrangement, the capillary element 222 is 100% bamboo fiber. In other arrangements, the capillary element is of at least 75% bamboo fiber. The benefits of using bamboo fiber as the capillary element are as described above.

Figure 16:
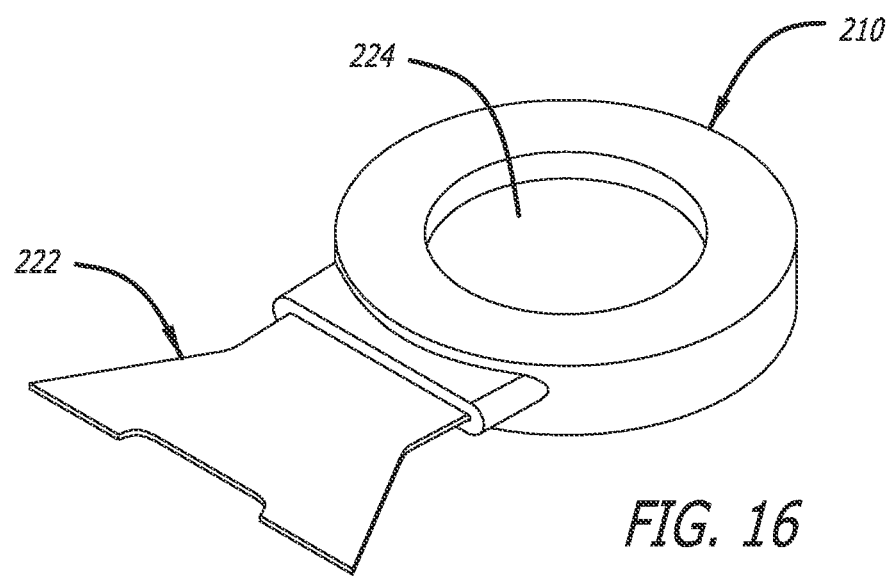
FIG. 16 is a diagrammatic perspective view of a transducer holder of this disclosure.
Figure 17:
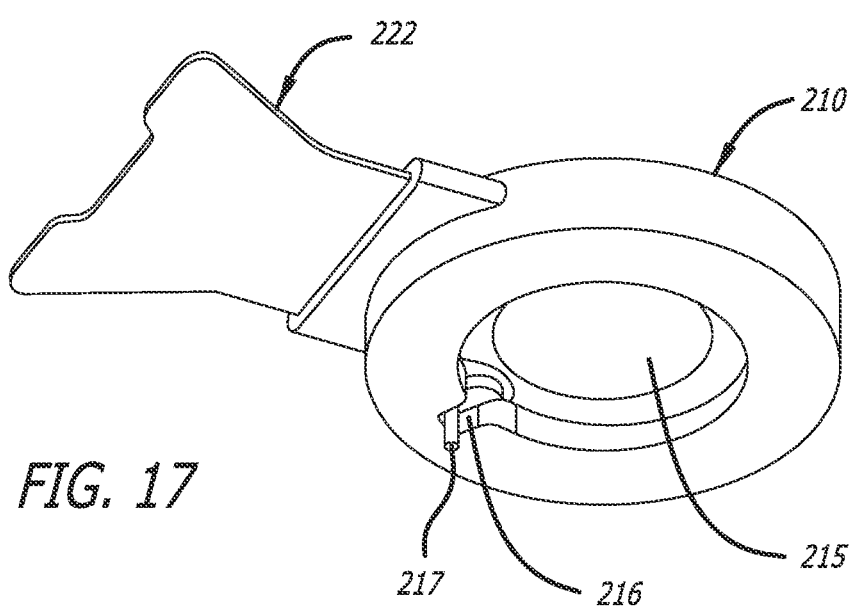
FIG. 17 is a diagrammatic perspective view of a transducer holder of this disclosure.

Referring now to FIGS. 16 and 17, the capillary element 222 is retained by the transducer holder 210 such that the transducer holder 210 retains the second portion 224 of the capillary element 222 superimposed on part of an atomization surface of the ultrasonic transducer 215. In this arrangement, the circular second portion 224 sits within the inner recess 214 of the transducer holder 210.

The first portion 223 of the capillary element 222 extends through the capillary aperture 221 in the transducer holder 210.

Figure 18:
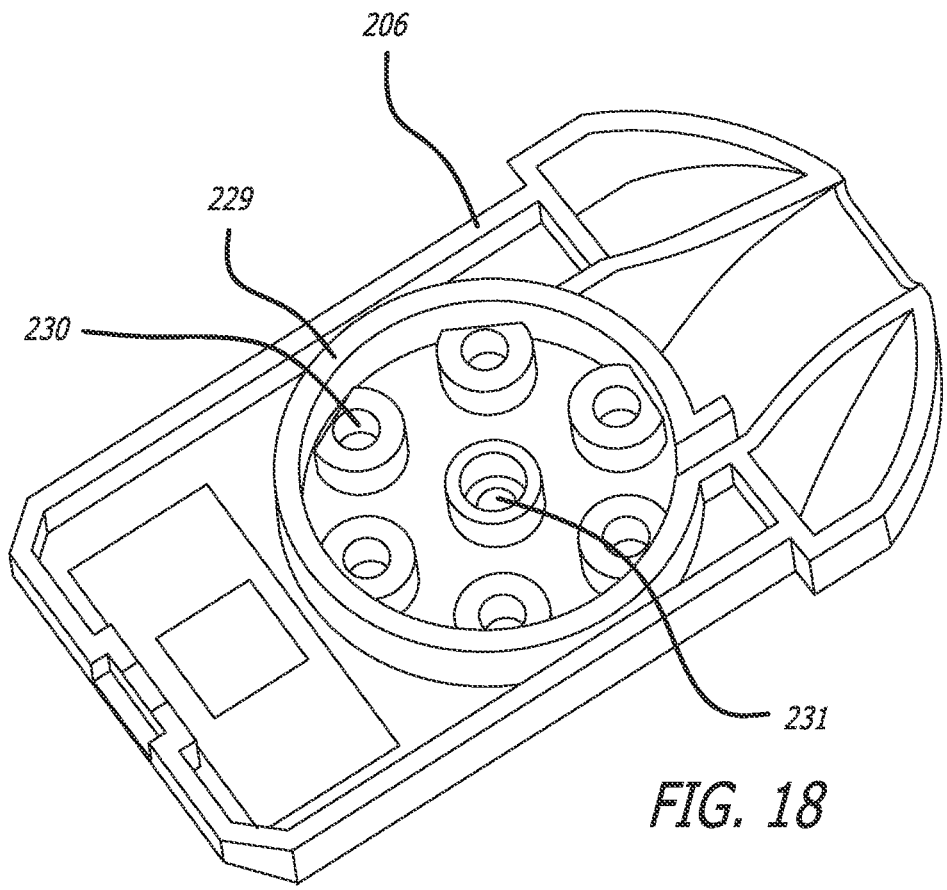
FIG. 18 is a diagrammatic perspective view of a part of a housing of this disclosure.
Figure 19:
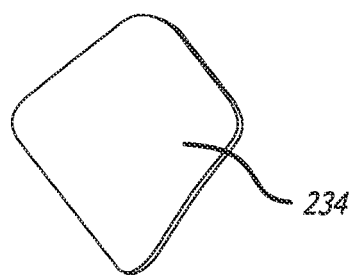
FIG. 19 is a diagrammatic perspective view of an absorbent element of this disclosure.
Figure 20:
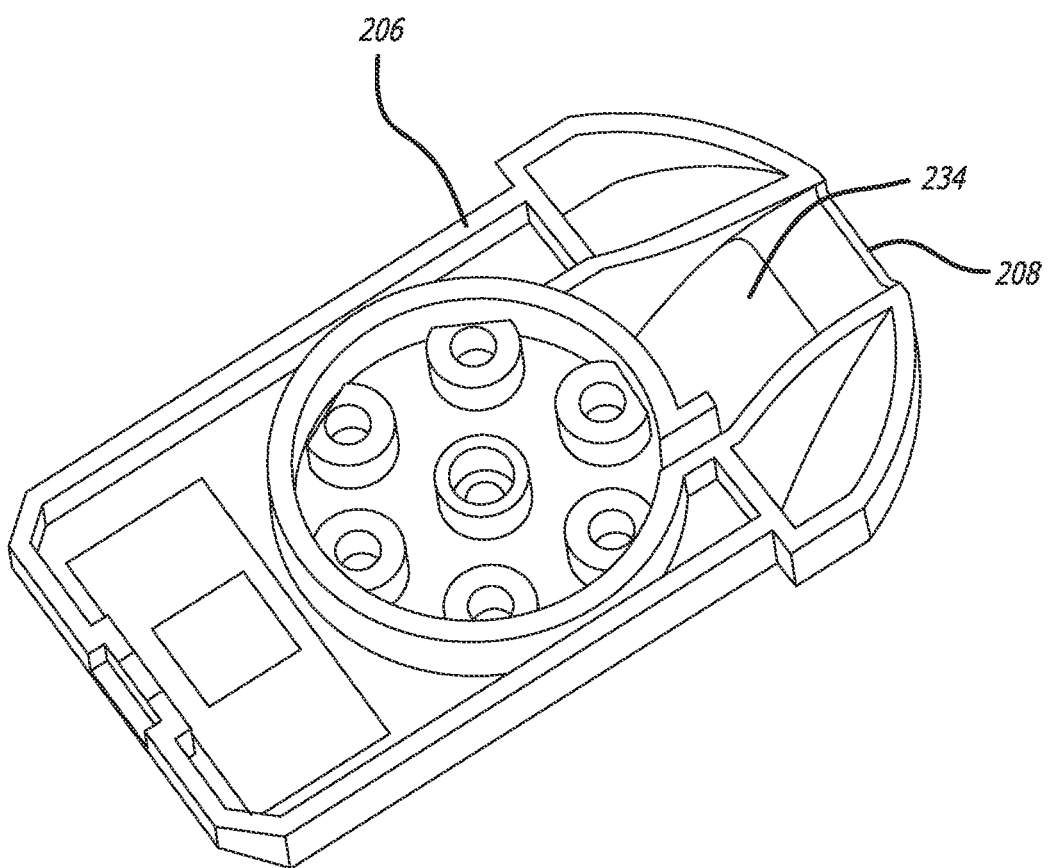
FIG. 20 is a diagrammatic perspective view of a part of a housing of this disclosure.

Referring now to FIGS. 18 to 20, the second portion 206 of the mist generator housing 204 comprises a generally circular wall 229 which receives the transducer holder 222 and forms part of the wall of the sonication chamber 219.

Contact apertures 230 and 231 are provided in a side wall of the second portion 206 for receiving electrical contacts 232 and 233 which form electrical connections with the electrodes of the ultrasonic transducer 215.

In this arrangement, an absorbent tip or absorbent element 234 is provided adjacent the mist outlet port 208 to absorb liquid at the mist outlet port 208. In this arrangement, the absorbent element 234 is of bamboo fiber.

Figure 21:
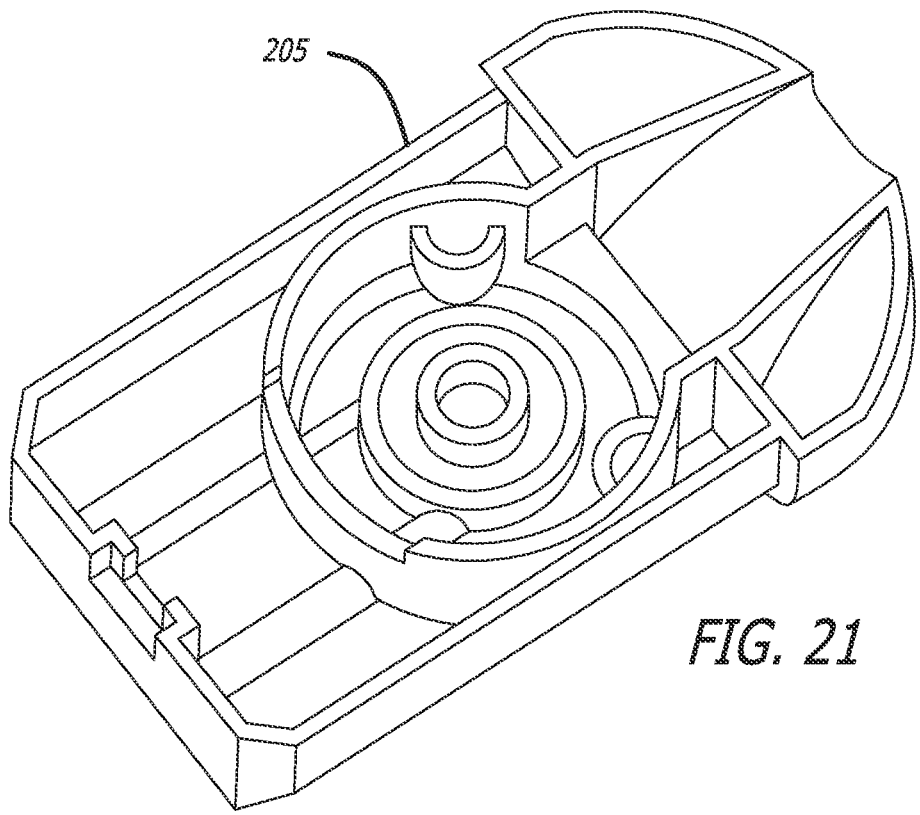
FIG. 21 is a diagrammatic perspective view of a part of a housing of this disclosure.
Figure 22:
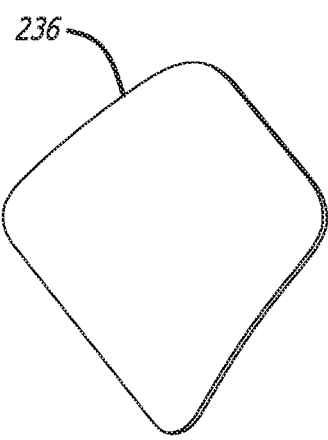
FIG. 22 is a diagrammatic perspective view of an absorbent element of this disclosure.
Figure 23:
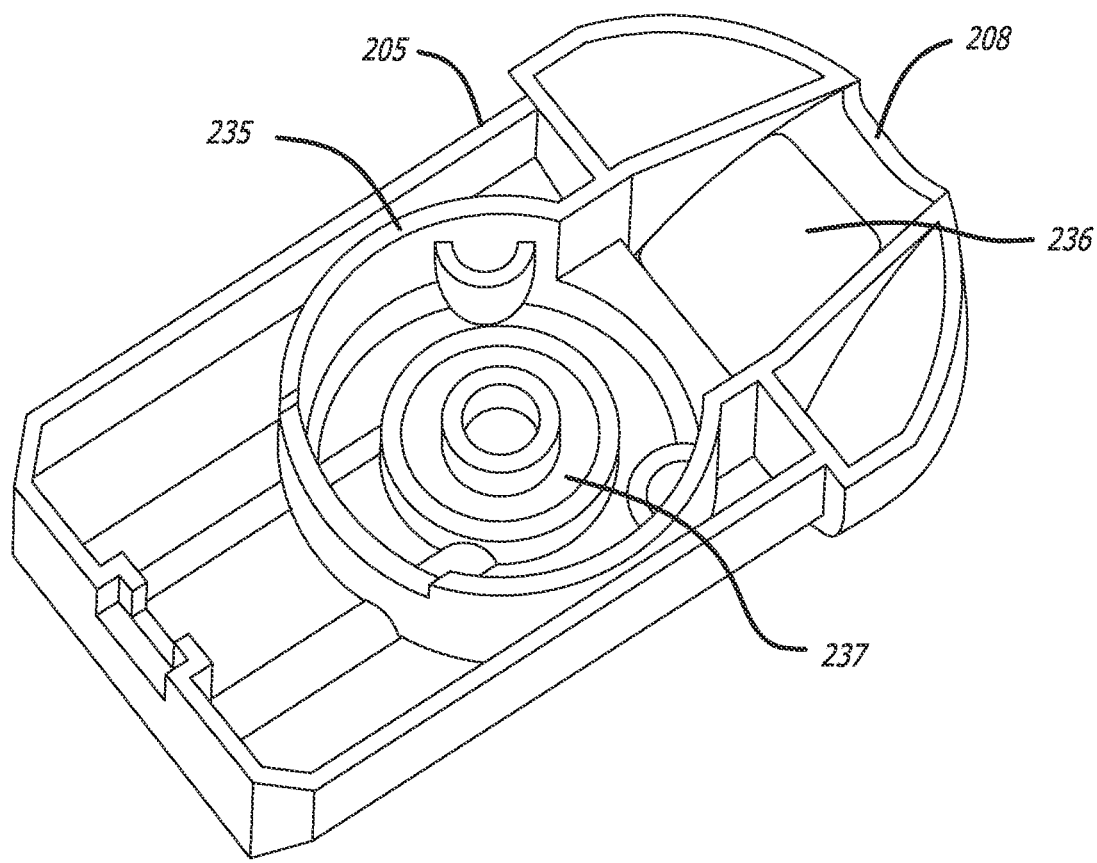
FIG. 23 is a diagrammatic perspective view of a part of a housing of this disclosure.

Referring now to FIGS. 21 to 23, the first portion 205 of the mist generator housing 204 is of a similar shape to the second portion 206 and comprises a further generally circular wall portion 235 which forms a further portion of the wall of the sonication chamber 219 and retains the transducer holder 210.

In this arrangement, a further absorbent element 236 is provided adjacent the mist outlet port 208 to absorb liquid at the mist outlet port 208.

Figure 24:
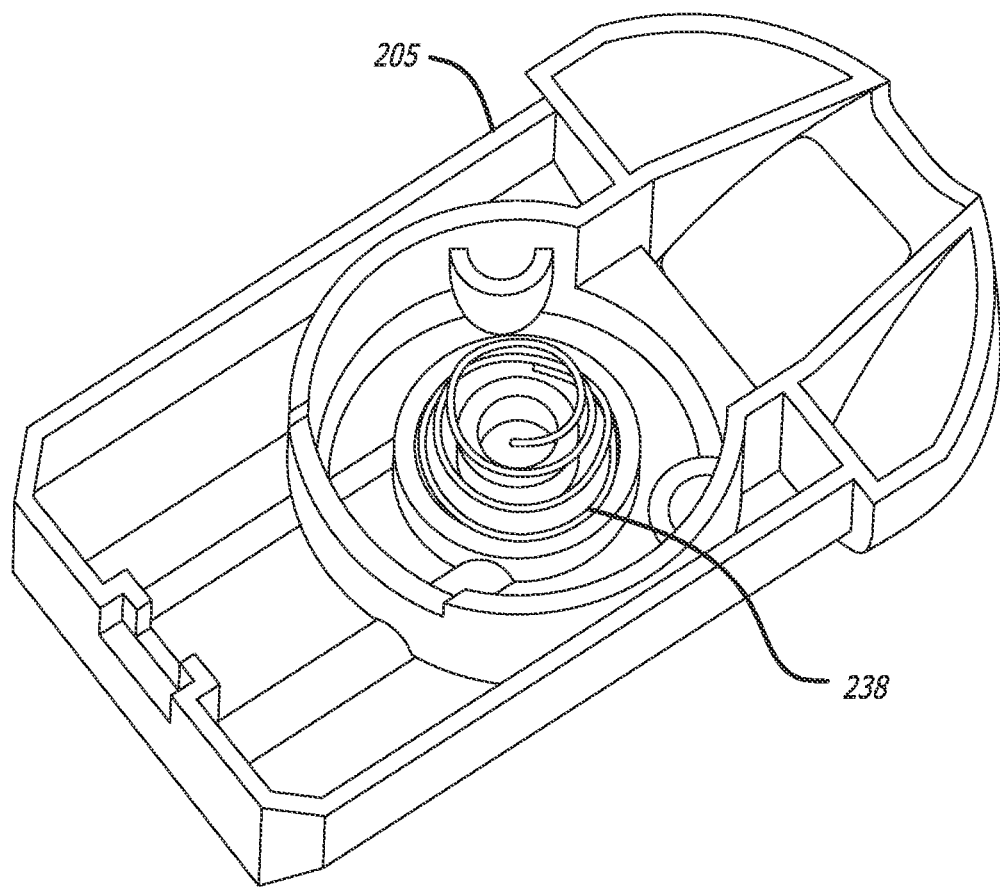
FIG. 24 is a diagrammatic perspective view of a part of a housing of this disclosure.

In this arrangement, the first portion 205 of the mist generator housing 204 comprises a spring support arrangement 237 which supports the lower end of a retainer spring 238, as shown in FIG. 24.

An upper end of the retainer spring 238 contacts the second portion 224 of the capillary element 222 such that the retainer spring 238 provides a biasing force which biases the capillary element 222 against the atomization surface of the ultrasonic transducer 215.

Figure 25:
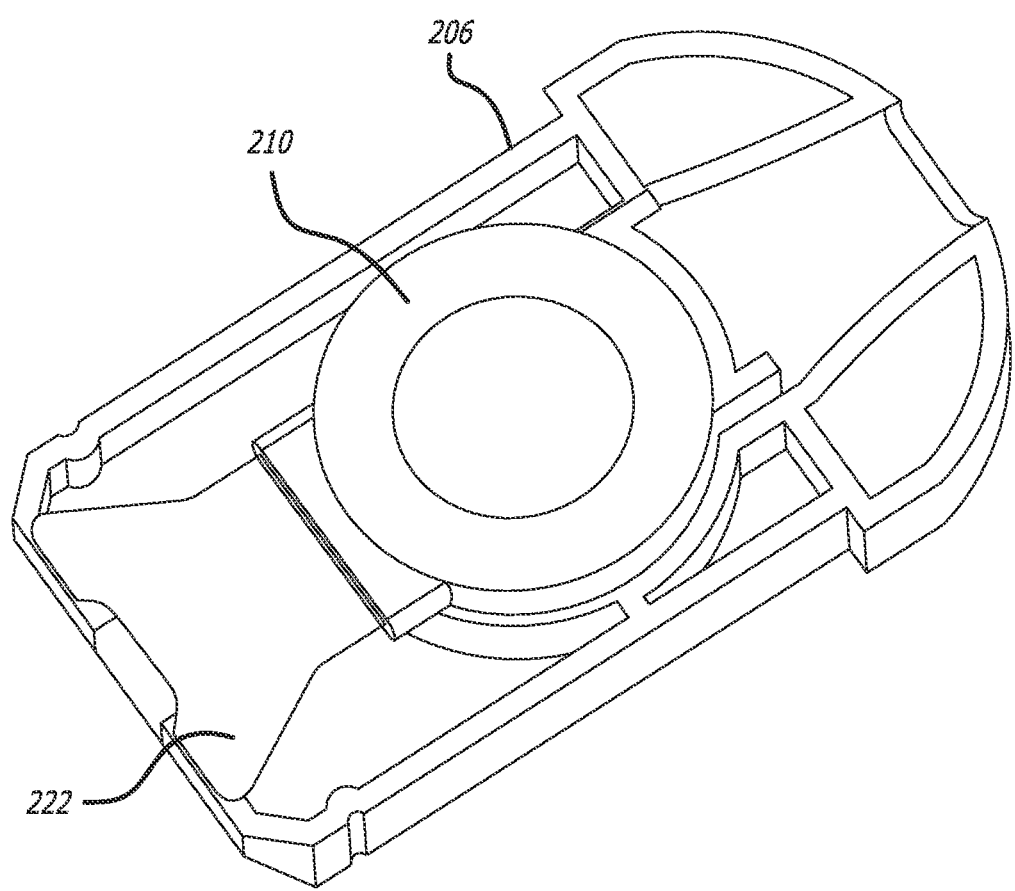
FIG. 25 is a diagrammatic perspective view of a part of a housing of this disclosure.
Figure 26:
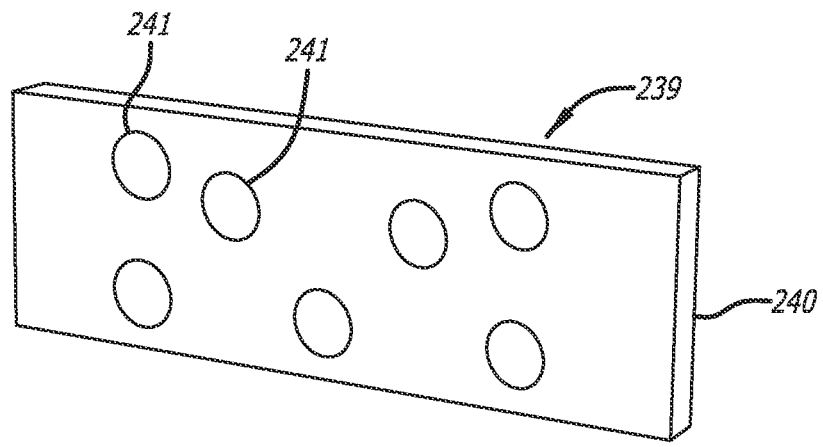
FIG. 26 is a diagrammatic perspective view of a circuit board of this disclosure.
Figure 27:
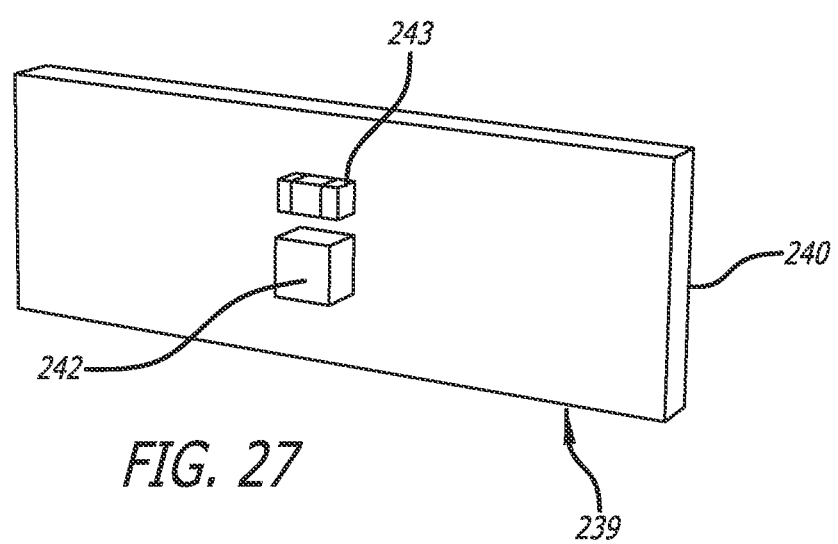
FIG. 27 is a diagrammatic perspective view of a circuit board of this disclosure.
Figure 28:
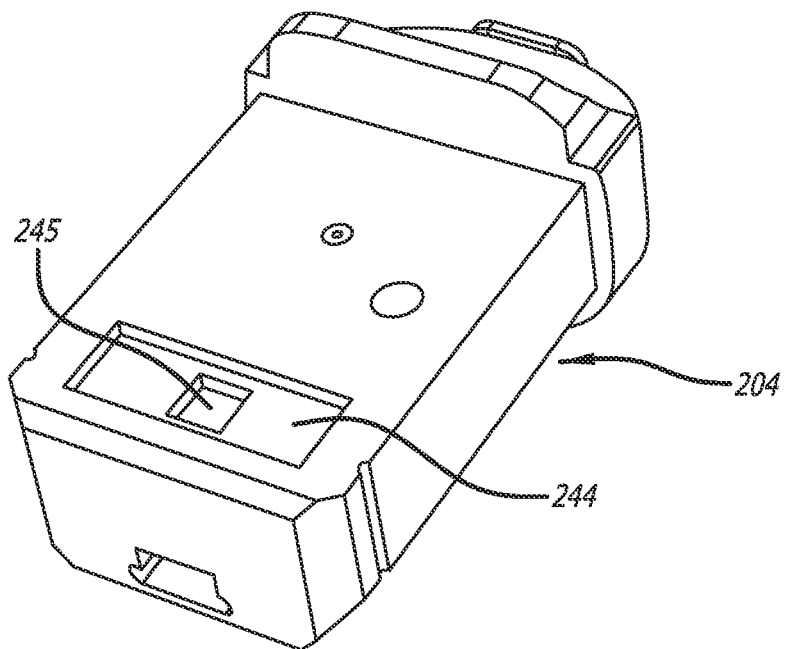
FIG. 28 is a diagrammatic exploded perspective view of a mist generator device of this disclosure.
Figure 29:
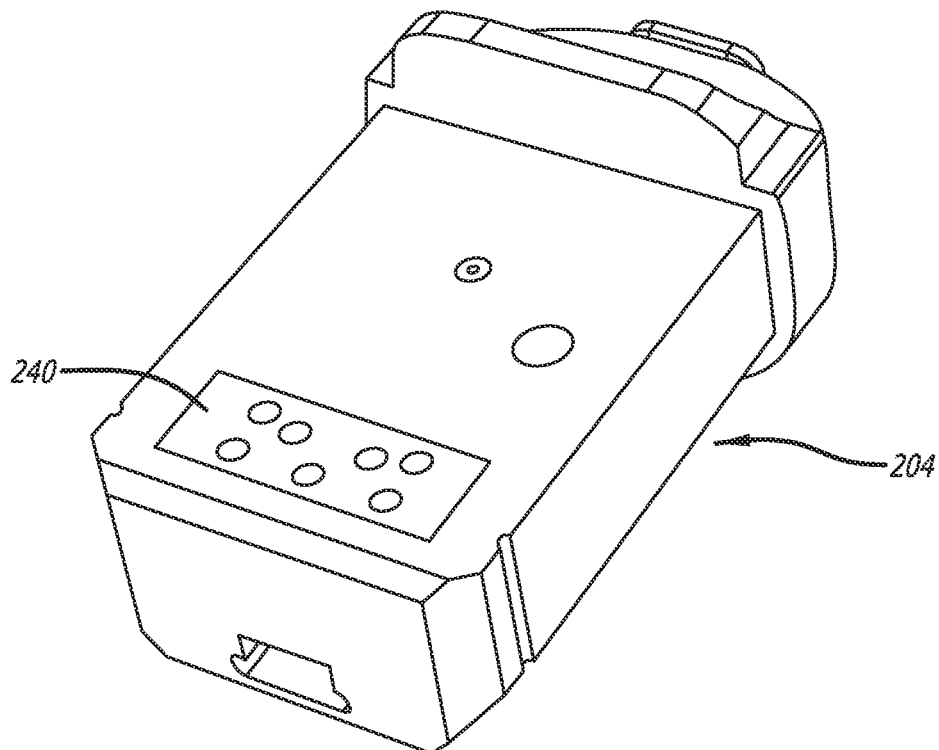
FIG. 29 is a diagrammatic exploded perspective view of a mist generator device of this disclosure.

Referring to FIG. 25, the transducer holder 210 is shown in position and being retained by the second portion 206 of the mist generator housing 204, prior to the two portions 205, 206 of the mist generator housing 204 being attached to one another.

Referring to FIGS. 26 to 29, in this arrangement, the mist generator device 201 comprises an identification arrangement 239. The identification arrangement 239 comprises a printed circuit board 240 having electrical contacts 241 provided on one side and an integrated circuit 242 and another optional component 243 provided on the other side.

The integrated circuit 242 has a memory which stores a unique identifier for the mist generator device 201. The electrical contacts 241 provide an electronic interface for communication with the integrated circuit 242.

The printed circuit board 240 is, in this arrangement, mounted within a recess 244 on one side of the mist generator housing 204. The integrated circuit 242 and optional other electronic components 243 sit within a further recess 245 so that the printed circuit board 240 is generally flush with the side of the mist generator housing 204.

In this arrangement, the integrated circuit 242 is a one-time-programmable (OTP) device which provides an anti-counterfeiting feature that allows only genuine mist generator devices from the manufacturer to be used with the device. This anti-counterfeiting feature is implemented in the mist generator device 201 as a specific custom integrated circuit (IC) that is bonded (with the printed circuit board 240) to the mist generator device 201. The OTP as IC contains a truly unique information that allows a complete traceability of the mist generator device 201 (and its content) over its lifetime as well as a precise monitoring of the consumption by the user. The OTP IC allows the mist generator device 201 to function to generate mist only when authorized.

The OTP, as a feature, dictates the authorized status of a specific mist generator device 201. Indeed, in order to prevent emissions of carbonyls and keep the aerosol at safe standards, experiments have shown that the mist generator device 201 is considered empty of liquid in the liquid chamber 218 after approximately 1,000 seconds of aerosolization. In that way a mist generator device 201 that is not genuine or empty will not be able to be activated after this predetermined duration of use.

The OTP, as a feature, may be part of a complete chain with the conjunction of the digital sale point, the mobile companion application and the mist generator device 201. Only a genuine mist generator device 201 manufactured by a trusted party and sold on the digital sale point can be used in the hookah device 202. The OTP IC is read by the hookah device 202 which recognizes the mist generator device 201.

In some arrangements, the OTP IC is disposable in the same way as the mist generator device 201. Whenever the mist generator device 201 is considered empty, it will not be activated if inserted into a hookah device 202. Similarly, a counterfeit mist generator device 201 would not be functional in the hookah device 202.

Figure 30:
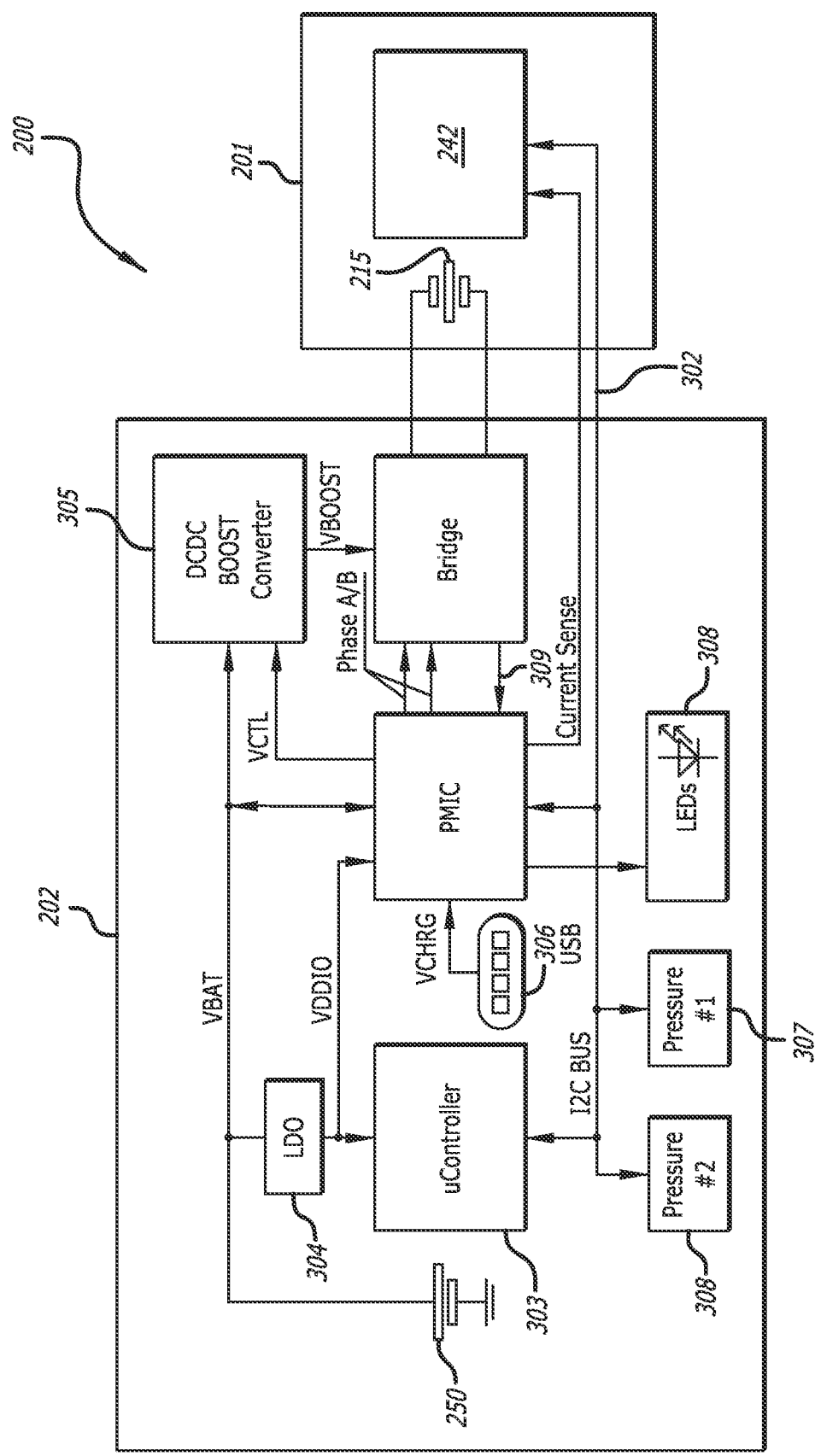
FIG. 30 is a schematic diagram of an integrated circuit arrangement of this disclosure.

Referring now to FIG. 30 of the accompanying drawings, the hookah device 202 comprises a plurality of ultrasonic transducer driver microchips, each of which is referred to herein as a power management integrated circuit or PMIC 300. Each PMIC 300 is a microchip for driving a respective ultrasonic transducer 215 in one of the mist generator devices 201. In examples of this disclosure, the number of PMICs in the hookah device 202 corresponds to the number of mist generator devices 201 that are for use with the hookah device 202. In the example described below, there are four mist generator devices 201 and the hookah device 202 comprises four corresponding PMICs 300, In other examples, the hookah device 202 comprises two to eight PMICs 300 which are configured to drive two to eight mist generator devices 201 that are coupled to the hookah device 202.

In this disclosure, the terms chip, microchip and integrated circuit are interchangeable. The microchip or integrated circuit is a single unit which comprises a plurality of interconnected embedded components and subsystems. The microchip is, for example, at least partly of a semiconductor, such as silicon, and is fabricated using semiconductor manufacturing techniques.

The hookah device 202 also comprises a plurality of second microchips, each of which is referred to herein as a bridge integrated circuit or bridge IC 301. Each bridge IC 301 is electrically connected a respective one of the PMICs 300. Each bridge IC 301 is a microchip for driving a respective ultrasonic transducer 215 in one of the mist generator devices 201. In examples of this disclosure, the number of bridge ICs 301 in the hookah device 202 corresponds to the number of mist generator devices 201 that are for use with the hookah device 202. Each bridge IC 301 is a single unit which comprises a plurality of interconnected embedded components and subsystems. In the example described below, there are four bridge ICs 301 and the hookah device 202 comprises four corresponding PMICs 300.

In this example, each PMIC 300 its respective connected bridge IC 301 are mounted to the same PCB of the hookah device 202. As described below, each bridge IC 301 is connected to its respective PMIC 300 via connections on a PCB and not via a communications bus (e.g. the I2C bus described below). In this example, the physical dimensions of the PMIC 300 are 1-3 mm wide and 1-3 mm long and the physical dimensions of the bridge IC 301 are 1-3 mm wide and 1-3 mm long.

Figure 43:
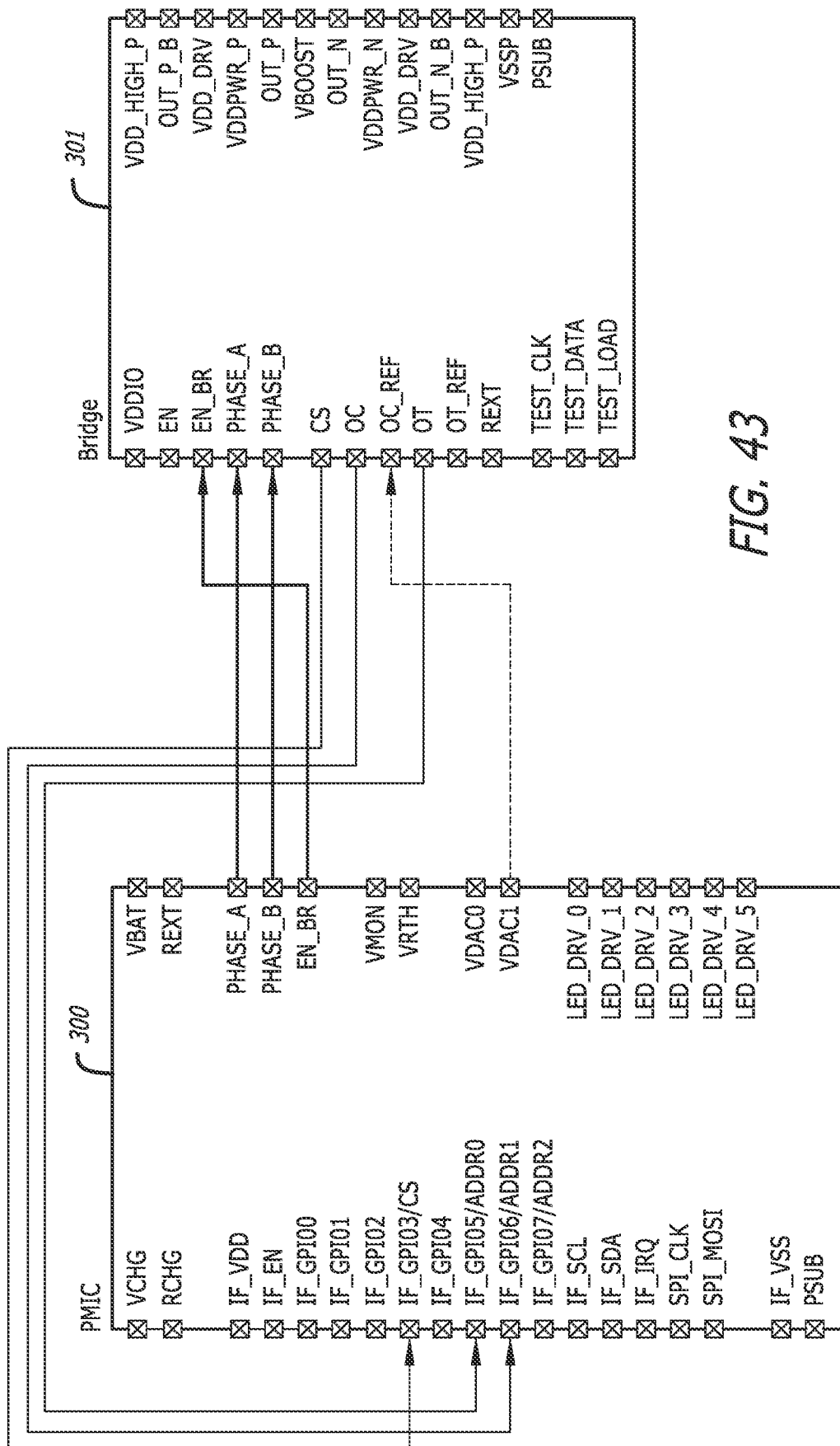
FIG. 43 is a schematic diagram showing connections between integrated circuits of this disclosure.

For simplicity, FIG. 43 shows only one PMIC 300 and one bridge IC 301 and the following description refers to only one PMIC 300 and one bridge IC 301. However, it is to be appreciated that the hookah device 202 incorporates a plurality of PMICs 300 and a plurality of respective bridge ICs 301 which are connected in the same configuration as shown in FIG. 43. As described below, each PMIC 300 is connected to a communications (I2C) bus 302 so that each PMIC 300 can be controlled independently by signals from a microcontroller 303 which are sent via the communications bus 302, As described above, the mist generator device 201 comprises a programmable or one time programmable integrated circuit or OTP IC 242. When the mist generator device 201 is coupled to the hookah device 202, the OTP IC is electrically connected to the PMIC 300 to receive power from the PMIC 300 such that the PMIC 300 can manage the voltage supplied to the OTP IC 242. The OTP IC 242 is also connected to a data bus or communications bus 302 in the hookah device 202. In this example, the communications bus 302 is an I2C bus but in other examples the communications bus 302 is another type of data bus.

The ultrasonic transducer 215 in the mist generator device 201 is electrically connected to the bridge IC 301 so that the ultrasonic transducer 215 may be driven by an AC drive signal generated by the bridge IC 301 when the hookah device 202 is in use.

The hookah device 202 comprises a processor in the form of the microcontroller 303 which is electrically coupled for communication with the communication bus 302. In this example, the microcontroller 303 is a Bluetooth™ low energy (BLE) microcontroller. The microcontroller 303 receives power from a low dropout regulator (LDO) 304 which is driven by a battery or, in this example, from an external power supply. The LDO 304 provides a stable regulated voltage to the microcontroller 303 to enable the microcontroller 303 to operate consistently even when there is a variation in the voltage of the battery or other power supply.

The hookah device 202 comprises a voltage regulator in the form of a DC-DC boost converter 305 which is powered by the battery or an external power supply. Only one DC-DC boost converter 305 is shown in FIG. 43 but in some examples the hookah device 202 comprises a plurality of DC-DC boost converters 305 which each supply power to a respective one of the plurality of bridge ICs 301. In other examples, the hookah device 305 comprises only one DC-DC boost converter 305 which is configured to supply power to each of the plurality of bridge ICs 301.

The boost converter 305 increases the voltage of the battery or power supply to a programmable voltage VBOOST. The programmable voltage VBOOST is set by the boost converter 305 in response to a voltage control signal VCTL from the PMIC 300. As will be described in more detail below, the boost converter 305 outputs the voltage VBOOST to the bridge IC 301. In other examples, the voltage regulator is a buck converter or another type of voltage regulator which outputs a selectable voltage.

The voltage control signal VCTL is generated by a digital to analogue converter (DAC) which, in this example, is implemented within the PMIC 300. The DAC is not visible in FIG. 30 since the DAC is integrated within the PMIC 300. The DAC and the technical benefits of integrating the DAC within the PMIC 300 are described in detail below, In this example, the PMIC 300 is connected to a power source connector 306 so that the PMIC 300 can receive a charging voltage VCHRG when the power source connector 306 is coupled to a USB charger. In other examples, the PMIC 300 is connected to a different power socket which enables the hookah device 202 to be connected to and be powered by an external power source.

The hookah device 202 comprises a first pressure sensor 307 which, in this example, is a static pressure sensor. The hookah device 202 also comprises a second pressure sensor 308 which, in this example, is a dynamic pressure sensor. However, in other examples, the hookah device 202 comprises only one of the two pressure sensors 307, 308. The pressure sensors 307, 308 sense a change in air pressure to sense when a user is drawing on the hookah and drawing air through the mist generator device 201.

In this example, the hookah device 202 comprises a plurality of LEDs 308 which are controlled by the PMIC 300. In other examples, one or more of the LEDs 308 are omitted.

The microcontroller 303 functions as a master device on the communications bus 302, with the PMIC 300 being a first slave device, the OTP IC 242 being a second slave device, the second pressure sensor 308 being a third slave device and the first pressure sensor 307 being the a fourth slave device. Each additional PMIC 300 of the plurality of PMICs 300 is another slave device on the communications bus 302. The communication bus 302 enables the microcontroller 303 to control the following functions within the hookah device 202:

1. All functions of each PMIC 300 are highly configurable by the microcontroller 303.
2. The current flowing through the ultrasonic transducer 215 is sensed by a high bandwidth sense and rectifier circuit at a high common mode voltage (high side of the bridge). The sensed current is converted into a voltage proportional to the rms current and provided as a buffered voltage at a current sense output pin 309 of the bridge IC 301. This voltage is fed to and sampled in the PMIC 300 and made available as a digital representation via I2C requests. Sensing the current flowing through the ultrasonic transducer 215 forms part of the resonant frequency tracking functionality. As described herein, the ability of the device to enable this functionality within the bridge IC 301 provides significant technical benefits.
3. The DAC (not shown in FIG. 30) integrated within the PMIC 300 enables the DC-DC boost converter voltage VBOOST to be programmed to be between 10V and 20V.
4. The microcontroller 303 enables the charger subsystem of the device 202 to manage the charging of a battery, which may be is a single cell battery.
5. A Light Emitting Diode (LED) driver module (not shown) is powered by the PMIC 300 to drive and dim digitally the LEDs 308 either in linear mode or in gamma corrected mode.
6. The microcontroller 303 is able to read Pressure #1 and Pressure #2 sensor values from the pressure sensors 307, 308.

Figure 31:
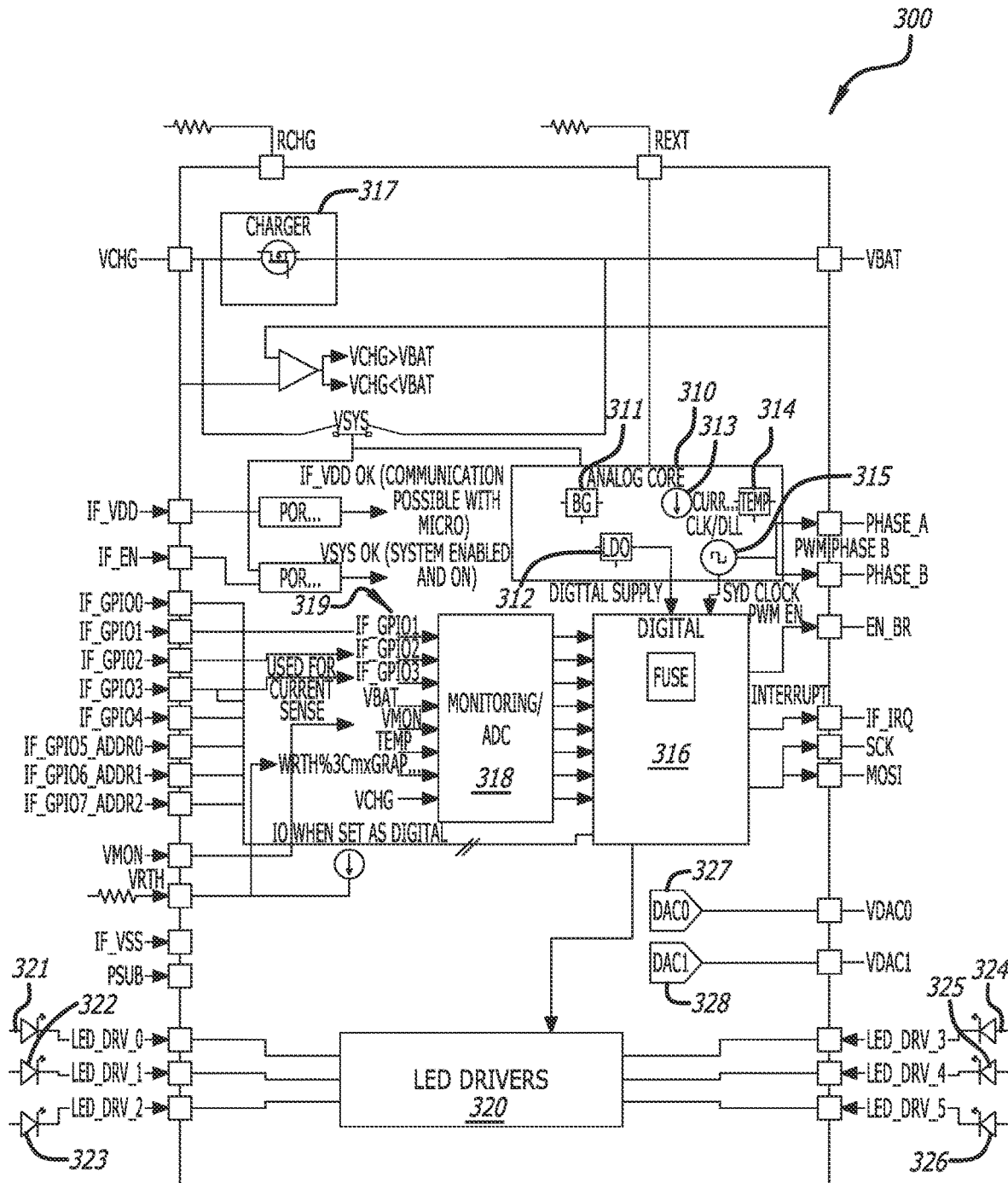
FIG. 31 is a schematic diagram of an integrated circuit of this disclosure.

Referring now to FIG. 31 of the accompanying drawings, each PMIC 300 is, in this example, a self-contained chip or integrated circuit which comprises integrated subsystems and a plurality of pins which provide electrical inputs and outputs to the PMIC 300. The references to an integrated circuit or chip in this disclosure are interchangeable and either term encompasses a semiconductor device which may, for instance, be of silicon.

The PMIC 300 comprises an analogue core 310 which comprises analogue components including a reference block (BG) 311, a LDO 312, a current sensor 313, a temperature sensor 314 and an oscillator 315.

As described in more detail below, the oscillator 315 is coupled to a delay locked loop (DLL) which outputs pulse width modulation (PWM) phases A and B. The oscillator 315 and the DLL generate a two phase centre aligned PWM output which drives an H bridge in the bridge IC 301.

The DLL comprises a plurality of delay lines connected end to end, wherein the total delay of the delay lines is equal to the period of the main clock signal clk_m. In this example, the DLL is implemented in a digital processor subsystem, referred to herein as a digital core 316, of the PMIC 300 which receives a clock signal from the oscillator 315 and a regulated power supply voltage from the LDO 312. The DLL is implemented in a large number (e.g. in the order of millions) of delay gates which are connected end to end in the digital core 316.

The implementation of the oscillator 315 and the DLL in the same integrated circuit of the PMIC 300 in order to generate a two phase centre aligned PWM signal is unique since at present no signal generator component in the integrated circuit market comprises this implementation.

As described herein, PWM is part of the functionality which enables the hookah device 202 to track the resonant frequency of the ultrasonic transducer 215 accurately in order to maintain an efficient transfer from electrical energy to kinetic energy in order to optimise the generation of mist.

In this example, the PMIC 300 comprises a charger circuit 317 which controls the charging of a battery, for instance by power from a USB power source.

The PMIC 300 comprises an integrated power switch VSYS which configures the PMIC 300 to power the analogue core 310 by power from a battery or by power from an external power source.

The PMIC 300 comprises an embedded analogue to digital converter (ADC) subsystem 318. The implementation of the ADC 318 together with the oscillator 315 in the same integrated circuit is, in itself, unique since there is no other integrated circuit in the integrated circuit market which comprises an oscillator and an ADC implemented as sub-blocks within the integrated circuit. In a conventional device, an ADC is typically provided as a separate discrete component from an oscillator with the separate ADC and oscillator being mounted to the same PCB. The problem with this conventional arrangement is that the two separate components of the ADC and the oscillator take up space unnecessarily on the PCB. A further problem is that the conventional ADC and oscillator are usually connected to one another by a serial data communication bus, such as an I2C bus, which has a limited communication speed of up to only 400 kHz. In contrast to conventional devices, the PMIC 300 comprises the ADC 318 and the oscillator 315 integrated within the same integrated circuit which eliminates any lag in communication between the ADC 318 and the oscillator 315, meaning that the ADC 318 and the oscillator 315 can communicate with one another at high speed, such as at the speed of the oscillator 315 (e.g. 3 MHz to 5 MHz).

In the PMIC 300 of this example, the oscillator 315 is running at 5 MHz and generates a clock signal SYS CLOCK at 5 MHz. However, in other examples, the oscillator 315 generates a clock signal at a much higher frequency of up to 105 MHz. The integrated circuits described herein are all configured to operate at the high frequency of the oscillator 315.

The ADC 318 comprises a plurality of feedback input terminals or analogue inputs 319 which comprise a plurality of GPIO inputs (IF_GPIO1-3). At least one of the feedback input terminals or the analogue inputs 319 receives a feedback signal from an H-bridge circuit in the bridge IC 301, the feedback signal being indicative of a parameter of the operation of the H-bridge circuit or an AC drive signal when the H-bridge circuit is driving a resonant circuit, such as the ultrasonic transducer 215, with the AC drive signal. As described below, the GPIO inputs are used to receive a current sense signal from the bridge IC 301 which is indicative of the route mean square (rms) current reported by the bridge IC 301. In this example, one of the GPIO inputs is a feedback input terminal which receives a feedback signal from the H-bridge in the bridge IC 301.

The ADC subsystem 318 samples analogue signals received at the plurality of ADC input terminals 319 at a sampling frequency which is proportional to the frequency of the main clock signal. The ADC subsystem 318 then generates ADC digital signals using the sampled analogue signals.

In this example, the ADC 318 which is incorporated in the PMIC 300 samples not only the RMS current flowing through the H-bridge 334 and the ultrasonic transducer 215 but also voltages available in the system (e.g. VBAT, VCHRG, VBOOST), the temperature of the PMIC 300, the temperature of a battery and the GPIO inputs (IF_GPIO1-3) which allow for future extensions.

The digital core 316 receives the ADC generated digital signals from the ADC subsystem and processes the ADC digital signals to generate the driver control signal. The digital core 316 communicates the driver control signal to the PWM signal generator subsystem (DLL 332) to control the PWM signal generator subsystem.

Rectification circuits existing in the market today have a very limited bandwidth (typically less than 1 MHz). Since the oscillator 315 of the PMIC 300 is running at up to 5 MHz or even up to 105 Mhz, a high bandwidth rectifier circuit is implemented in the PMIC 300. As will be described below, sensing the RMS current within an H bridge of the bridge IC 301 forms part of a feedback loop which enables the hookah device 202 to drive the ultrasonic transducer 215 with high precision. The feedback loop is a game changer in the industry of driving ultrasound transducers since it accommodates for any process variation in the piezo electric transducer production (variations of resonance frequencies) and it compensates for temperature effects of the resonance frequency. This is achieved, in part, by the inventive realisation of integrating the ADC 318, the oscillator 315 and the DLL within the same integrated circuit of the PMIC 300. The integration enables these sub-systems to communicate with one another at high speed (e.g. at the clock frequency of 5 MHz or up to 105 MHz). Reducing the lag between these subsystems is a game changer in the ultrasonics industry, particularly in the field of mist generator devices, The ADC 318 comprises a battery voltage monitoring input/BAT and a charger input voltage monitoring input VCHG as well as voltage monitoring inputs VMON and VRTH as well as a temperature monitoring input TEMP.

The temperature monitoring input TEMP receives a temperature signal from the temperature sensor 314 which is embedded within the PMIC 300. This enables the PMIC 300 to sense the actual temperature within the PMIC 300 accurately so that the PMIC 300 can detect any malfunction within the PMIC 300 as well as malfunction to other components on the printed circuit board which affect the temperature of the PMIC 300. The PMIC 300 can then control the bridge IC 301 to prevent excitation of the ultrasonic transducer 215 if there is a malfunction in order to maintain the safety of the mist inhaler device 200 and hence the safety of the hookah device 202.

The additional temperature sensor input VRTH receives a temperature sensing signal from an external temperature sensor within the hookah device 202 which monitors the temperature of within the hookah device 202. The PMIC 300 can thus react to shut down the hookah device 202 in order to reduce the risk of damage being caused by an excessively high operating temperature.

The PMIC 300 comprises an LED driver 320 which, in this example, receives a digital drive signal from the digital core 316 and provides LED drive output signals to six LEDs 321-326 which are configured to be coupled to output pins of the PMIC 300. The LED driver 320 can thus drive and dim the LEDs 321-326 in up to six independent channels.

The PMIC 300 comprises a first digital to analogue converter (DAC) 327 which converts digital signals within the PMIC 300 into an analogue voltage control signal which is output from the PMIC 300 via an output pin VDAC0. The first DAC 327 converts a digital control signal generated by the digital core 316 into an analogue voltage control signal which is output via the output pin VDAC0 to control a voltage regulator circuit, such as the boost converter 305. The voltage control signal thus controls the voltage regulator circuit to generate a predetermined voltage for modulation by the H-bridge circuit to drive the ultrasonic transducer 215 in response to feedback signals which are indicative of the operation of the ultrasonic transducer 215.

In this example, the PMIC 300 comprises a second DAC 328 which converts digital signals within the PMIC 300 into an analogue signal which is output from the PMIC 300 via a second analogue output pin VDAC1.

Embedding the DACs 327, 328 within the same microchip as the other subsystems of the PMIC 300 allows the DACs 327, 328 to communicate with the digital core 316 and other components within the PMIC 300 at high speed with no or minimal communication lag. The DACs 327, 328 provide analogue outputs which control external feedback loops. For instance, the first DAC 327 provides the control signal VCTL to the boost converter 305 to control the operation of the boost converter 305. In other examples, the DACs 327, 328 are configured to provide a drive signal to a DC-DC buck converter instead of or in addition to the boost converter 305. Integrating the two independent DAC channels in the PMIC 300 enables the PMIC 300 to manipulate the feedback loop of any regulator used in the hookah device 202 and allows the hookah device 202 to regulate the sonication power of the ultrasonic transducer 215 or to set analogue thresholds for absolute maximum current and temperature settings of the ultrasonic transducer 215.

The PMIC 300 comprises a serial communication interface which, in this example, is an I2C interface which incorporates external I2C address set through pins.

The PMIC 300 also comprises various functional blocks which include a digital machine (FSM) to implement the functionality of the microchip. These blocks will be described in more detail below.

Figure 32:
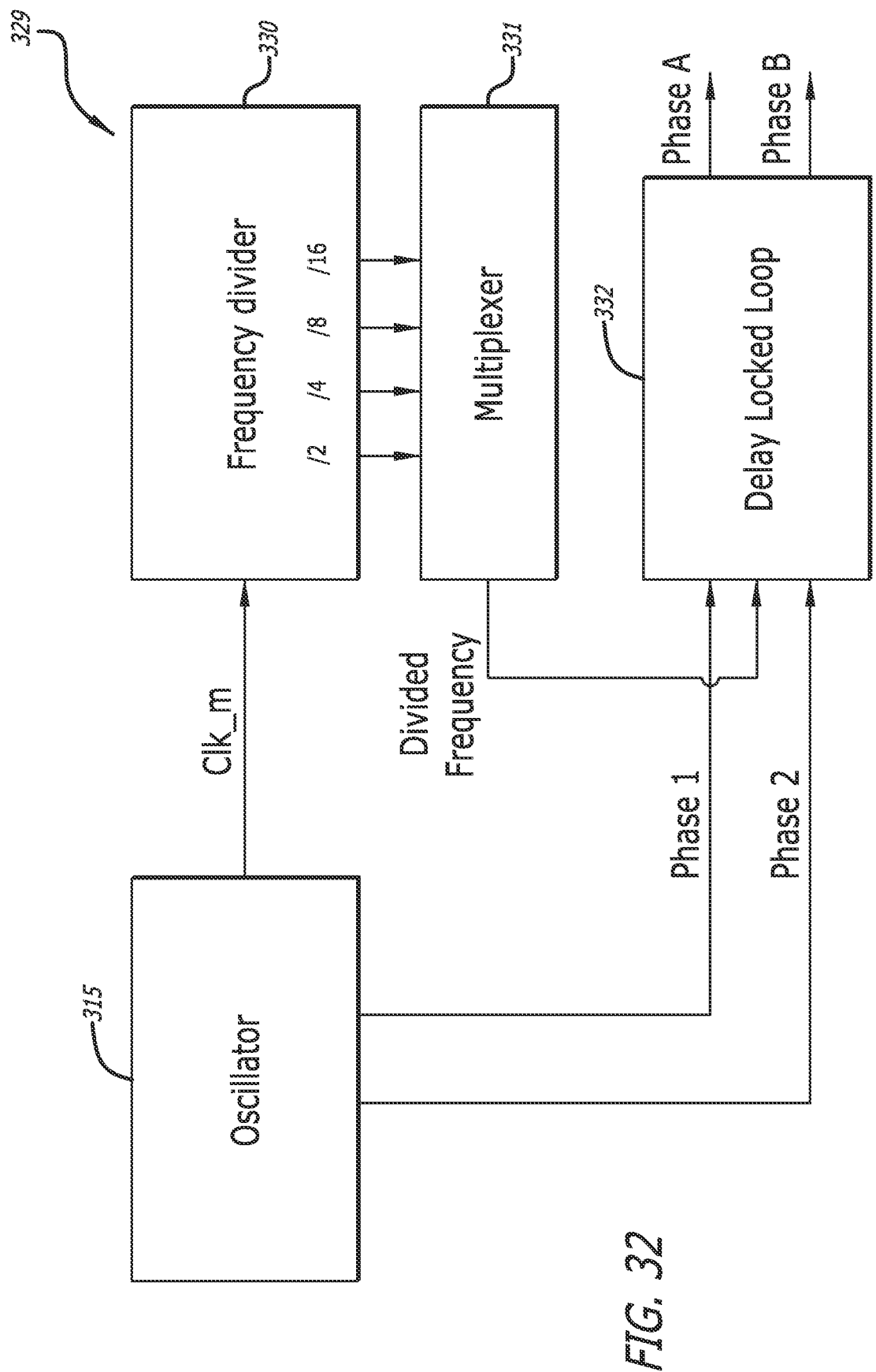
FIG. 32 is a schematic diagram of a pulse width modulation generator of this disclosure.

Referring now to FIG. 32 of the accompanying drawings, a pulse width modulation (PWM) signal generator subsystem 329 is embedded within the PMIC 300. The PWM generator system 329 comprises the oscillator 315, and frequency divider 330, a multiplexer 331 and a delay locked loop (DLL) 332. As will be described below, the PWM generator system 329 is a two phase centre aligned PWM generator.

The frequency divider 330, the multiplexer 331 and the DLL 332 are implemented in digital logic components (e.g. transistors, logic gates, etc.) within the digital core 316.

In examples of this disclosure, the frequency range which is covered by the oscillator 315 and respectively by the PWM generator system 329 is 50 kHz to 5 MHz or up to 105 MHz. The frequency accuracy of the PWM generator system 329 is ±1% and the spread over temperature is ±1%. In the IC market today, no IC has an embedded oscillator and two phase centre aligned PWM generator that can provide a frequency range of 50 kHz to 5 MHz or up to 105 MHz.

The oscillator 315 generates a main clock signal (clk_m) with a frequency of 50 kHz to 5 MHz or up to 105 MHz. The main clock clk_m is input to the frequency divider 330 which divides the frequency of the main clock clkm by one or more predetermined divisor amounts. In this example, the frequency divider 330 divides the frequency of the main clock clk_m by 2, 4, 8 and 16 and provides the divided frequency docks as outputs to the multiplexer 331. The multiplexer 331 multiplexes the divided frequency docks and provides a divided frequency output to the DLL 332. This signal which is passed to the DLL 332 is a frequency reference signal which controls the DLL 332 to output signals at a desired frequency. In other examples, the frequency divider 330 and the multiplexer 331 are omitted.

Figure 33:
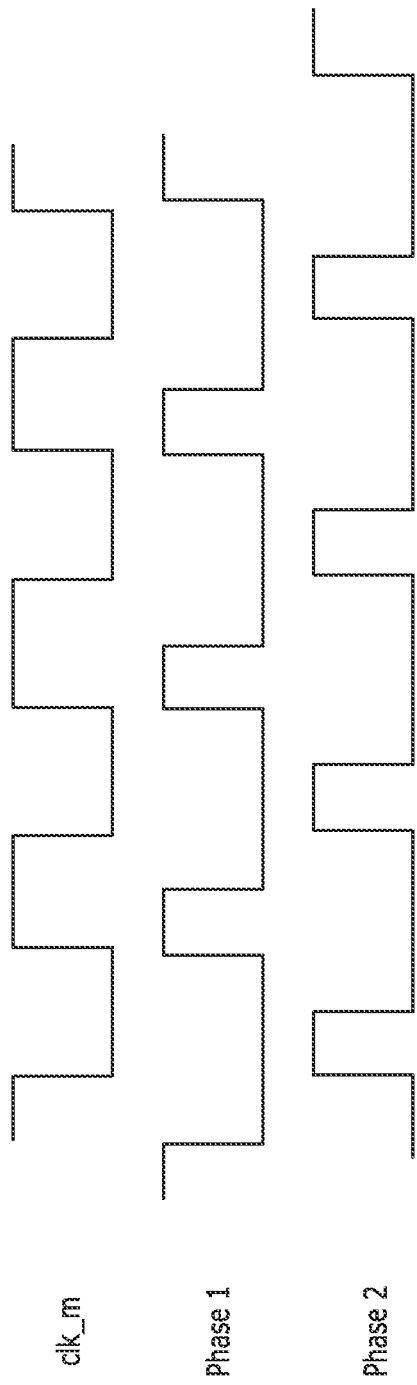
FIG. 33 is timing diagram of an example of this disclosure.

The oscillator 315 also generates two phases; a first phase dock signal Phase 1 and a second phase dock signal Phase 2. The phases of the first phase dock signal and the second phase dock signal are centre aligned. As illustrated in FIG. 33:

The first phase dock signal Phase 1 is high for a variable time of clk_m's positive half-period and low during clk_m's negative half-period.

The second phase dock signal Phase 2 is high for a variable time of clk_m's negative half-period and low during clk_m's positive half-period.

Phase 1 and Phase 2 are then sent to the DLL 332 which generates a double frequency dock signal using the first phase dock signal Phase 1 and the second phase dock signal Phase 2. The double frequency dock signal is double the frequency of the main dock signal clk_m. In this example, an "OR" gate within the DLL 332 generates the double frequency dock signal using the first phase dock signal Phase 1 and the second phase dock signal Phase 2. This double frequency dock or the divided frequency coming from the frequency divider 330 is selected based on a target frequency selected and then used as reference for the DLL 332.

Within the DLL 332, a signal referred to hereafter as "dock" represents the main dock clk_m multiplied by 2, while a signal referred to hereafter as "dock del" is a replica of dock delayed by one period of the frequency. Clock and clock del are passed through a phase frequency detector. A node Vc is then charged or discharged by a charge-pump based on the phase error polarity. A control voltage is fed directly to control the delay of every single delay unit within the DLL 332 until the total delay of the DLL 332 is exactly one period.

The DLL 332 controls the rising edge of the first phase dock signal Phase 1 and the second phase dock signal Phase 2 to be synchronous with the rising edge of the double frequency dock signal. The DLL 332 adjusts the frequency and the duty cycle of the first phase dock signal Phase 1 and the second phase dock signal Phase 2 in response to a respective frequency reference signal and a duty cycle control signal to produce a first phase output signal Phase A and a second phase output signal Phase B to drive an H-bridge or an inverter to generate an AC drive signal to drive an ultrasonic transducer.

The PMIC 300 comprises a first phase output signal terminal PHASE_A which outputs the first phase output signal Phase A to an H-bridge circuit and a second phase output signal terminal PHASE_B which outputs the second phase output signal Phase B to an H-bridge circuit.

In this example, the DLL 332 adjusts the duty cycle of the first phase clock signal Phase 1 and the second phase clock signal Phase 2 in response to the duty cycle control signal by varying the delay of each delay line in the DLL 332 response to the duty cycle control signal.

Figure 34:
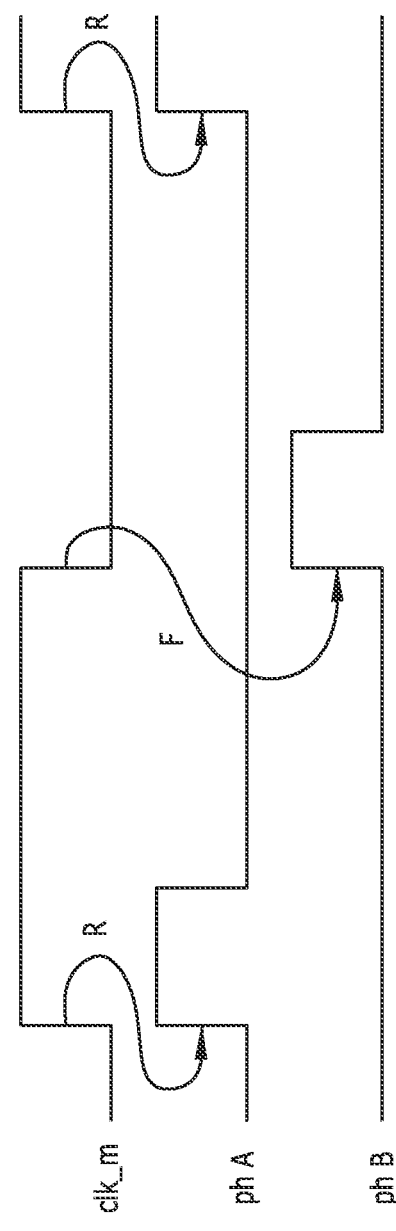
FIG. 34 is timing diagram of an example of this disclosure.

The clock is used at double of its frequency because guarantees better accuracy. As shown in FIG. 34, for the purpose of explanation if the frequency of the main clock clk_m is used (which it is not in examples of this disclosure), Phase A is synchronous with clock's rising edge R, while Phase B is synchronous with clock's falling edge F. The delay line of the DLL 332 controls the rising edge R and so, for the falling edge F, the PWM generator system 329 would need to rely on a perfect matching of the delay units of the DLL 332 which can be imperfect. However, to remove this error, the PWM generator system 329 uses the double frequency clock so that both Phase A and Phase B are synchronous with the rising edge R of the double frequency clock.

To perform a duty-cycle from 20% to 50% with a 2% step size, the delay line of the DLL 332 comprises 25 delay units, with the output of each respective delay unit representing a Phase nth. Eventually the phase of the output of the final delay unit will correspond to the input clock. Considering that all delays will be almost the same, a particular duty cycle is obtained with the output of the specific delay unit with simple logic in the digital core 316.

It is important to take care of the DLL 332 startup as the DLL 332 might not be able to lock a period of delay but two or more periods, taking the DLL 332 to a non-convergence zone. To avoid this issue, a start-up circuit is implemented in the PWM generator system 329 which allows the DLL 332 to start from a known and deterministic condition. The start-up circuit furthermore allows the DLL 332 to start with the minimum delay.

In examples of this disclosure, the frequency range covered by the PWM generator system 329 is extended and so the delay units in the DLL 332 can provide delays of 4 ns (for an oscillator frequency of 5 MHz) to 400 ns (for an oscillator frequency of 50 kHz). In order to accommodate for these differing delays, capacitors Cb are included in the PWM generator system 329, with the capacitor value being selected to provide the required delay.

The Phase A and Phase B are output from the DLL 332 and passed through a digital 10 to the bridge IC 301 so that the Phase A and Phase B can be used to control the operation of the bridge IC 301.

The battery charging functionality of some examples of the hookah device 202 will now be described in more detail. It is, however, to be appreciated that the battery charging functionality may be omitted in other examples in which the hookah device 202 is configure to be powered by an external power source instead of a battery.

In this example, the battery charging sub-system comprises the charger circuit 317 which is embedded in the PMIC 300 and controlled by a digital charge controller hosted in the PMIC 300. The charger circuit 317 is controlled by the microcontroller 303 via the communication bus 302. The battery charging sub-system is able to charge a single cell lithium polymer (LiPo) or lithium-ion (Li-ion) battery.

In this example, the battery charging sub-system is able to charge a battery or batteries with a charging current of up to 1 A from a 5V power supply (e.g. a USB power supply). One or more of the following parameters can be programmed through the communication bus 302 (I2C interface) to adapt the charge parameters for the battery:

Charge voltage can be set between 3.9V and 4.3V in 100mV steps.

The charge current can be set between 150 mA and 1000 mA in 50 mA steps.

The pre-charge current is ⅒ of the charge current.

Pre-charge and fast charge timeouts can be set between 5 and 85 min respectively 20 and 340 min.

Optionally an external negative temperature coefficient (NTC) thermistor can be used to monitor the battery temperature.

In some examples, the battery charging sub-system reports one or more of the following events by raising an interrupt to the host microcontroller 303:

Battery detected
Battery is being charged
Battery is fully charged
Battery is not present
Charge timeout reached
Charging supply is below the undervoltage limit The main advantage of having the charger circuit 317 embedded in the PMIC 300, is that it allows all the programming options and event indications listed to be implemented within the PMIC 300 which guarantees the safe operation of the battery charging sub-system. Furthermore, a significant manufacturing cost and PCB space saving can be accomplished compared with conventional mist inhaler devices which comprise discrete components of a charging system mounted separately on a PCB. The charger circuit 317 also allows for highly versatile setting of charge current and voltage, different fault timeouts and numerous event flags for detailed status analysis.

The analogue to digital converter (ADC) 318 will now be described in more detail. The inventors had to overcome significant technical challenges to integrate the ADC 318 within the PMIC 300 with the high speed oscillator 315, Moreover, integrating the ADC 318 within the PMIC 300 goes against the conventional approach in the art which relies on using one of the many discrete ADC devices that are available in the IC market.

In this example, the ADC 318 samples at least one parameter within the ultrasonic transducer driver chip (PMIC 300) at a sampling rate which is equal to the frequency of the main clock signal clk_m. In this example, the ADC 318 is a 10 bit analogue to digital converter which is able to unload digital sampling from the microprocessor 303 to save the resources of the microprocessor 303. Integrating the ADC 318 within the PMIC 300 also avoids the need to use an I2C bus that would otherwise slow down the sampling ability of the ADC (a conventional device relies on an I2C bus to communicate data between a dedicated discrete ADC and a microcontroller at a limited clock speed of typically up to 400 kHz), In examples of this disclosure, one or ore of the following parameters can be sampled sequentially by the ADC 318:

i. An rms current signal which is received at the ultrasonic transducer driver chip (PMIC 300) from an external inverter circuit which is driving an ultrasonic transducer. In this is example, this parameter is a root mean square (rms) current reported by the bridge IC 301. Sensing the rms current is important to implementing the feedback loop used for driving the ultrasound transducer 215. The ADC 318 is able to sense the rms current directly from the bridge IC 301 via a signal with minimal or no lag since the ADC 318 does not rely on this information being transmitted via an I2C bus. This provides a significant speed and accuracy benefit over conventional devices which are constrained by the comparatively low speeds of an I2C bus.

ii. The voltage of a battery connected to the PMIC 300.

iii. The voltage of a charger connected to the PMIC 300.

iv. A temperature signal, such as a temperature signal which is indicative of the PMIC 300 chip temperature. As described above, this temperature can be measured very accurately due to the temperature sensor 314 being embedded in the same IC as the oscillator 315. For example, if the PMIC 300 temperature goes up, the current, frequency and PWM are regulated by the PMIC 300 to control the transducer oscillation which in turn controls the temperature.

v. Two external pins.

vi. External NTC temperature sensor to monitor battery pack temperature.

In some examples, the ADC 318 samples one or more of the above-mentioned sources sequentially, for instance in a round robin scheme. The ADC 318 samples the sources at high speed, such as the speed of the oscillator 315 which may be up to 5 MHz or up to 105 MHz.

In some examples, the device 202 is configured so that a user or the manufacturer of the device can specify how many samples shall be taken from each source for averaging. For instance, a user can configure the system to take 512 samples from the roes current input, 64 samples from the battery voltage, 64 from the charger input voltage, 32 samples from the external pins and 8 from the NTC pin. Furthermore, the user can also specify if one of the above-mentioned sources shall be skipped. In some examples, the hookah device 202 is configured by a user via an external computing device which communicates wirelessly with the hookah device 202 (e.g. via BLE).

In some examples, for each source the user can specify two digital thresholds which divide the full range into a plurality of zones, such as 3 zones. Subsequently the user can set the system to release an interrupt when the sampled value changes zones e.g. from a zone 2 to a zone 3.

No conventional IC available in the market today can perform the above features of the PMIC 300. Sampling with such flexibility and granularity is paramount when driving an ultrasound transducer.

In this example, the PMIC 300 comprises an 8 bit general purpose digital input output port (GPIO). Each port can be configured as digital input and digital output. Some of the ports have an analogue input function, as shown in the table in FIG. 35.

The GPIO7-GPIO5 ports of the PMIC 300 can be used to set the device's address on the communication (I2C) bus 302. Subsequently eight identical devices can be used on the same I2C bus. This is a unique feature in the IC industry since it allows eight identical devices to be used on the same I2C bus without any conflicting addresses. This is implemented by each device reading the state of GPIO7-GPIO5 during the first 100 μs after the startup of the PMIC 300 and storing that portion of the address internally in the PMIC 300. After the PMIC 300 has been started up the GPIOs can be used for any other purpose.

As described above, the PMIC 300 comprises a six channel LED driver 320. In this example the LED driver 320 comprises N-Channel Metal-Oxide Semiconductor (NMOS) current sources which are 5V tolerant. The LED driver 320 is configured to set the LED current in four discrete levels; 5 mA, 10 mA, 15 mA and 20 mA. The LED driver 320 is configured to dim each LED channel with a 12 bit PWM signal either with or without gamma correction. The LED driver 320 is configured to vary the PWM frequency from 300 Hz to 1.5 KHz. This feature is unique in the field of ultrasonic mist inhaler devices as the functionality is embedded as a sub-system of the PMIC 300.

In this example, the PMIC 300 comprises two independent 6 Bit Digital to Analog Converters (DAC) 327, 328 which are incorporated into the PMIC 300. The purpose of the DACs 327, 328 is to output an analogue voltage to manipulate the feedback path of an external regulator (e.g. the DC-DC Boost converter 305 a Buck converter or a LDO). Furthermore, in some examples, the DACs 327, 328 can also be used to dynamically adjust the over current shutdown level of the bridge IC 301, as described below.

The output voltage of each DAC 327, 328 is programmable between 0V and 1.5V or between 0V and V battery (Vbat). In this example, the control of the DAC output voltage is done via I2C commands. Having two DAC incorporated in the PMC 300 is unique and will allow the dynamic monitoring control of the current. If either DAC 327, 328 was an external chip, the speed would fall under the same restrictions of speed limitations due to the I2C protocol. The active power monitoring arrangement of the device 202 works with optimum efficiency if all these embedded features are in the PMIC. Had they been external components, the active power monitoring arrangement would be totally inefficient.

Figure 36:
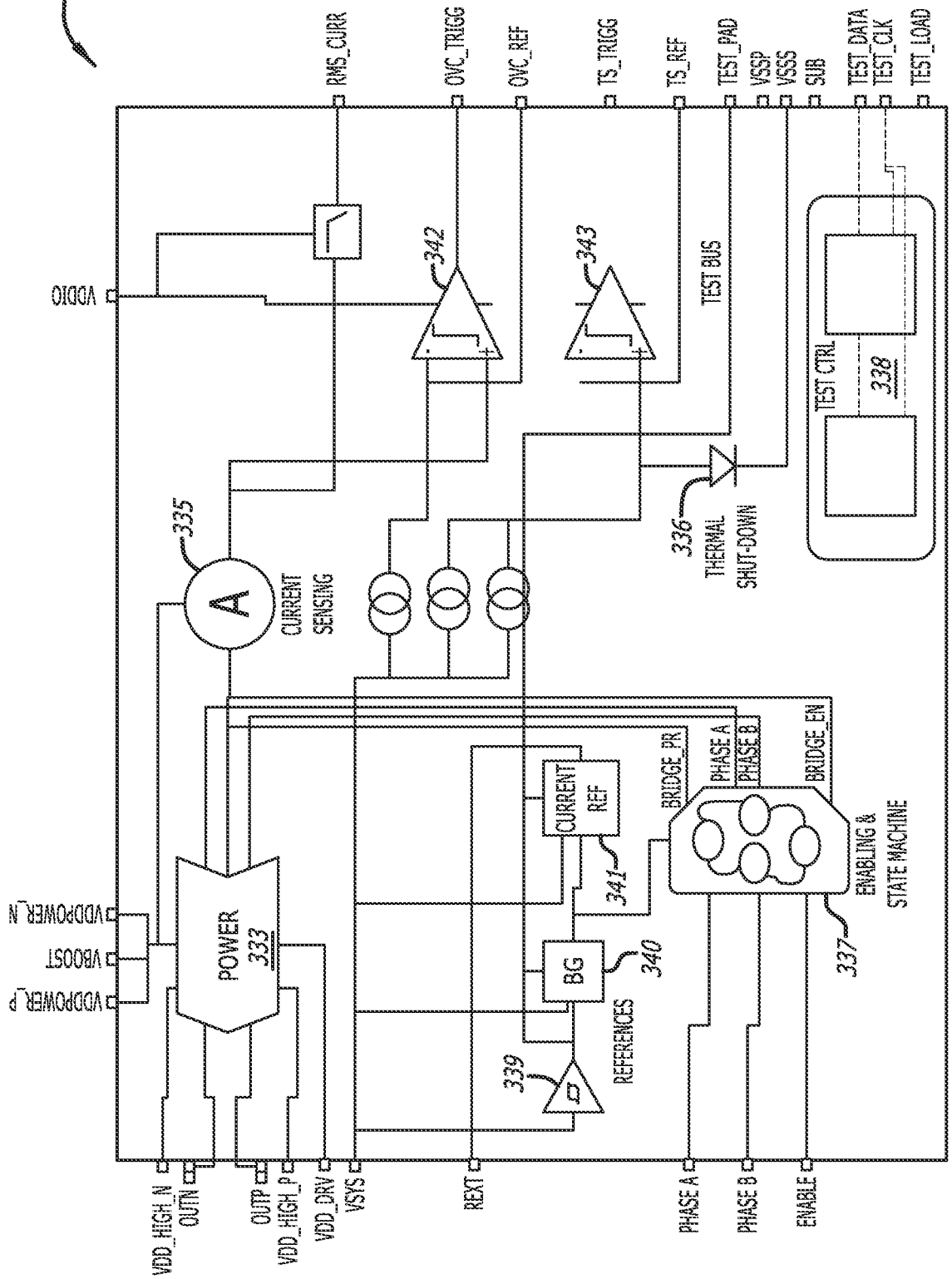
FIG. 36 is a schematic diagram of an integrated circuit of this disclosure.
Figure 37:
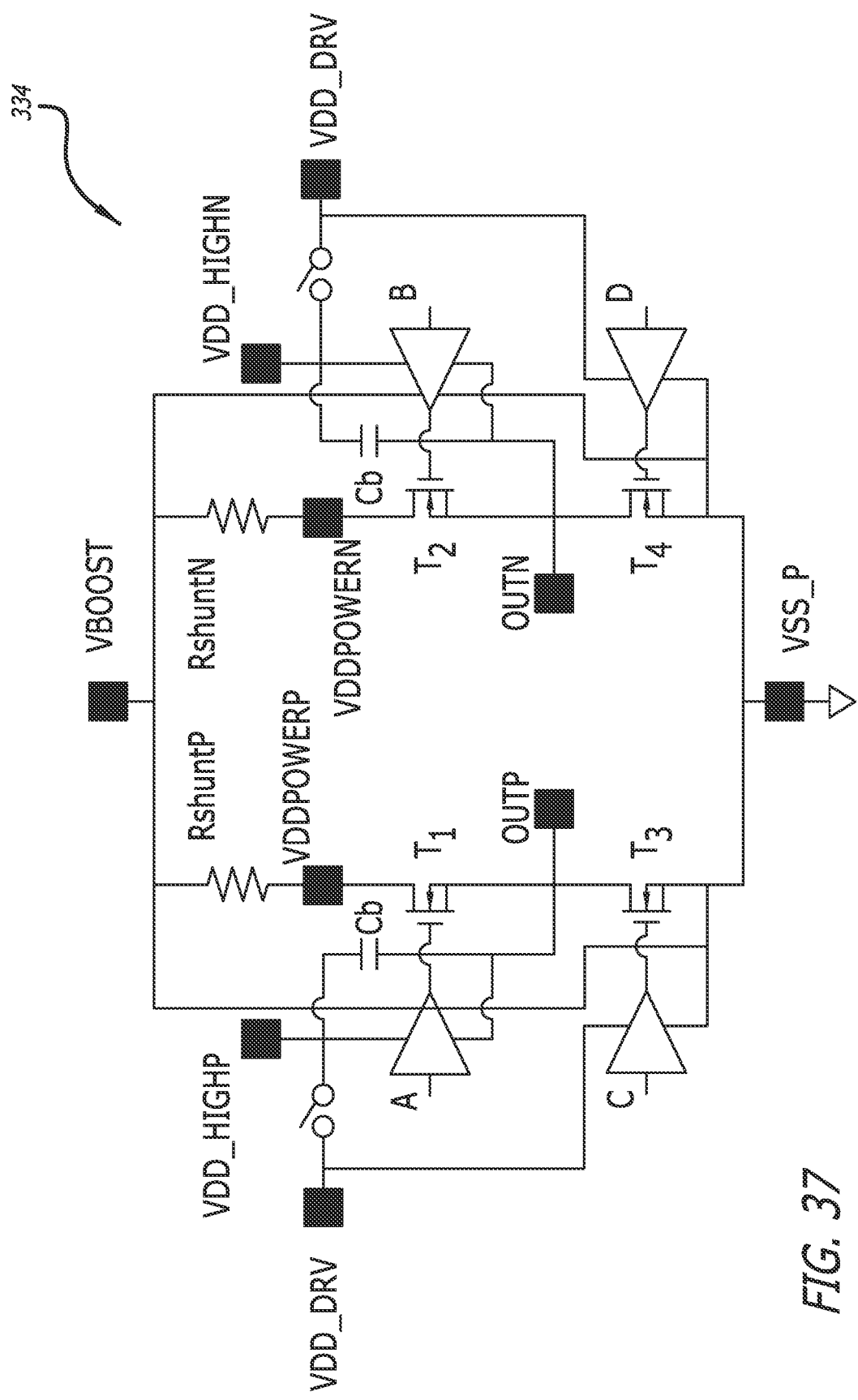
FIG. 37 is a circuit diagram of an H-bridge of an example of this disclosure.

Referring now to FIG. 36 of the accompanying drawings, the bridge IC 301 is a microchip which comprises an embedded power switching circuit 333, In this example, the power switching circuit 333 is an H-bridge 334 which is shown in FIG. 37 and which is described in detail below. It is, however, to be appreciated that the bridge IC 301 of other examples may incorporate an alternative power switching circuit to the H-bridge 334, provided that the power switching circuit performs an equivalent function for generating an AC drive signal to drive the ultrasonic transducer 215.

The bridge IC 301 comprises a first phase terminal PHASE A which receives a first phase output signal Phase A from the PWM signal generator subsystem of the PMIC 300. The bridge IC 301 also comprises a second phase terminal PHASE B which receives a second phase output signal Phase B from the PWM signal generator subsystem of the PMC 300.

The bridge IC 301 comprises a current sensing circuit 335 which senses current flow in the H-bridge 334 directly and provides an RMS current output signal via the RMS_CURR pin of the bridge IC 301. The current sensing circuit 335 is configured for over current monitoring, to detect when the current flowing in the H-bridge 334 is above a predetermined threshold. The integration of the power switching circuit 333 comprising the H-bridge 334 and the current sensing circuit 335 all within the same embedded circuit of the bridge IC 301 is a unique combination in the IC market. At present, no other integrated circuit in the IC market comprises an H-bridge with embedded circuitry for sensing the RMS current flowing through the H-bridge.

The bridge IC 301 comprises a temperature sensor 336 which includes over temperature monitoring. The temperature sensor 336 is configured to shut down the bridge IC 301 or disable at least part of the bridge IC 336 in the event that the temperature sensor 336 detects that the bridge IC 301 is operating at a temperature above a predetermined threshold. The temperature sensor 336 therefore provides an integrated safety function which prevents damage to the bridge IC 301 or other components within the hookah device 202 in the event that the bridge IC 301 operates at an excessively high temperature.

The bridge IC 301 comprises a digital state machine 337 which is integrally connected to the power switching circuit 333. The digital state machine 337 receives the phase A and phase B signals from the PMIC 300 and an ENABLE signal, for instance from the microcontroller 303. The digital state machine 337 generates timing signals based on the first phase output signal Phase A and the second phase output signal Phase B.

The digital state machine 337 outputs timing signals corresponding to the phase A and phase B signals as well as a BRIDGE_PR and BRIDGE_EN signals to the power switching circuit 333 in order to control the power switching circuit 333. The digital state machine 337 thus outputs the timing signals to the switches $T_1$-$T_4$ of the H-bridge circuit 334 to control the switches $T_1$-$T_4$ to turn on and off in a sequence such that the H-bridge circuit outputs an AC drive signal for driving a resonant circuit, such as the ultrasonic transducer 215.

As described in more detail below, the switching sequence comprises a free-float period in which the first switch $T_1$ and the second switch $T_2$ are turned off and the third switch $T_3$ and the fourth switch $T_4$ are turned on in order to dissipate energy stored by the resonant circuit (the ultrasonic transducer 215).

The bridge IC 301 comprises a test controller 338 which enables the bridge IC 301 to be tested to determine whether the embedded components within the bridge IC 301 are operating correctly. The test controller 338 is coupled to TEST_DATA, TEST_CLK and TEST_LOAD pins so that the bridge IC 301 can be connected to an external control device which feeds data into and out from the bridge IC 301 to test the operation of the bridge IC 301. The bridge IC 301 also comprises a TEST BUS which enables the digital communication bus within the bridge IC 301 to be tested via a TST_PAD pin.

The bridge IC 301 comprises a power on reset circuit (POR) 339 which controls the startup operation of the bridge IC 301. The POR 339 ensures that the bridge IC 301 starts up properly only if the supply voltage is within a predetermined range. If the power supply voltage is outside of the predetermined range, for instance if the power supply voltage is too high, the POR 339 delays the startup of the bridge IC 301 until the supply voltage is within the predetermined range.

The bridge IC 301 comprises a reference block (BG) 340 which provides a precise reference voltage for use by the other subsystems of the bridge IC 301.

The bridge IC 301 comprises a current reference 341 which provides a precise current to the power switching circuit 333 and/or other subsystems within the bridge IC 301 such as the current sensor 335.

The temperature sensor 336 monitors the temperature of the silicon of the bridge IC 301 continuously. If the temperature exceeds the predetermined temperature threshold, the power switching circuit 333 is switched off automatically. In addition, the over temperature may be reported to an external host to inform the external host that an over temperature event has occurred.

The digital state machine (FSM) 337 generates the timing signals for the power switching circuit 333 which, in this example, are timing signals for controlling the H-bridge 334.

The bridge IC 301 comprises comparators 342,343 which compare signals from the various subsystems of the bridge IC 301 with the voltage and current references 340,341 and provide reference output signals via the pins of the bridge IC 301.

Referring again to FIG. 37 of the accompanying drawings, the H-bridge 334 of this example comprises four switches in the form of NMOS field effect transistors (FET) switches on both sides of the H-bridge 334. The H-bridge 334 comprises four switches or transistors $T_1$-$T_4$ which are connected in an H-bridge configuration, with each transistor $T_1$-$T_4$ being driven by a respective logic input A-D. The transistors $T_1$-$T_4$ are configured to be driven by a bootstrap voltage which is generated internally with two external capacitors Cb which are connected as illustrated in FIG. 37.

The H-bridge 334 comprises various power inputs and outputs which are connected to the respective pins of the bridge IC 301. The H-bridge 334 receives the programmable voltage VBOOST which is output from the boost converter 305 via a first power supply terminal, labelled VBOOST in FIG. 37. The H-bridge 334 comprises a second power supply terminal, labelled VSS_P in FIG. 37.

The H-bridge 334 comprises outputs OUTP, OUTN which are configured to connect to respective terminals of the ultrasonic transducer 215 so that the AC drive signal output from the H-bridge 334 can drive the ultrasonic transducer 215.

The switching of the four switches or transistors $T_1$-$T_4$ is controlled by switching signals from the digital state machine 337 via the logic input A-D. It is to be appreciated that, while FIG. 37 shows four transistors $T_1$-$T_4$, in other examples, the H-bridge 334 incorporates a larger number of transistors or other switching components to implement the functionality of the H-bridge.

In this example, the H-bridge 334 operates at a switching power of 22 W to 37 in in order to deliver an AC drive signal with sufficient power to drive the ultrasonic transducer 215 to generate mist optimally. The voltage which is switched by the H-bridge 334 of this example is ±15 V. In other examples, the voltage is ±20 V.

In this example, the H-bridge 334 switches at a frequency of 3 MHz to 5 MHz or up to 105 MHz. This is a high switching speed compared with conventional integrated circuit H-bridges which are available in the IC market. For instance, a conventional integrated circuit H-bridge available in the IC market today is configured to operate at a maximum frequency of only 2 MHz. Aside from the bridge IC 301 described herein, no conventional integrated circuit H-bridge available in the IC market is able to operate at a power of 22 V to 37 V at a frequency of up to 5 MHz, let alone up to 105 MHz.

Figure 38:
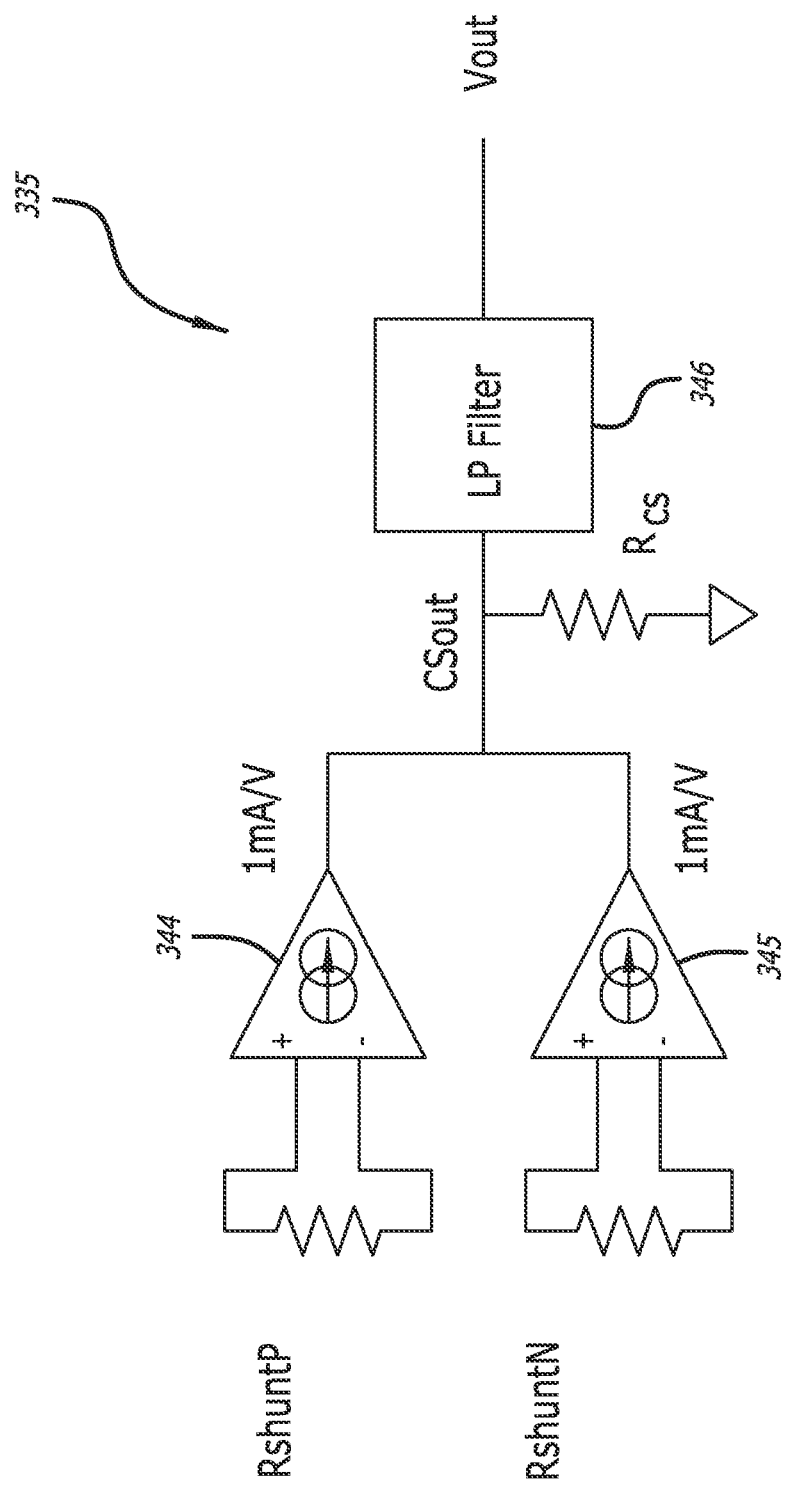
FIG. 38 is a circuit diagram of a current sense arrangement of an example of this disclosure.

Referring now to FIG. 38 of the accompanying drawings, the current sensor 335 comprises positive and negative current sense resistors RshuntP, RshuntN which are connected in series with the respective high and low sides of the H-bridge 334, as shown in FIG. 37. The current sense resistors RshuntP, RshuntN are low value resistors which, in this example, are 0.1 Ω. The current sensor 335 comprises a first voltage sensor in the form of a first operational amplifier 344 which measures the voltage drop across the first current sense resistor RshuntP and a second voltage sensor in the form of a second operational amplifier 345 which measures the voltage drop across the second current sensor resistor RshuntN. In this example, the gain of each operational amplifier 344, 345 is 2V/V. The output of each operational amplifier 344, 345 is, in this example, 1 mAN. The current sensor 335 comprises a pull down resistor $R_{CS}$ which, in this example, is 2 kΩ. The outputs of the operational amplifiers 344, 345 provide an output CSout which passes through a low pass filter 346 which removes transients in the signal CSout. An output Vout of the low pass filter 346 is the output signal of the current sensor 335.

The current sensor 335 thus measures the AC current flowing through the H-bridge 334 and respectively through the ultrasonic transducer 215. The current sensor 335 translates the AC current into an equivalent RMS output voltage (Vout) relative to ground. The current sensor 335 has high bandwidth capability since the H-bridge 334 can be operated at a frequency of up to 5 MHz or, in some examples, up to 105 MHz. The output Vout of the current sensor 335 reports a positive voltage which is equivalent to the measured AC rms current flowing through the ultrasonic transducer 215. The output voltage Vout of the current sensor 335 is, in this example, fed back to the control circuitry within the bridge IC 301 to enable the bridge IC 301 to shut down the H-bridge 334 in the event that the current flowing through the H-bridge 334 and hence through the transducer 215 is in excess of a predetermined threshold. In addition, the over current threshold event is reported to the first comparator 342 in the bridge IC 301 so that the bridge IC 301 can report the over current event via the OVC_TRIGG pin of the bridge IC 301.

Figure 39:
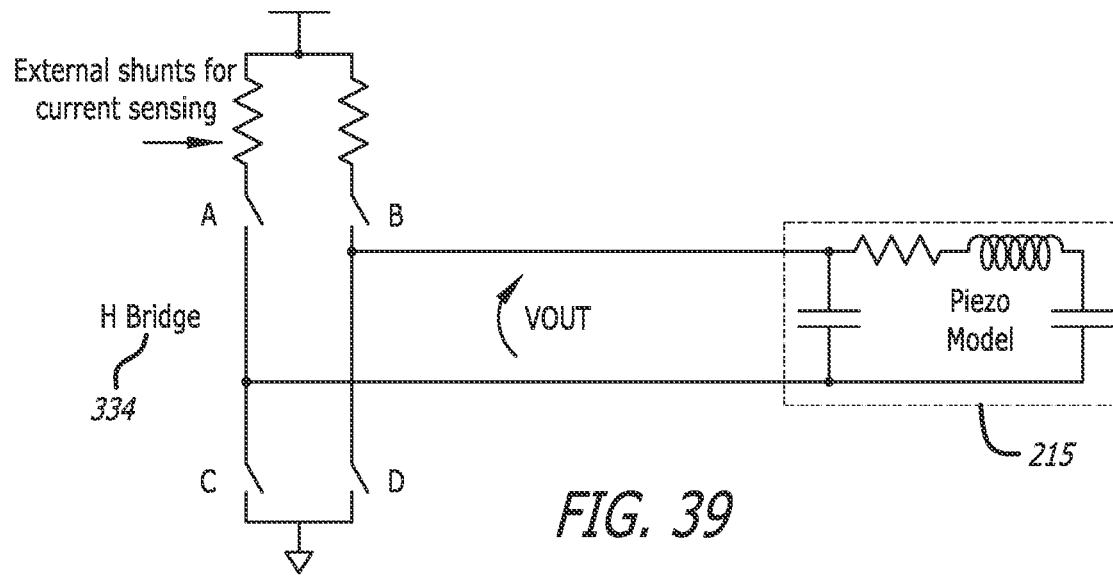
FIG. 39 is a circuit diagram of an H-bridge of an example of this disclosure.

Referring now to FIG. 39 of the accompanying drawings, the control of the H-bridge 334 will now be described also with reference to the equivalent piezoelectric model of the ultrasonic transducer 215.

To develop a positive voltage across the outputs OUTP, OUTN of the H-bridge 334 as indicated by V_out in FIG. 39 (note the direction of the arrow) the switching sequence of the transistors $T_1$-$T_4$ via the inputs A-D is as follows:

1. Positive output voltage across the ultrasonic transducer 215: A-ON, B-OFF, C-OFF, D-ON
2. Transition from positive output voltage to zero: A-OFF, B-OFF, C-OFF, D-ON. During this transition, C is switched off first to minimise or avoid power loss by minimising or avoiding current flowing through A and C if there is a switching error or delay in A.
3. Zero output voltage: A-OFF, B-OFF, C-ON, D-ON. During this zero output voltage phase, the terminals of the outputs OUTP, OUTN of the H-bridge 334 are grounded by the C and D switches which remain on. This dissipates the energy stored by the capacitors in the equivalent circuit of the ultrasonic transducer, which minimises the voltage overshoot in the switching waveform voltage which is applied to the ultrasonic transducer.
4. Transition from zero to negative output voltage: A-OFF, B-OFF, C-ON, D-OFF.
5. Negative output voltage across the ultrasonic transducer 215: A-OFF, B-ON, C-ON, D-OFF At high frequencies of up to 5 MHz or even up to 105 MHz, it will be appreciated that the time for each part of the switching sequence is very short and in the order of nanoseconds or picoseconds. For instance, at a switching frequency of 6 MHz, each part of the switching sequence occurs in approximately 80 ns.

Figure 40:
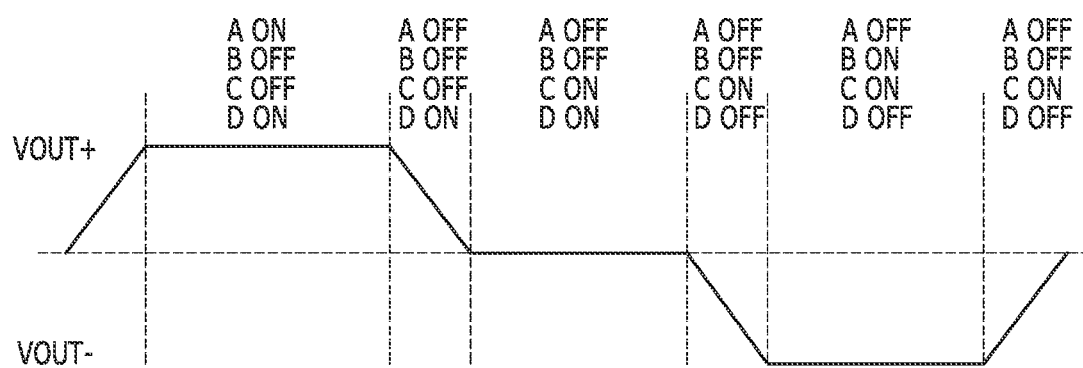
FIG. 40 is a graph showing the voltages during the phases of operation of the H-bridge of FIG. 37.

A graph showing the output voltage OUTP, OUTN of the H-bridge 334 according to the above switching sequence is shown in FIG. 40 of the accompanying drawings. The zero output voltage portion of the switching sequence is included to accommodate for the energy stored by the ultrasonic transducer 215 (e.g. the energy stored by the capacitors in the equivalent circuit of the ultrasonic transducer). As described above, this minimises the voltage overshoot in the switching waveform voltage which is applied to the ultrasonic transducer and hence minimises unnecessary power dissipation and heating in the ultrasonic transducer.

Minimising or removing voltage overshoot also reduces the risk of damage to transistors in the bridge IC 301 by preventing the transistors from being subject to voltages in excess of their rated voltage. Furthermore, the minimisation or removal of the voltage overshoot enables the bridge IC 301 to drive the ultrasonic transducer accurately in a way which minimises disruption to the current sense feedback loop described herein. Consequently, the bridge IC 301 is able to drive the ultrasonic transducer at a high power of 22 W to 50 W or even as high as 70 W at a high frequency of up to 5 MHz or even up to 105 MHz.

The bridge IC 301 of this example is configured to be controlled by the PMIC 300 to operate in two different modes, referred to herein as a forced mode and a native frequency mode. These two modes of operation are novel over existing bridge ICs. In particular, the native frequency mode is a major innovation which offers substantial benefits in the accuracy and efficiency of driving an ultrasonic transducer as compared with conventional devices.

Forced Frequency Mode (FFM)

In the forced frequency mode the H-bridge 334 is controlled in the sequence described above but at a user selectable frequency. As a consequence, the H-bridge transistors $T_1$-$T_4$ are controlled in a forced way irrespective of the inherent resonant frequency of the ultrasonic transducer 215 to switch the output voltage across the ultrasonic transducer 215. The forced frequency mode therefore allows the H-bridge 334 to drive the ultrasonic transducer 215, which has a resonant frequency f1, at different frequency f2.

Driving an ultrasonic transducer at a frequency which is different from its resonant frequency may be appropriate in order to adapt the operation to different applications. For example, it may be appropriate to drive an ultrasonic transducer at a frequency which is slightly off the resonance frequency (for mechanical reasons to prevent mechanical damage to the transducer). Alternatively, it may be appropriate to drive an ultrasonic transducer at a low frequency but the ultrasonic transducer has, because of its size, a different native resonance frequency.

The hookah device 202 controls the bridge IC 301 to drive the ultrasonic transducer 215 in the forced frequency mode in response to the configuration of the hookah device 202 for a particular application or a particular ultrasonic transducer. For instance, the hookah device 202 may be configured to operate in the forced frequency mode when the mist inhaler device 200 is being used for a particular application, such as generating a mist from a liquid of a particular viscosity containing a drug for delivery to a user.

Native Frequency Mode (NFM)

The following native frequency mode of operation is a significant development and provides benefits in improved accuracy and efficiency over conventional ultrasonic drivers that are available on the IC market today.

The native frequency mode of operation follows the same switching sequence as described above but the timing of the zero output portion of the sequence is adjusted to minimise or avoid problems that can occur due to current spikes in the forced frequency mode operation. These current spikes occur when the voltage across the ultrasonic transducer 215 is switched to its opposite voltage polarity. An ultrasonic transducer which comprises a piezoelectric crystal has an electrical equivalent circuit which incorporates a parallel connected capacitor (e.g. see the piezo model in FIG. 39). If the voltage across the ultrasonic transducer is hard-switched from a positive voltage to a negative voltage, due to the high dV/dt there can be a large current flow current flow as the energy stored in the capacitor dissipates.

The native frequency mode avoids hard switching the voltage across the ultrasonic transducer 215 from a positive voltage to a negative voltage (and vice versa). Instead, prior to applying the reversed voltage, the ultrasonic transducer 215 (piezoelectric crystal) is left free-floating with zero voltage applied across its terminals for a free-float period. The PMIC 300 sets the drive frequency of the bridge IC 301 such that the bridge 334 sets the free-float period such that current flow inside the ultrasonic transducer 215 (due to the energy stored within the piezoelectric crystal) reverses the voltage across the terminals of the ultrasonic transducer 215 during the free-float period.

Consequently, when the H-bridge 334 applies the negative voltage at the terminals of the ultrasonic transducer 215 the ultrasonic transducer 215 (the capacitor in the equivalent circuit) has already been reverse charged and no current spikes occur because there is no high dV/dt.

It is, however, to be appreciated that it takes time for the charge within the ultrasonic transducer 215 (piezoelectric crystal) to build up when the ultrasonic transducer 215 is first activated. Therefore, the ideal situation in which the energy within the ultrasonic transducer 215 is to reverse the voltage during the free-float period occurs only after the oscillation inside the ultrasonic transducer 215 has built up the charge. To accommodate for this, when the bridge IC 301 activates the ultrasonic transducer 215 for the first time, the PMIC 300 controls the power delivered through the H-bridge 334 to the ultrasonic transducer 215 to a first value which is a low value (e.g. 5 V), The PMIC 300 then controls the power delivered through the H-bridge 334 to the ultrasonic transducer 215 to increase over a period of time to a second value (e.g. 15 V) which is higher than the first value in order to build up the energy stored within the ultrasonic transducer 215. Current spikes still occur during this ramp of the oscillation until the current inside the ultrasonic transducer 215 developed sufficiently. However, by using a low first voltage at start up those current spikes are kept sufficiently low to minimise the impact on the operation of the ultrasonic transducer 215.

In order to implement the native frequency mode, the hookah device 202 controls the frequency of the oscillator 315 and the duty cycle (ratio of turn-on time to free-float time) of the AC drive signal output from the H-bridge 334 with high precision. In this example, the hookah device 202 performs three control loops to regulate the oscillator frequency and the duty cycle such that the voltage reversal at the terminals of the ultrasonic transducer 215 is as precise as possible and current spikes are minimised or avoided as far as possible. The precise control of the oscillator and the duty cycle using the control loops is a significant advance in the field of IC ultrasonic drivers.

During the native frequency mode of operation, the current sensor 335 senses the current flowing through the ultrasonic transducer 215 (resonant circuit) during the free-float period. The digital state machine 337 adapts the timing signals to switch on either the first switch $T_1$ or the second switch $T_2$ when the current sensor 335 senses that the current flowing through the ultrasonic transducer 215 (resonant circuit) during the free-float period is zero.

Figure 41:
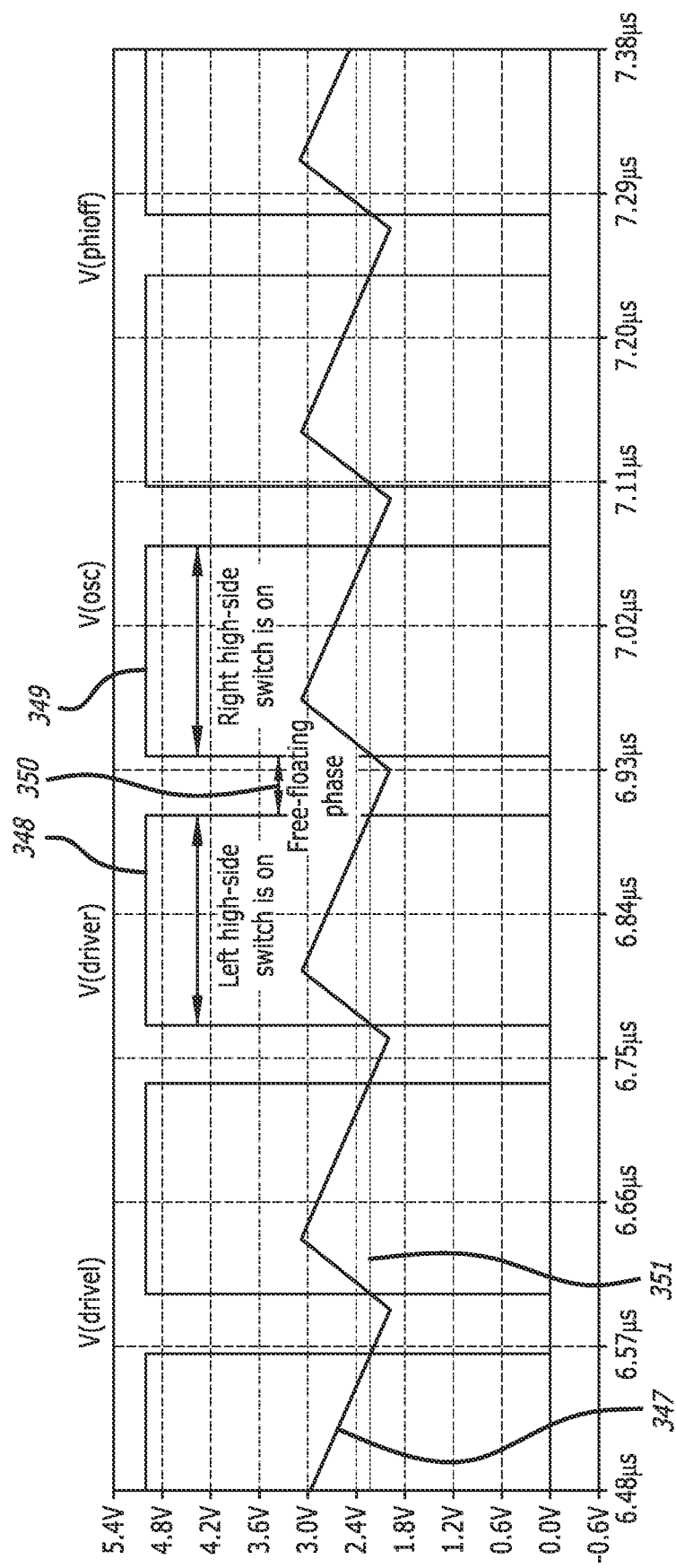
FIG. 41 is a graph showing the voltages during the phases of operation of the H-bridge of FIG. 37.

FIG. 41 of the accompanying drawings shows the oscillator voltage waveform 347 (V(osc)), a switching waveform 348 resulting from the turn-on and turn-off the left hand side high switch $T_1$ of the H-bridge 334 and a switching waveform 349 resulting from the turn-on and turn-off the right hand side high switch $T_2$ of the H-bridge 334, For an intervening free-float period 350, both high switches $T_1$, $T_2$ of the H-bridge 334 are turned off (free-floating phase). The duration of the free-float period 350 is controlled by the magnitude of the free-float control voltage 351 (Vphioff).

Figure 42:
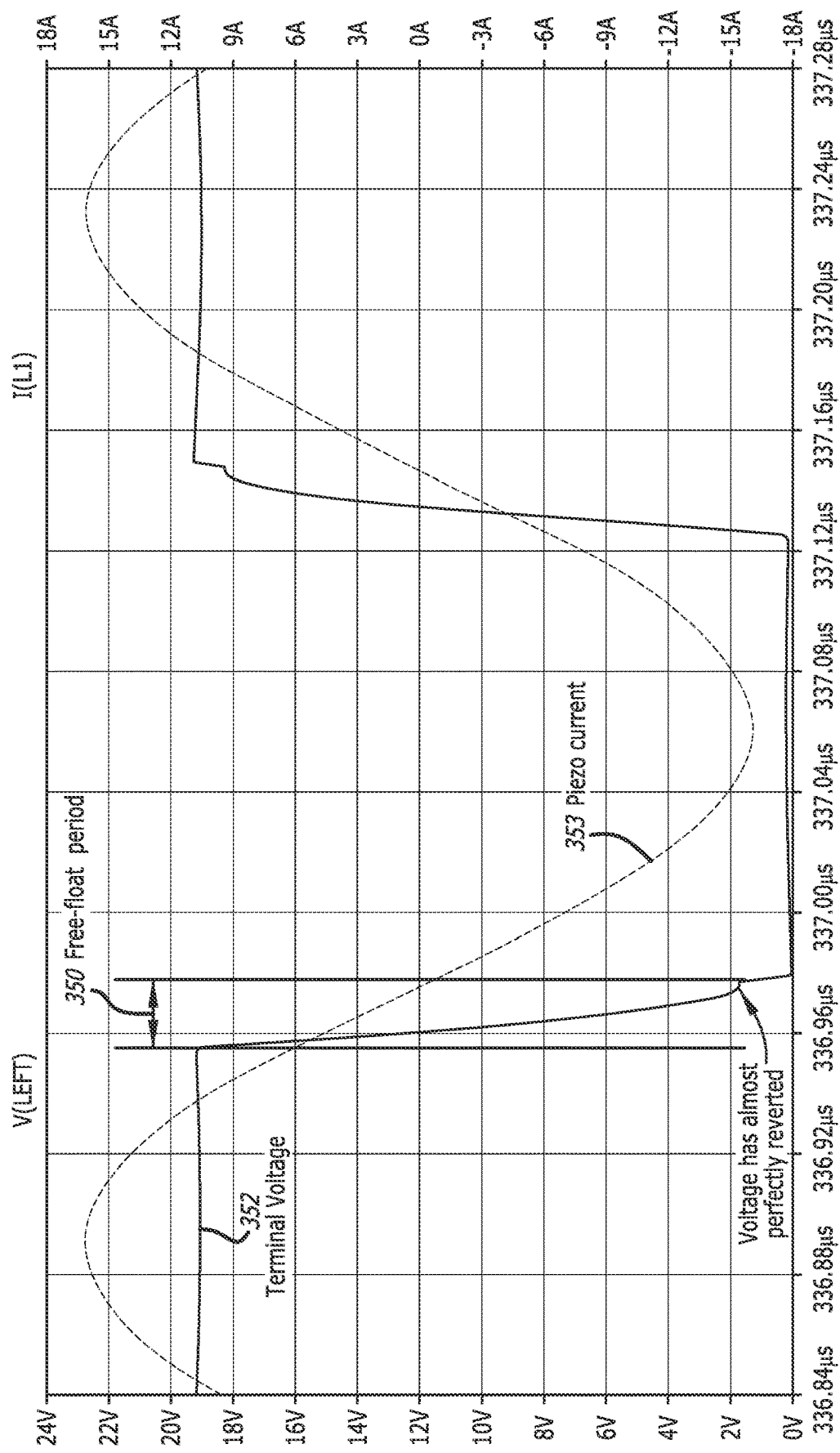
FIG. 42 is a graph showing the voltage and current at a terminal of an ultrasonic transducer while the ultrasonic transducer is being driven by the H-bridge of FIG. 37.

FIG. 42 of the accompanying drawings shows the voltage waveform 352 at a first terminal of the ultrasonic transducer 215 (the voltage waveform is reversed at the second terminal of the ultrasonic transducer 215) and the piezo current 353 flowing through the ultrasonic transducer 215. The piezo current 353 represents an (almost) ideal sinusoidal waveform (this is never possible in the forced frequency mode or in any bridge in the IC market).

Before the sinusoidal wave of the piezo current 353 reaches zero, the left hand side high switch $T_1$ of the H-bridge 334 is turned off (here, the switch $T_1$ is turned off when the piezo current 353 is approximately 6 A). The remaining piezo current 353 which flows within the ultrasonic transducer 215 due to the energy stored in the ultrasonic transducer 215 (the capacitor of the piezo equivalent circuit) is responsible for the voltage reversal during the free-float period 350. The piezo current 353 decays to zero during the free-float period 350 and into negative current flow domain thereafter. The terminal voltage at the ultrasonic transducer 215 drops from the supply voltage (in this case 19 V) to less than 2 V and the drop comes to a stop when the piezo current 353 reaches zero. This is the perfect time to turn on the low-side switch $T_3$ of the H-bridge 334 in order to minimise or avoid a current spike.

Compared to the forced frequency mode described above, the native frequency mode has at least three advantages:
1. The current spike associated with hard switching of the package capacitor is significantly reduced or avoided completely.
2. Power loss due to hard switching is almost eliminated.
3. Frequency is regulated by the control loops and will be kept close to the resonance of the piezo crystal (i.e. the native resonance frequency of the piezo crystal).

In the case of the frequency regulation by the control loops (advantage 3 above), the PMIC 300 starts by controlling the bridge IC 301 to drive the ultrasonic transducer 215 at a frequency above the resonance of the piezo crystal. The PMIC 300 then controls the bridge IC 301 to that the frequency of the AC drive signal decays/reduces during start up. As soon as the frequency approaches resonance frequency of the piezo crystal, the piezo current will develop/increase rapidly. Once the piezo current is high enough to cause the desired voltage reversal, the frequency decay/reduction is stopped by the PMIC 300. The control loops of the PMIC 300 then take over the regulation of frequency and duty cycle of the AC drive signal.

In the forced frequency mode, the power delivered to the ultrasonic transducer 215 is controlled through the duty cycle and/or a frequency shift and/or by varying the supply voltage. However, in this example in the native frequency mode the power delivered to the ultrasonic transducer 215 controlled only through the supply voltage.

In this example, during a setup phase of operation of the hookah device, the bridge IC 301 is configured to measure the length of time taken for the current flowing through the ultrasonic transducer 215 (resonant circuit) to fall to zero when the first switch $T_1$ and the second switch $T_2$ are turned off and the third switch $T_3$ and the fourth switch $T_4$ are turned on. The bridge IC 301 then sets the length of time of the free-float period to be equal to the measured length of time.

Referring now to FIG. 43 of the accompanying drawings, the PMIC 300 and the bridge IC 301 of this example are designed to work together as a companion chip set. The PMIC 300 and the bridge IC 301 are connected together electrically for communication with one another. In this example, there are interconnections between the PMIC 300 and the bridge IC 301 which enable the following two categories of communication:
1. control signals
2. feedback signals The connections between the PHASE_A and PHASE_B pins of the PMIC 300 and the bridge IC 301 carry the PWM modulated control signals which drive the H-bridge 334. The connection between the EN_BR pins of the PMIC 300 and the bridge IC 301 carries the EN_BR control signal which triggers the start of the H-bridge 334. The timing between the PHASE_A, PHASE_B and EN_BR control signals is important and handled by the digital bridge control of the PMIC 300.

The connections between the CS, OC and OT pins of the PMIC 300 and the bridge IC 301 carry CS (current sense), OC (over current) and OT (over temperature) feedback signals from the bridge IC 301 back to the PMIC 300, Most notably, the CS (current sense) feedback signal comprises a voltage equivalent to the rms current flowing through the ultrasonic transducer 215 which is measured by the current sensor 335 of the bridge IC 301.

The OC (over current) and OT (over temperature) feedback signals are digital signals indicating that either an over current or an over voltage event has been detected by the bridge IC 301. In this example, the thresholds for the over current and over temperature are set with an external resistor. Alternatively, the thresholds can also be dynamically set in response to signals passed to the OC_REF pin of the bridge IC 301 from one of the two DAC channels VDAC0, VDAC1 from the PMIC 300.

In this example, the design of the PMIC 300 and the bridge IC 301 allow the pins of these two integrated circuits to be connected directly to one another (e.g. via copper tracks on a PCB) so that there is minimal or no lag in the communication of signals between the PMIC 300 and the bridge IC 301. This provides a significant speed advantage over conventional bridges in the IC market which are typically controlled by signals via a digital communications bus. For example, a standard I2C bus is clocked at only 400 kHz, which is too slow for communicating data sampled at the high clock speeds of up to 5 MHz of examples of this disclosure.

While examples of this disclosure have been described above in relation to the microchip hardware, it is to be appreciated that other examples of this disclosure comprise a method of operating the components and subsystems of each microchip to perform the functions described herein. For instance, the methods of operating the PMIC 300 and the bridge IC 301 in either the forced frequency mode or the native frequency mode.

Figure 44:
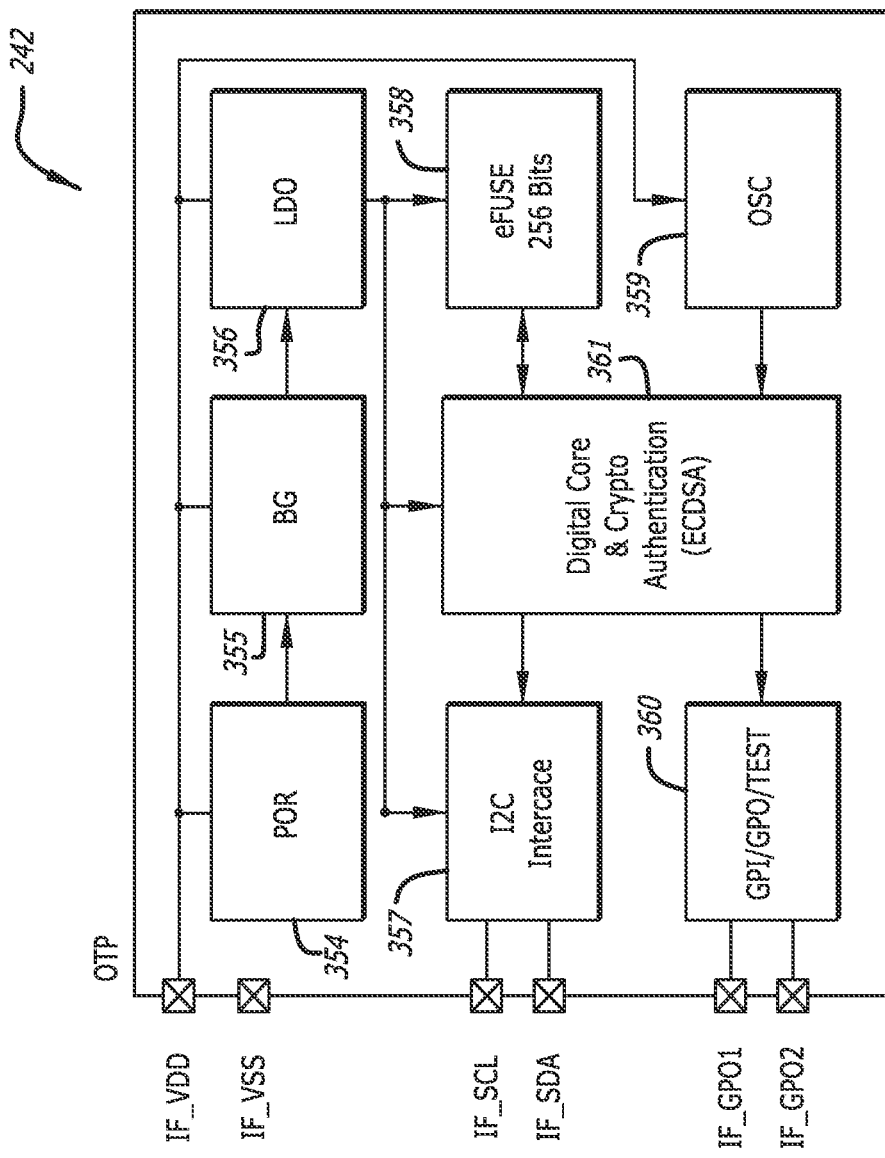
FIG. 44 is a schematic diagram of an integrated circuit of this disclosure.

Referring now to FIG. 44 of the accompanying drawings, the OTP IC 242 comprises a power on reset circuit (POR) 354, a bandgap reference (BG) 355, a cap-less low dropout regulator (LDO) 356, a communication (e.g. I2C) interface 357, a one-time programmable memory bank (eFuse) 358, an oscillator 359 and a general purpose input-output interface 360, The OTP IC 242 also comprises a digital core 361 which includes a cryptographic authenticator. In this example, the cryptographic authenticator uses the Elliptic Curve Digital Signature Algorithm (ECDSA) for encrypting/decrypting data stored within the OTP IC 242 as well as data transmitted to and from the OTP IC 242.

The POR 354 ensures that the OTP IC 242 starts up properly only if the supply voltage is within a predetermined range. If the supply voltage is outside the predetermined range, the POR 354 resets the OTP IC 242 and waits until the supply voltage is within the predetermined range.

The BG 355 provides precise reference voltages and currents to the LDO 356 and to the oscillator 359. The LDO 356 supplies the digital core 361, the communication interface 357 and the eFuse memory bank 358.

The OTP IC 242 is configured to operate in at least the following modes:

Fuse Programming (Fusing): During efuse programming (programming of the one time programmable memory) a high current is required to burn the relevant fuses within the eFuse memory bank 358. In this mode higher bias currents are provided to maintain gain and bandwidth of the regulation loop.

Fuse Reading: In this mode a medium level current is required to maintain efuse reading within the eFuse memory bank 358. This mode is executed during the startup of the OTP IC 242 to transfer the content of the fuses to shadow registers. In this mode the gain and bandwidth of the regulation loop is set to a lower value than in the Fusing Mode.

Normal Operation: In this mode the LDO 356 is driven in a very low bias current condition to operate the OTP IC 242 with low power so that the OTP IC 242 consumes as little power as possible.

The oscillator 359 provides the required clock for the digital core/engine 361 during testing (SCAN Test), during fusing and during normal operation. The oscillator 359 is trimmed to cope with the strict timing requirements during the fusing mode.

In this example, the communication interface 357 is compliant with the FM+ specification of the I2C standard but it also complies with slow and fast mode. The OTP IC 242 uses the communication interface 357 to communicate with the hookah device 202 (the Host) for data and key exchange.

The digital core 361 implements the control and communication functionality of the OTP IC 242. The cryptographic authenticator of the digital core 361 enables the OTP IC 242 to authenticate itself (e.g. using ECDSA encrypted messages) with the hookah device 202 (e.g. for a particular application) to ensure that the OTP IC 242 is genuine and that the OTP IC 242 is authorised to connect to the hookah device 202.

Figure 45:
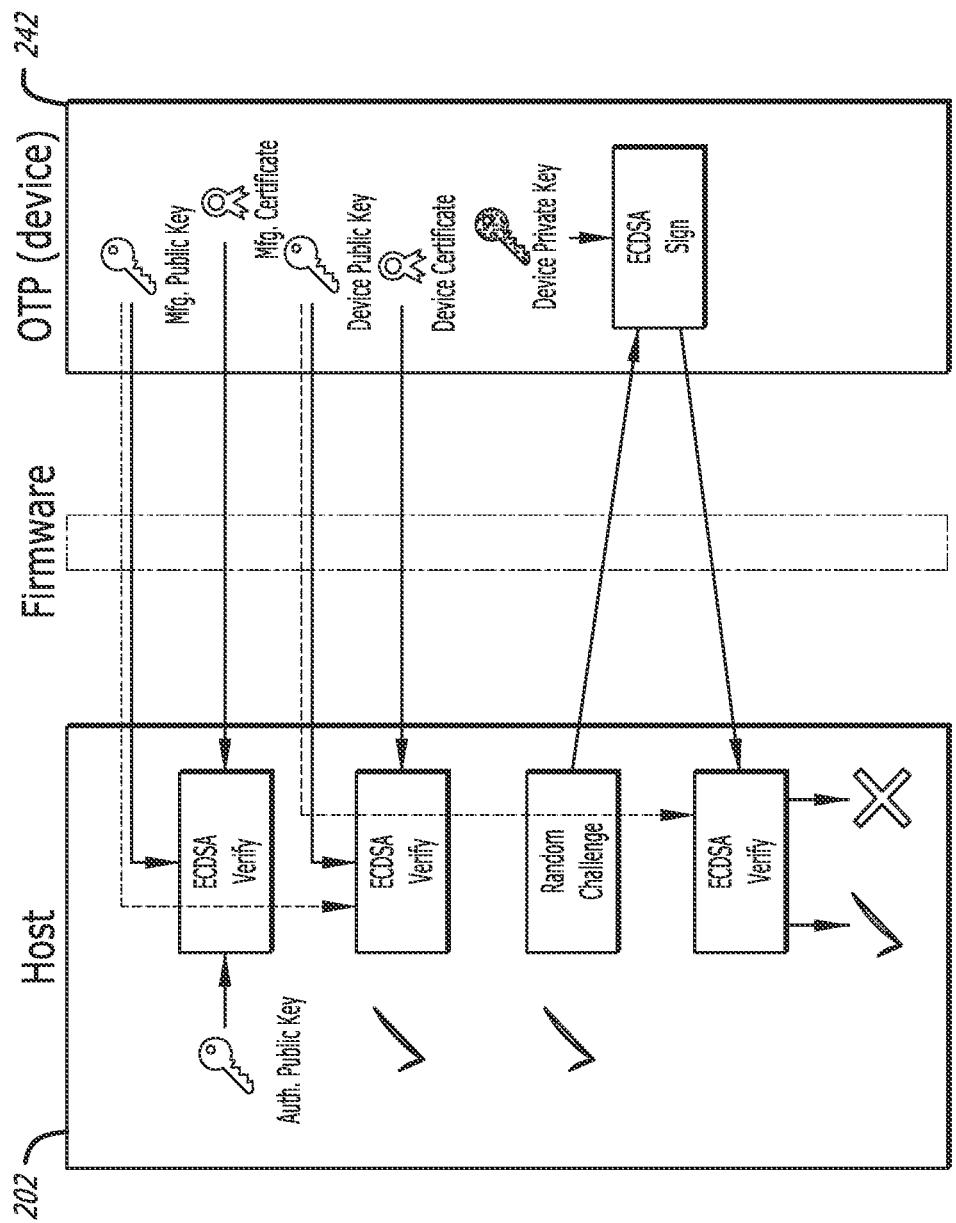
FIG. 45 is diagram illustrating the steps of an authentication method of an example of this disclosure.

With reference to FIG. 45 of the accompanying drawings, the OTP IC 242 performs the following PKI procedure in order to authenticate the OTP IC 242 for use with a Host (e.g. the hookah device 202):

1. Verify Signer Public Key: The Host requests the Manufacturing Public key and Certificate. The Host verifies the certificate with the Authority Public key.
2. Verify Device Public Key: If the verification is successful, the Host requests the Device Public key and Certificate. The Host verifies the certificate with the Manufacturing Public key.
3. Challenge—Response: If the verification is successful, the Host creates a random number challenge and sends it to the Device. The End Product signs the random number challenge with the Device Private key.
4. The signature is sent back to the Host for verification using the Device Public key.

If all steps of the authentication procedure complete successfully then the Chain of Trust has been verified back to the Root of Trust and the OTP IC 242 is successfully authenticated for use with the Host. However, if any of the steps of the authentication procedure fail then the OTP IC 242 is not authenticated for use with the Host and use of the device incorporating the OTP IC 242 is restricted or prevented.

Figure 46:
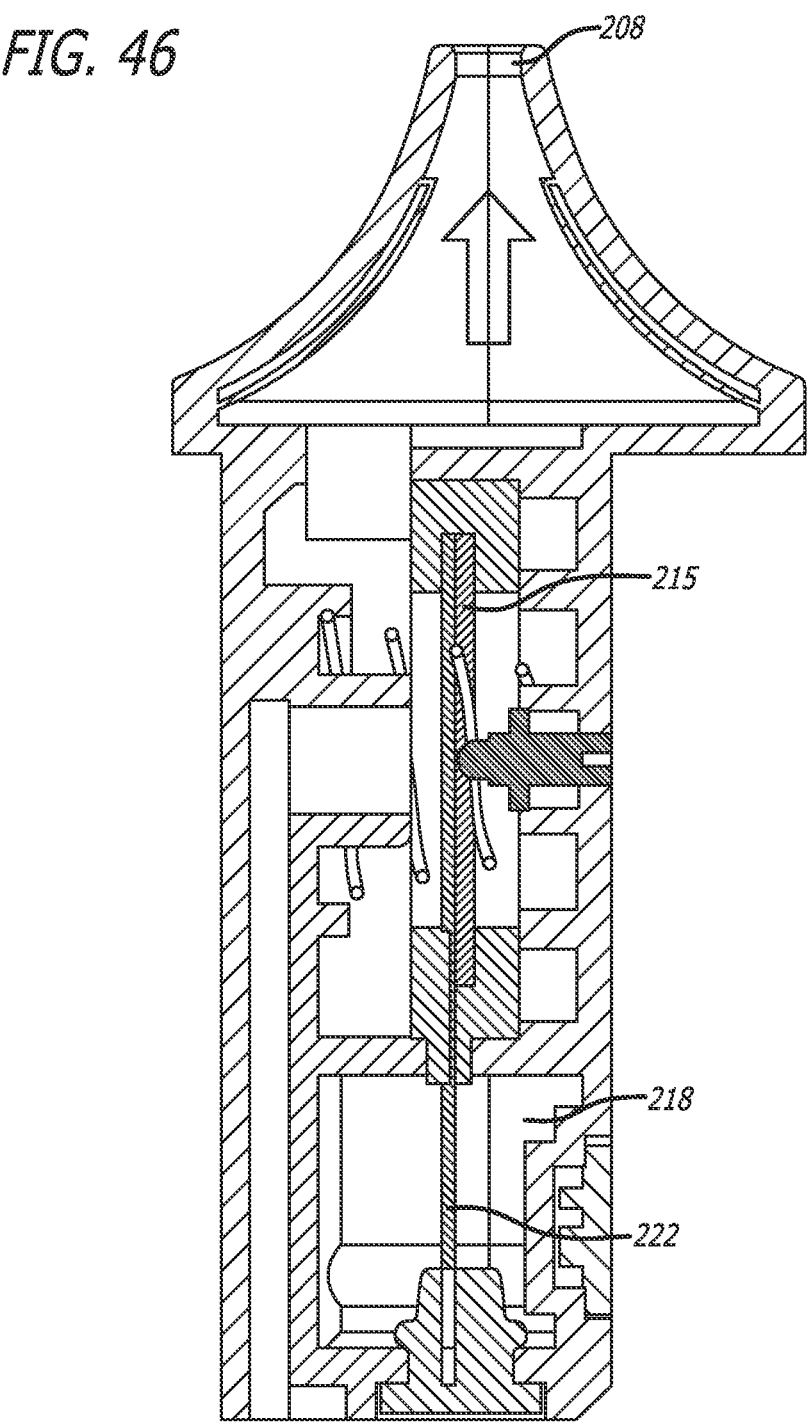
FIG. 46 is a cross sectional view of a mist generator device of this disclosure.
Figure 47:
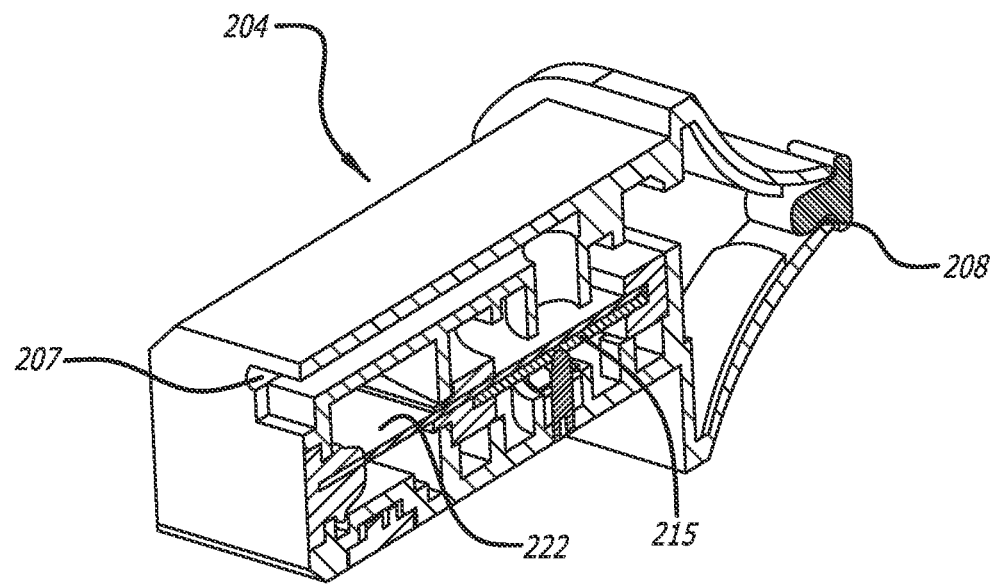
FIG. 47 is a cross sectional view of a mist generator device of this disclosure.
Figure 48:
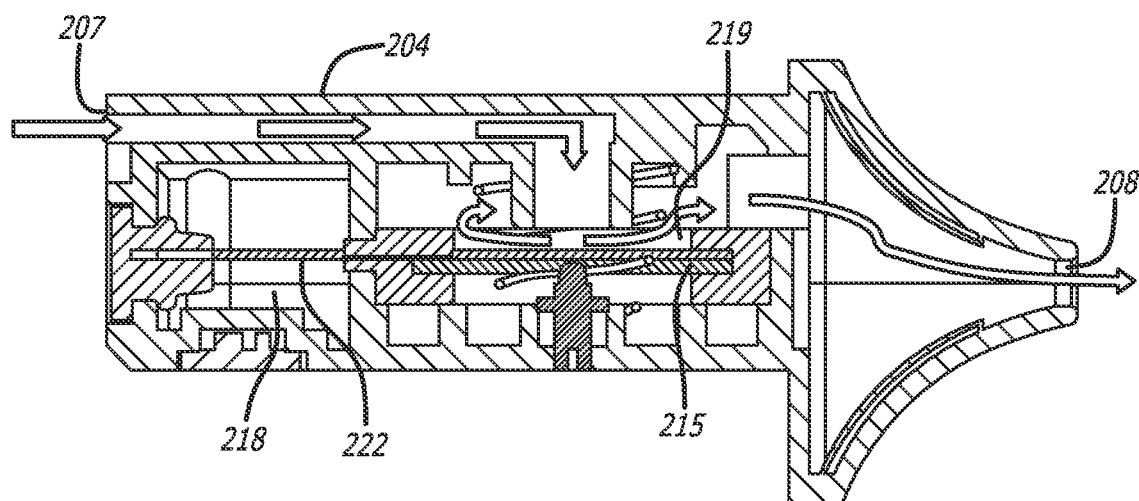
FIG. 48 is a cross sectional view of a mist generator device of this disclosure.

FIGS. 46 to 48 illustrate how air flows through the mist generator device 201 during operation.

The sonication of the liquid drug (e.g. nicotine) transforms it into mist (aerosolization). However, this mist would settle over the ultrasonic transducer 215 unless enough ambient air is available to replace the rising aerosol. In the sonication chamber 219, there is a requirement for a continuous supply of air as mist (aerosol) is generated and pulled out through the mist outlet port 208. To cater to this requirement, an airflow channel is provided. In this arrangement the airflow channel has an average cross-sectional area of 11.5 $mm^2$, which is calculated and designed into the sonication chamber 219 based on the negative air pressure from an average user. This also controls the mist-to-air ratio of the inhaled aerosol, controlling the amount of drug delivered to the user.

Based on design requirements, the air flow channel is routed such that it initiates from the bottom of the sonication chamber 219. The opening at the bottom of the aerosol chamber aligns with and is tightly adjacent to the opening to an airflow bridge in the device. The air flow channel runs vertically upwards along the reservoir and continues until the center of the sonication chamber (concentric with the ultrasonic transducer 215). Here, it turns 90° inwards. The flow path then continues on until approximately 1.5 mm from the ultrasonic transducer 215. This routing ensures maximized ambient air supplied directly in the direction of the atomization surface of the ultrasonic transducer 215. The air flows through the channel, towards the transducer, collects the generated mist as it travels out through the mist outlet port 208.

Figure 49:
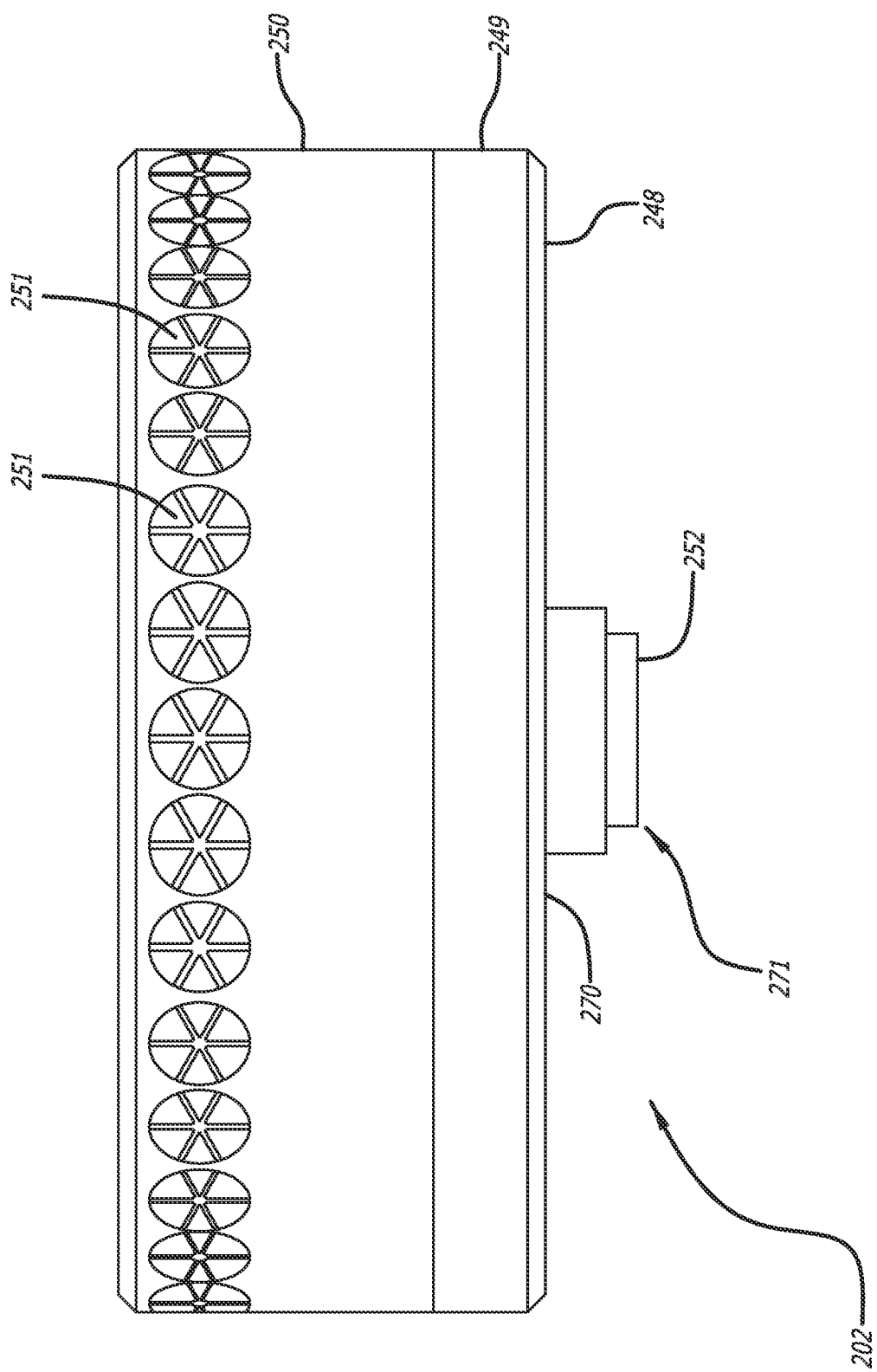
FIG. 49 is a diagrammatic perspective view of a hookah device of this disclosure.
Figure 50:
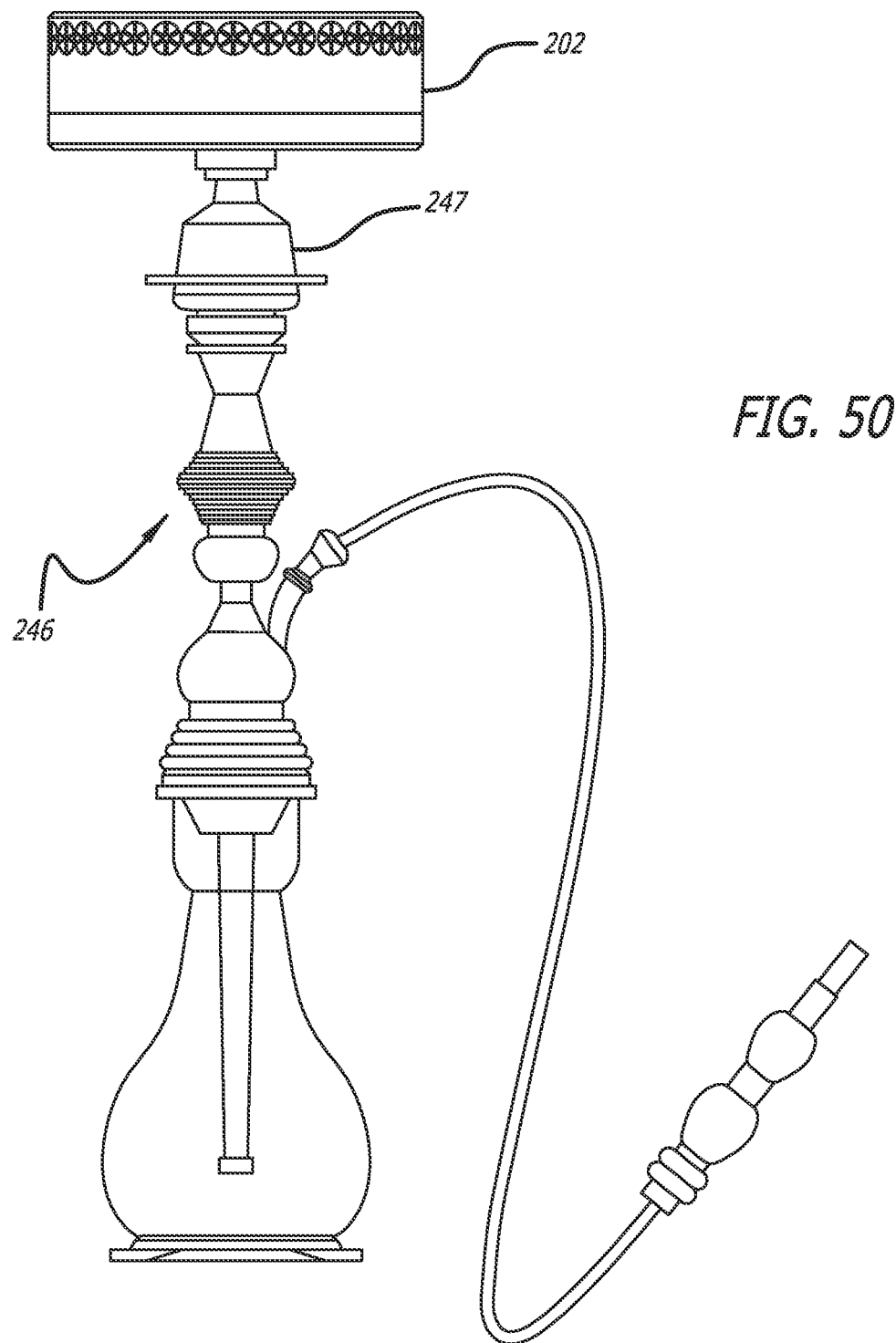
FIG. 50 is a diagrammatic perspective view of a hookah device of this disclosure attached to a hookah body and water bowl of a hookah apparatus.
Figure 51:
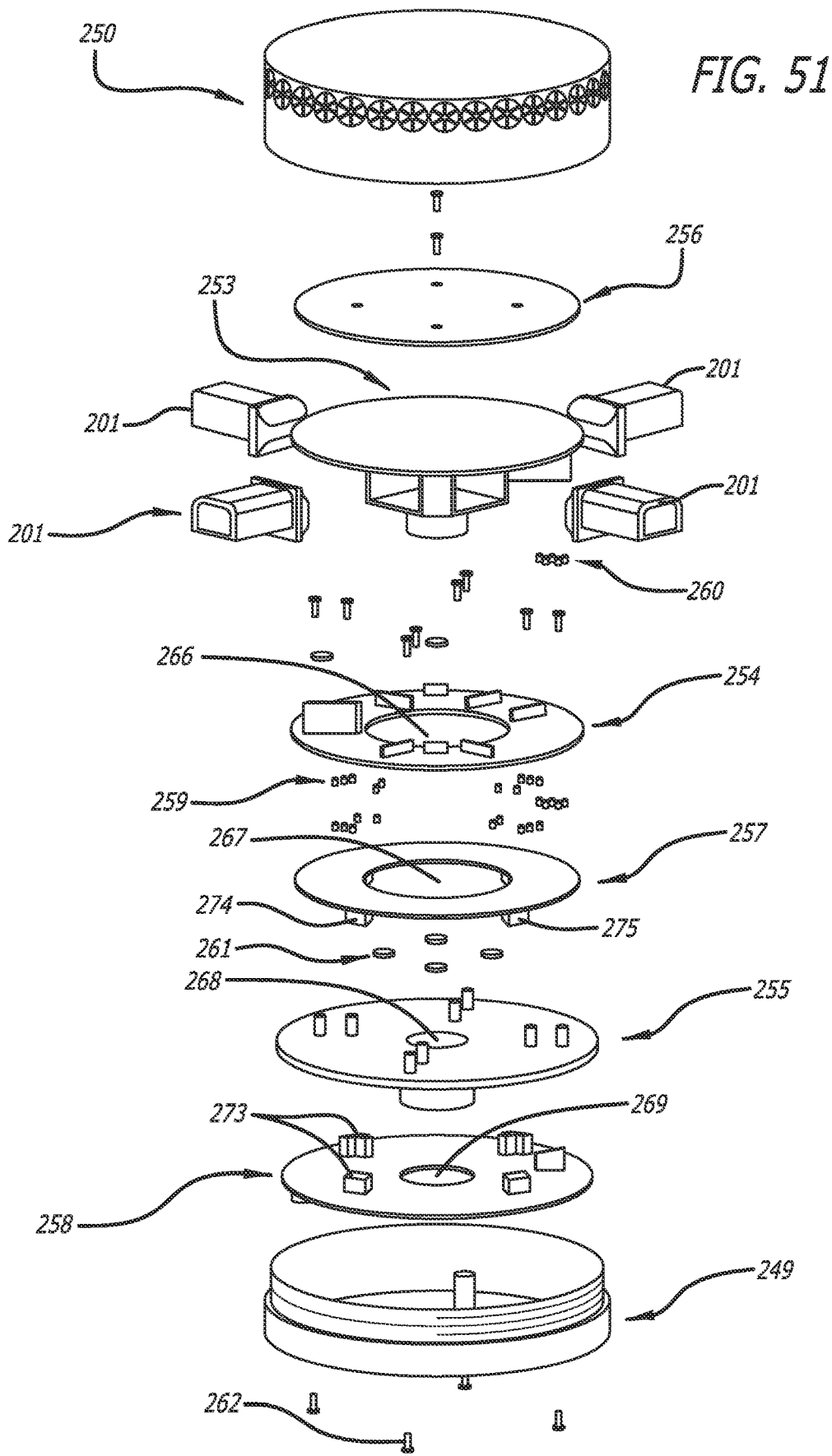
FIG. 51 is a diagrammatic exploded perspective view of a hookah device of this disclosure.
Figure 52:
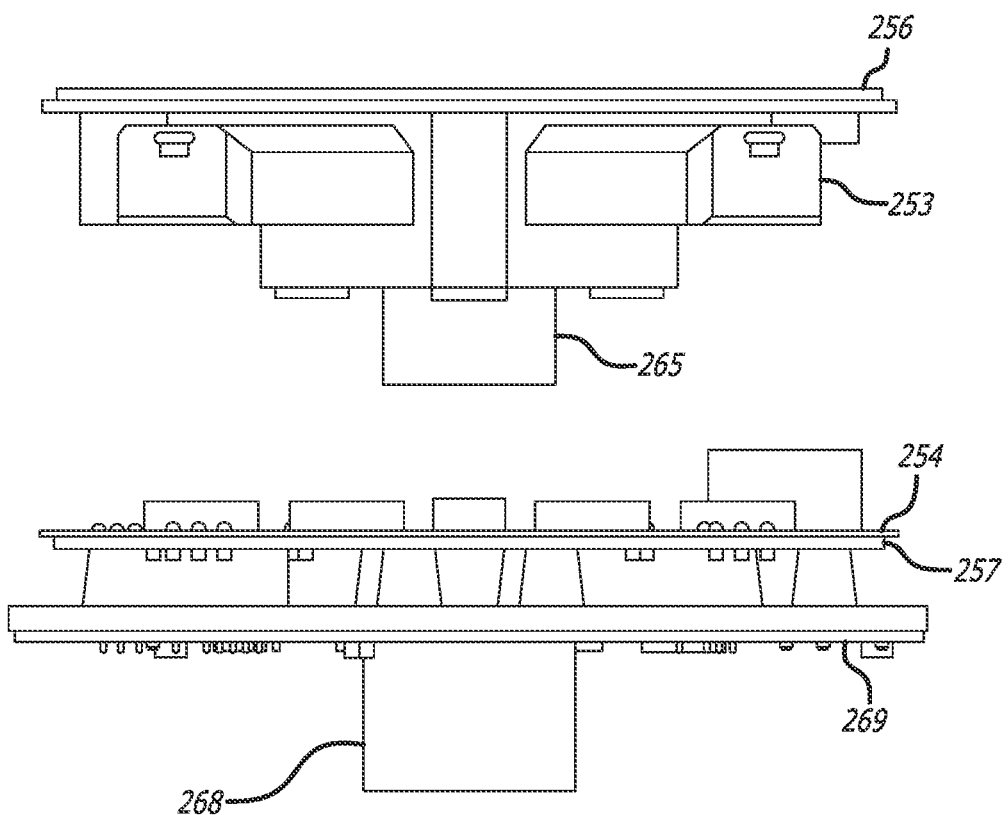
FIG. 52 is a diagrammatic perspective view of components of a hookah device of this disclosure.
Figure 53:
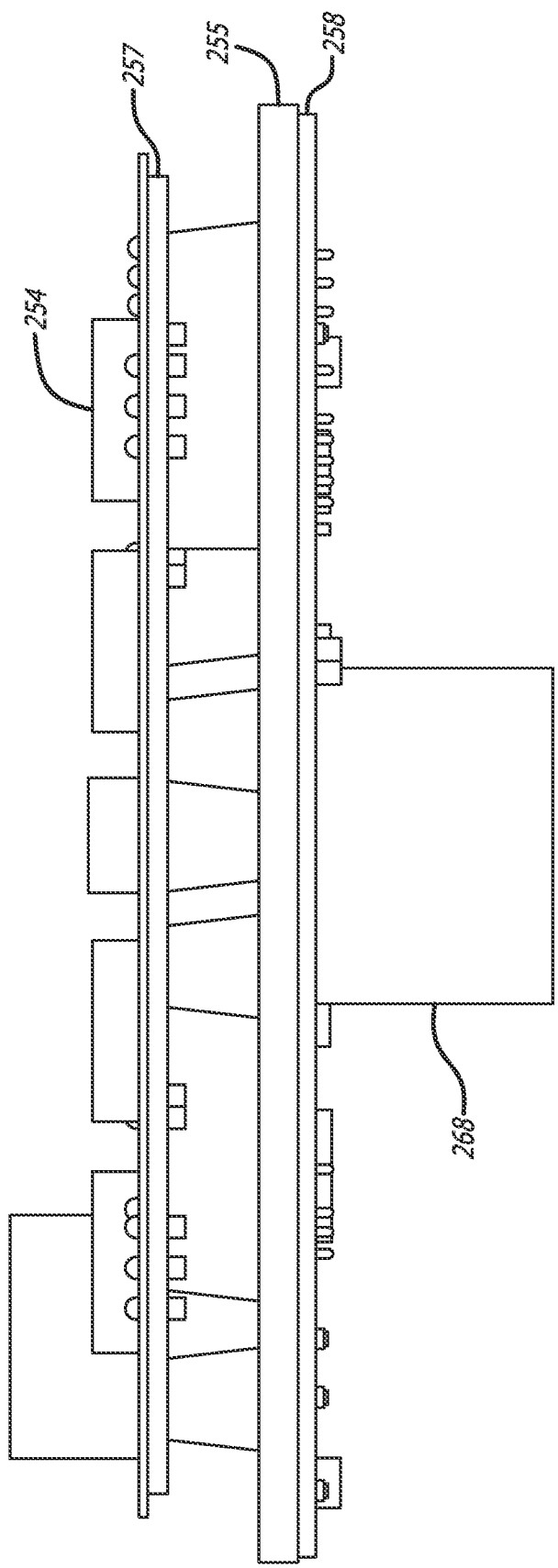
FIG. 53 is a diagrammatic perspective view of components of a hookah device of this disclosure.
Figure 54:
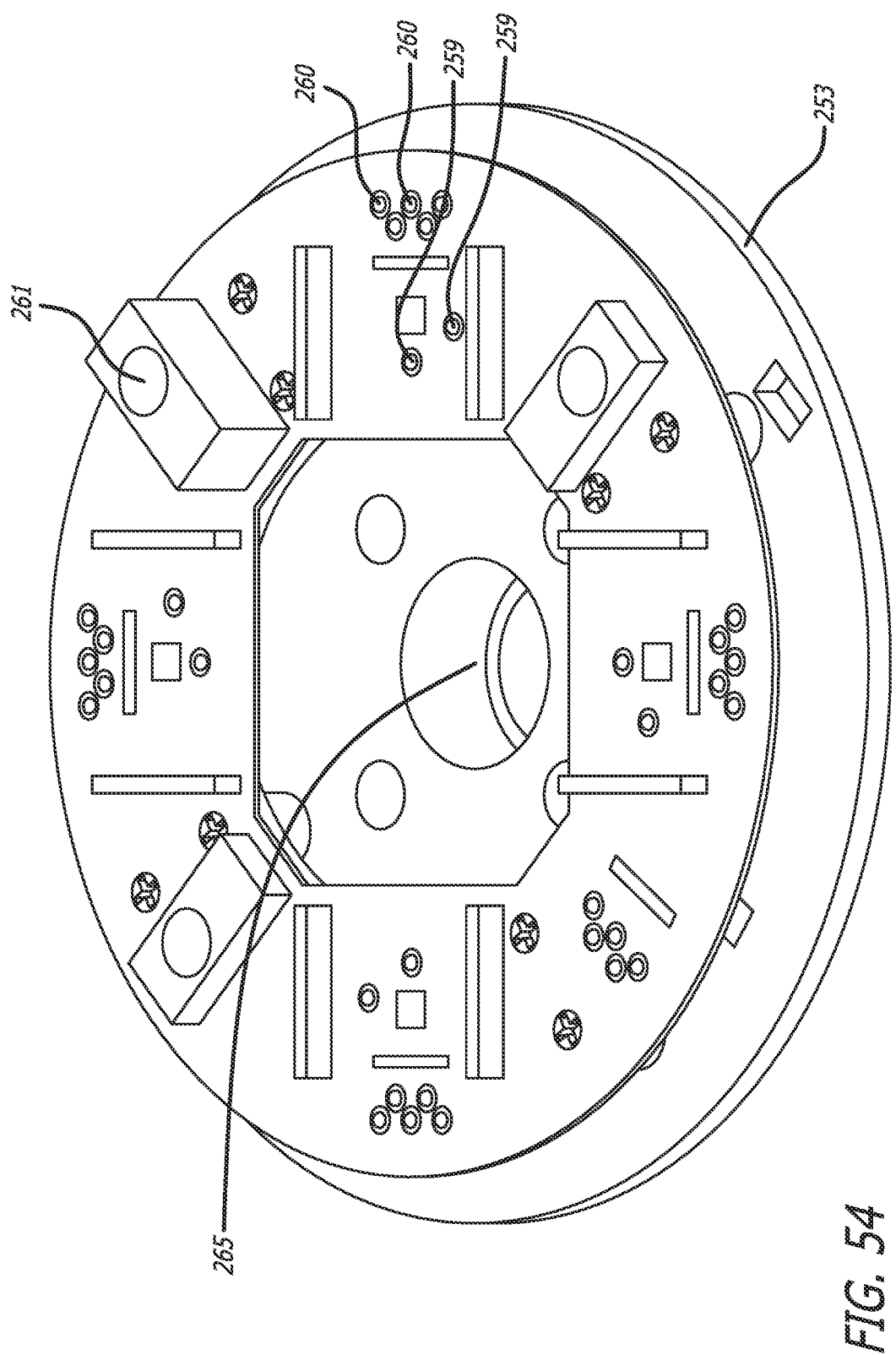
FIG. 54 is a diagrammatic perspective view of a component of a hookah device of this disclosure.
Figure 55:
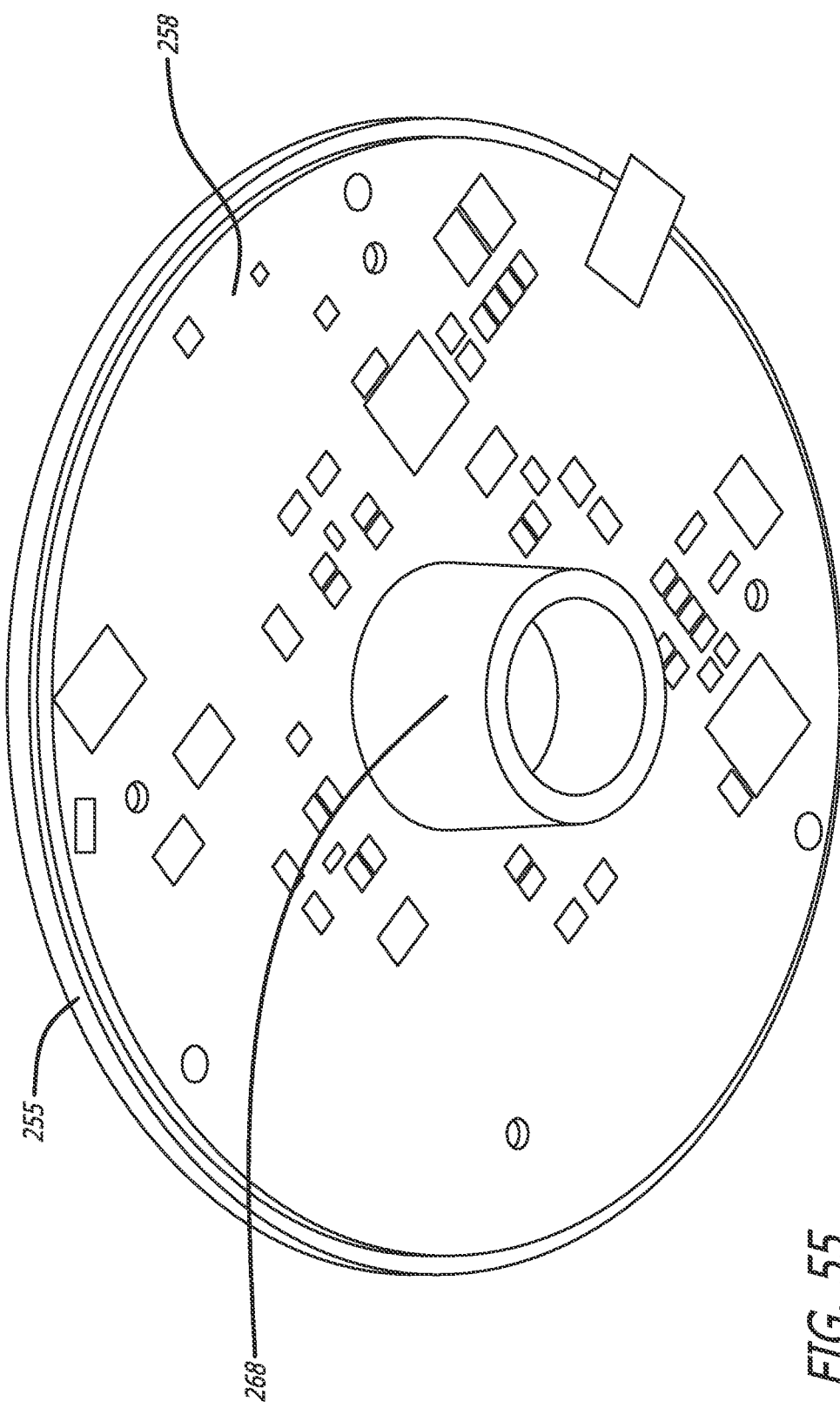
FIG. 55 is a diagrammatic perspective view of a component of a hookah device of this disclosure.
Figure 56:
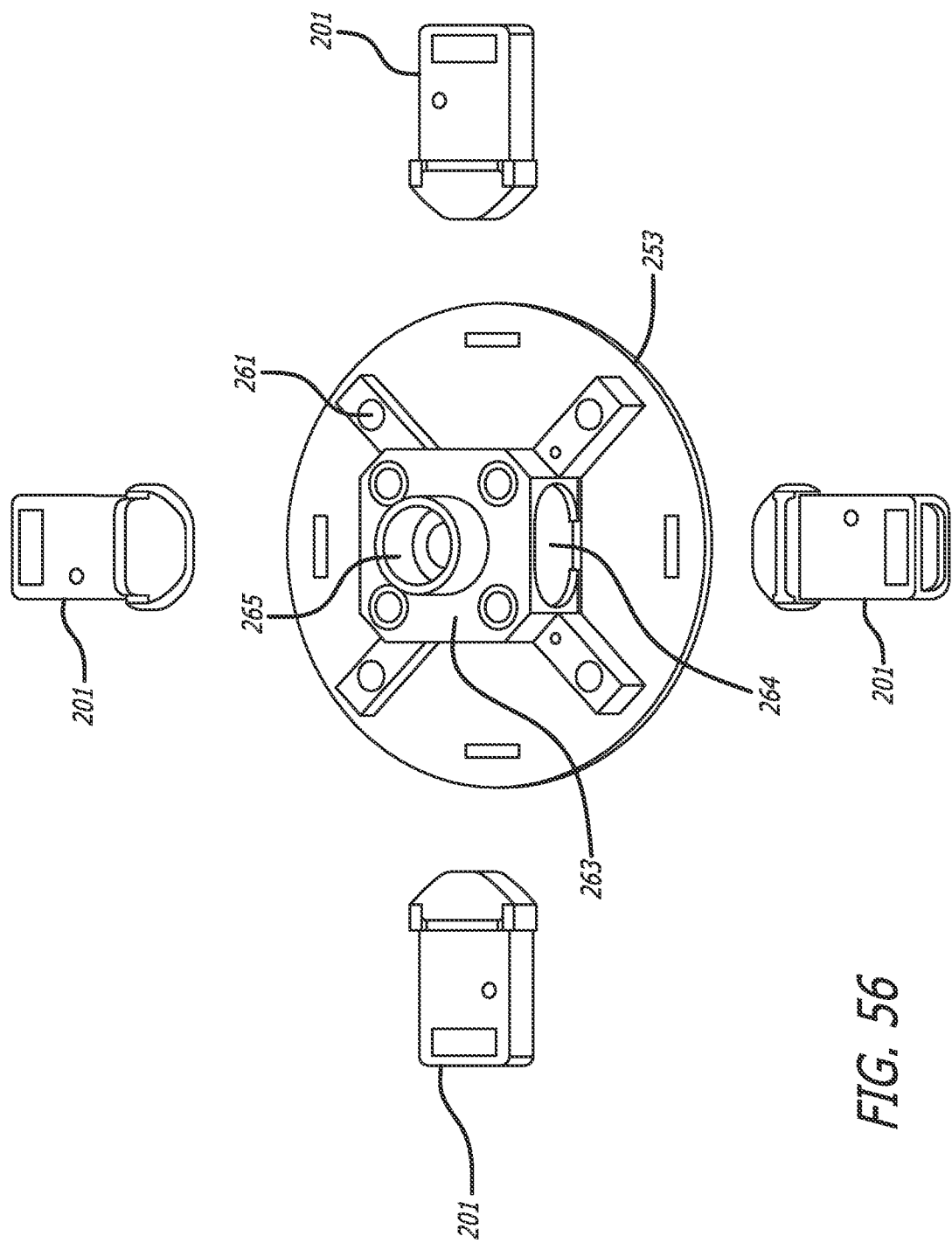
FIG. 56 is a diagrammatic perspective view of a component of a hookah device and four mist generator devices of this disclosure.
Figure 57:
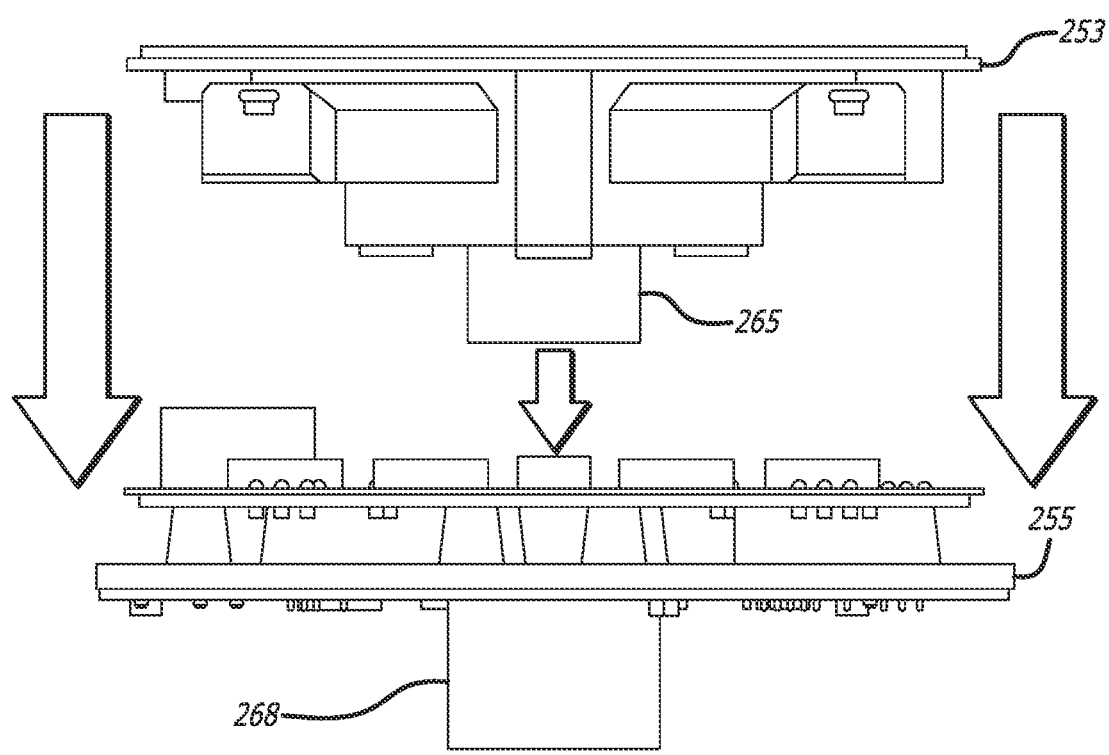
FIG. 57 is a diagrammatic perspective view of components of a hookah device of this disclosure.

Referring now to FIGS. 49 and 50 of the accompanying drawings, a hookah device 202 of some arrangements is configured to releasably attach to an existing hookah 246. The hookah device 202 attaches to the stem 247 in place of a conventional hookah head which would otherwise house the tobacco and the charcoal (or electronic heating element).

The hookah 246 comprises a water chamber and an elongate stem 247 having a first end which is attached to the water chamber. The stem 247 comprises a mist flow path which extends from a second end of the stem 247, through the stem 247, to the first end and into the water chamber.

In this arrangement, the hookah device 202 is releasably attached to the second end of the stem 247 of the hookah 246. However, in other arrangements the hookah device 202 is not designed to be removable and is instead fixed to or formed integrally with the stem 247 of the hookah 246.

Referring to FIGS. 51-59 of the accompanying drawings, the hookah device 202 comprises a housing 248 which incorporates a base 249 and a cover 250 which are attached or releasably attached to one another. In this arrangement, the housing 248 is cylindrical and generally disk-shaped.

In this arrangement, the cover 250 is provided with a plurality of air inlets 251 to allow air to be drawn into the hookah device 202. The base 249 is provided with a hookah outlet port 252 to allow air and mist to flow out from the hookah device 202 and into the hookah 246. The diameter of the hookah outlet port 252 is sufficient to allow a user to draw air quickly through the hookah device 202 and through the hookah 246 to generate bubbles of mist which travel through the water in the hookah 246.

In this arrangement, the hookah outlet port 252 is a circular aperture which receives the end of the stem 247 of the hookah 246. The hookah device 202 is supported on the stem 247 of the hookah 246 with a generally gas-tight seal being formed between the hookah device 202 and the stem 247.

In this arrangement, the hookah device 202 is a self-contained device with the electronic components and mist generator devices containing e-liquid being housed within the housing 248.

In this arrangement, the hookah device 202 comprises an upper support plate 253, a middle support plate 254 and a lower support plate 255 which are stacked on top of one another. The support plates 253-255 support a plurality of mist generator devices 201 within the hookah device 202. Each mist generator device is a mist generator device 201 as described in this disclosure. In this arrangement, the mist generator devices 201 a releasably attached to the hookah device 202 so that the mist generator devices 201 can be replaced when empty (i.e. when the e-liquid is partially or completely depleted).

In this arrangement, the hookah device 202 comprises four mist generator devices 201 which are controlled by the microcontroller 303 of the hookah device 202 (via each respective PMIC 300 and bridge IC 301). In other arrangements, the hookah device 202 comprises a plurality of mist generator devices 201, such as at least two mist generator devices 201 or up to eight mist generator devices 201.

The hookah device 202 is provided with first contact terminals 259 which establish and electrical connection between the controller of the hookah device 202 and the electrical contacts 232 and 233 of each mist generator device 201. The hookah device 202 is provided with second contact terminals 260 which establish and electrical connection between the controller of the hookah device 202 and the electrical contacts 241 on the OTP PCB of each mist generator device 201.

In this arrangement, the hookah device 202 comprises an upper printed circuit board (PCB) 256 which is positioned on top of the upper support plate 253 and a middle PCB 257 which is positioned between the middle support plate 254 and the lower support plate 255. A lower PCB 258 is positioned beneath the lower support plate 255. The PCBs 256-258 carry the electronic components which make up a driver device of the hookah device 202. The PCBs 256-258 are coupled electrically to one another to allow the electronic components on each PCB 256-258 to communicate with one another.

While there are three PCBs 256-258 in this arrangement, other arrangements comprise only one PCB or a plurality of PCBs which perform the same functions of the driver device of the hookah device 202.

In this arrangement, the hookah device 202 comprises a plurality of magnets 261 which enable the support plates 253-255 to be releasably attached to one another. Once the hookah device 202 is assembled with the support plates 253-255 and the PCBs 256-258 stacked on top of one another with the mist generator device 201 retained between the support plates 253-255, the cover 250 is placed onto the base 249 and a plurality of screws 262 are used to releasably attach the cover 250 to the base 249.

The upper support plate 253 comprises a manifold 263 which is positioned centrally on one side of the upper support plate 253. In this arrangement, the manifold 263 is provided with four apertures 264 (only one of which is visible in FIG. 56) which each receive the outlet port 208 of a respective mist generator device 201. In this arrangement, the hookah device 202 comprises four mist generator devices 201 which are releasably coupled to the manifold at 90° relative to one another. In other arrangements, the manifold 263 comprises a different number of apertures 264 to correspond with the number of mist generator devices 201 being used with the hookah device 202.

The manifold 263 comprises a manifold pipe 265 which is in fluid communication with the apertures 264 such that mist generated by the mist generator devices 201 can combine and flow down from the manifold 263 and out of the manifold pipe 265. When the hookah device 202 is assembled, the manifold pipe 265 extends through an aperture 266 in the middle support plate 254 and an aperture 267 in the middle PCB 257. The manifold pipe 265 then connects to an outlet pipe 268 which extends through the lower support plate 255 to provide a fluid flow path through the lower support plate to the hookah outlet port 252 of the hookah device 202.

In use, each of the mist generator devices 201 is held by the manifold in a horizontal orientation. That is to say, the longitudinal length of each mist generator device 201 is perpendicular or generally perpendicular to the direction of flow of mist as the mist flows downwardly from the base of the hookah device 202.

The outlet pipe 268 extends downwardly from the underside of the lower support plate 255 and through and aperture 269 in the lower PCB 258. The outlet pipe 268 then extends through an aperture 270 in the base 249 of the hookah device 202. In this arrangement, the outlet pipe 268 and the hookah outlet port 252 are a hookah attachment arrangement 271 which attaches or is configured to attach the hookah device 202 to a hookah 246. In this arrangement, the hookah device 202 is attached to the hookah 246 by inserting part of the stem 247 of the hookah into the hookah outlet port 252.

Figure 58:
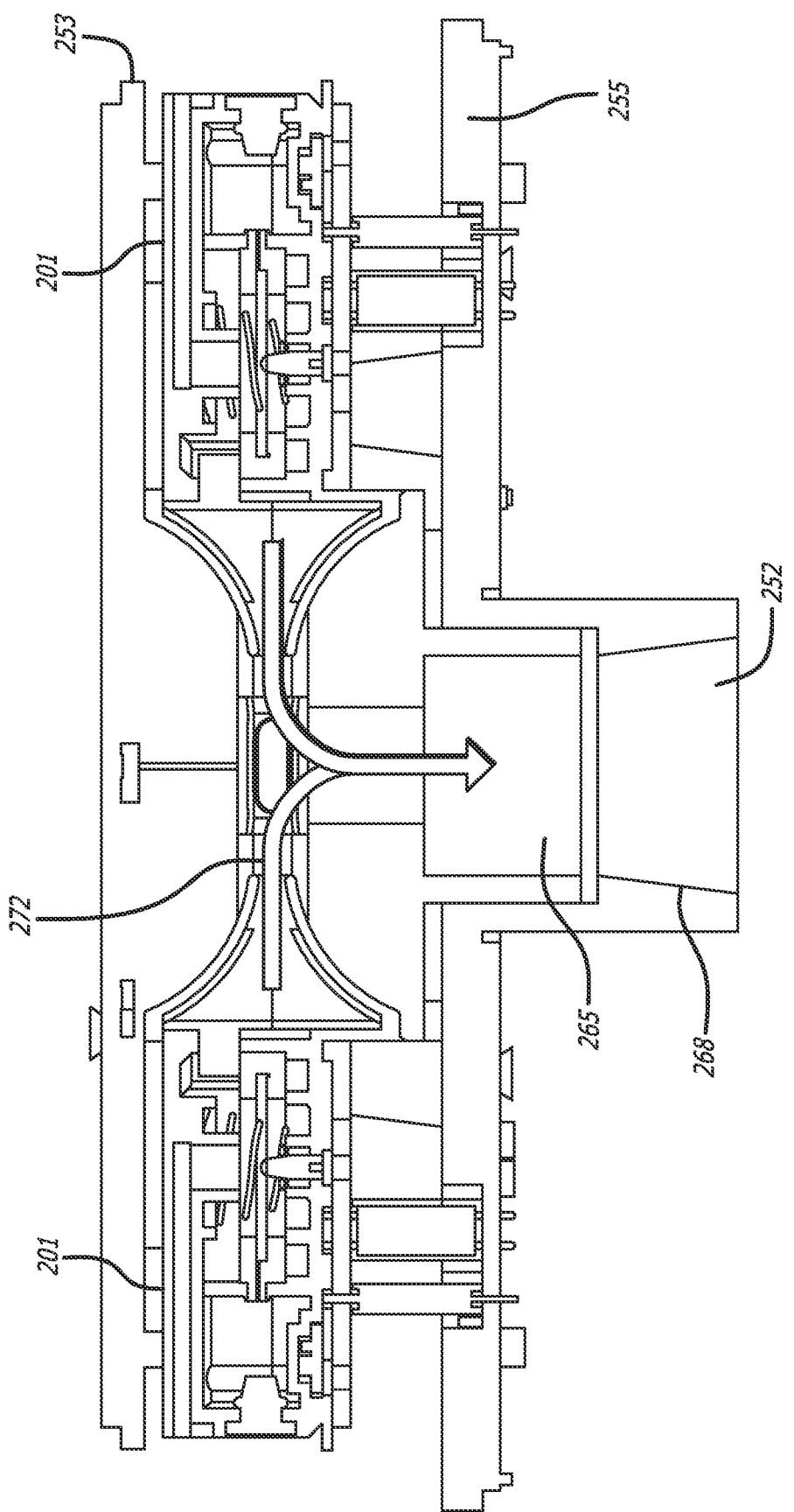
FIG. 58 is a diagrammatic cross-sectional view of components of a hookah device of this disclosure.
Figure 59:
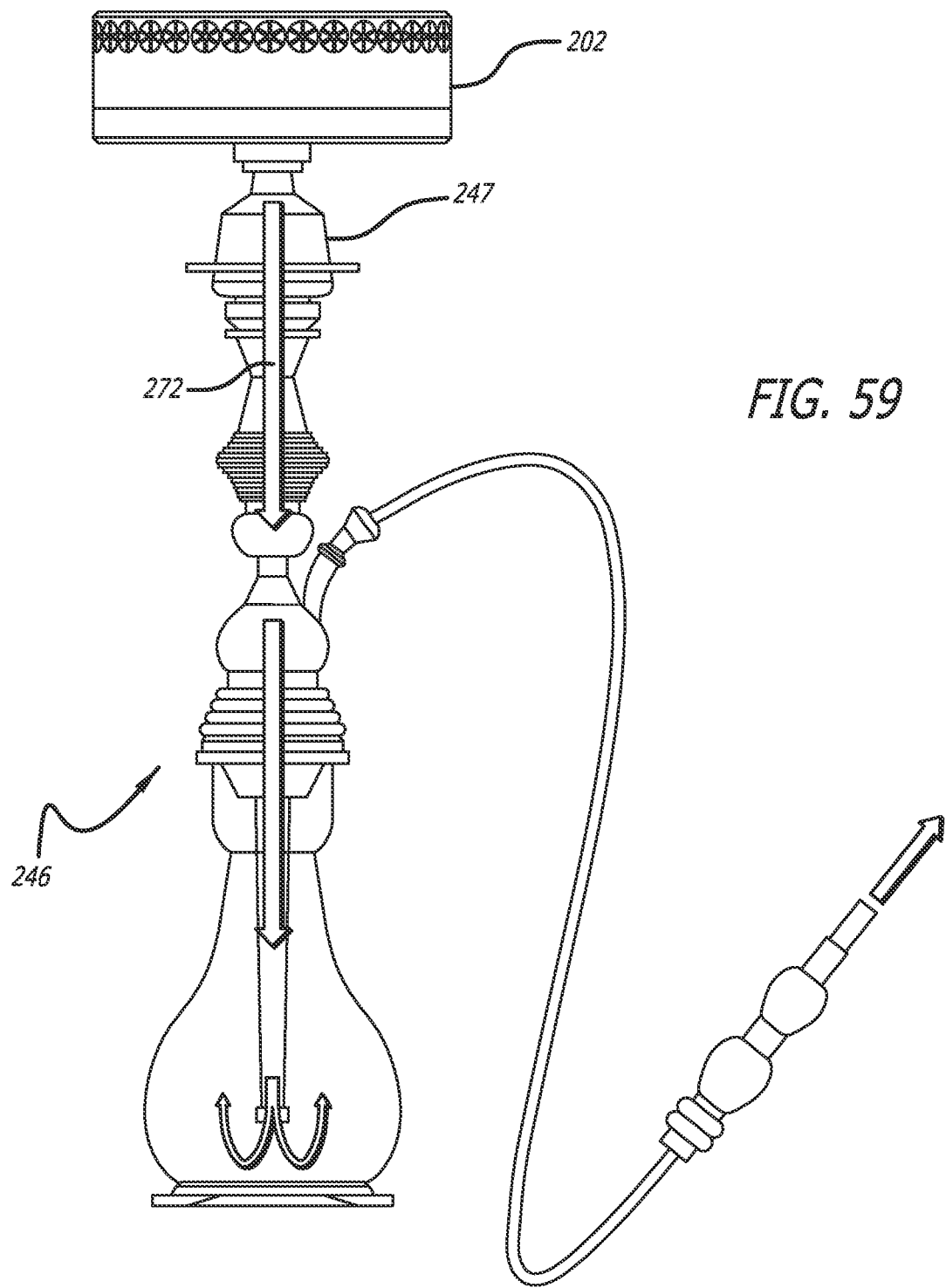
FIG. 59 is a diagrammatic perspective view of a hookah device of this disclosure attached to a hookah body and water bowl of a hookah apparatus.

The hookah outlet port 252 provides a fluid flow path 272, as shown in FIGS. 58 and 59, from the mist outlet ports 208 of the mist generator devices 201 and out of the hookah device 202 such that mist generated by the mist generator devices 201 flows out from the hookah device 202 and into the hookah 246. The mixture of air and mist creates bubbles in the water of the hookah 246. The bubbles escape the water surface with the mist rising above the surface of water in the water bowl of the hookah and travel through the pipe to the user during inhalation.

In this arrangement, the upper PCB 256 carries a pressure sensor which senses the pressure of air in the vicinity of the mist outlet ports 208 of the mist generator devices 201. The pressure sensor thereby detects a negative pressure in the vicinity of the mist outlet ports 208 when a user draws on the hookah and sucks air through the mist generator devices 201 along the fluid flow path 272. The pressure sensor provides a signal to the controller of the hookah device, as described below, for the controller to activate at least one of the mist generator devices 201 to generate mist as the user draws on the hookah.

In this arrangement, the lower PCB 258 carries power control components 273 which control and distribute power to the other electronic components of the hookah device 202. In some arrangements, the power control components 273 receive power from an external power source, such as a mains power adapter, which is releasably attached to the hookah device 202. In this arrangement, the hookah head 202 is configured to be powered by an external power adaptor at a DC voltage in the range 20V to 40V.

In other arrangements, the hookah device 202 comprises a battery which is integrated within the hookah device 202 and connected to the power control components 273. In some arrangements, the battery is a rechargeable Li-Po battery. In some arrangements, the battery is configured to output a 20V to 40V DC voltage. In some arrangements, the battery has a high discharge rate. The high discharge rate is necessary for the voltage amplification that is required by the ultrasonic transducers of the mist generator devices 201. Due to the requirement of having a high discharge rate, the Li-Po battery of some arrangements is designed specifically for continuous current draw. In some arrangements, a charging port is provided on the hookah device 202 to enable the battery to be charged by an external power source.

The middle PCB 257 incorporates a processor 274 and a memory 275 of a controller or computing device of the hookah device 202. In this example, each PMIC 300 and each bridge IC 301 are mounted to the PCB 257 along with the other electrical components of the hookah device 22. In this arrangement, the processor 274 and the memory 275 are components of the driver device within the hookah device 202. In this arrangement, the functionality of the driver device is implemented in executable instructions which are stored in the memory 275 which, when executed by the processor 274, cause the processor 274 to control the driver device to perform at least one function. The driver device is connected electrically to each of the mist generator devices 201. In this arrangement, the driver device of the hookah device 202 is coupled for communication with each mist generator device 201 by a communications bus or data bus, such as an I²C data bus, as described above. In this arrangement, each mist generator device 201 is identified by a unique identifier which is used when controlling the mist generator device 201 via the data bus (the microcontroller 303 controls each PMIC 300 via the data bus which in turn controls the respective mist generator device 201). In some arrangements, the unique identifier is stored in the OTP IC 242 of the mist generator device 201.

In some arrangements, the driver device (the microcontroller 303) controls each respective mist generator device independently. In some arrangements, the control functionality is implemented in executable instructions stored in the memory 275. The independent control configuration enables the driver device to activate or deactivate each mist generator device 201 independently of the other mist generator devices 201. The driver device can therefore control one or more of the mist generator devices 201 to generate mist simultaneously or alternately according to predetermined requirements.

In some arrangements, the driver device controls the mist generator devices 201 to activate and/or deactivate successively in sequence. In some arrangements the sequence of activation of the mist generator devices 201 optimizes the operation of the hookah device 202 by ensuring that mist is generated sufficiently quickly to allow the mist to pass in bubbles through the water in the water chamber of the hookah. The hookah device 202 of some arrangements thereby enables bubbles of mist to be drawn at high velocity through the water in the water chamber as a user draws on the hookah mouthpiece. Consequently, water soluble compounds (e.g. vegetable glycerin, flavorings, etc.) are able to travel through the water in in the bubbles of mist for inhalation by a user.

In some arrangements, the driver device controls the mist generator devices 201 to activate for a predetermined length of time one after another in sequence. In some arrangements, the driver device controls the mist generator devices 201 to activate in rotation such that the mist generator devices 201 are activated one after the other and/or one at a time in a clockwise or anticlockwise direction.

In some arrangements, the driver device controls the mist generator devices 201 to activate in pairs. In some arrangements, the driver device controls two mist generator devices 201 to activate simultaneously; either two mist generator devices 201 that are adjacent to one another or two mist generator devices that are opposite one another.

In some arrangements, the driver device is configured to ensure that a mist generator device 201 is not activated if it is not properly wicked with e-liquid in its capillary 222 or if the liquid chamber 218 empty or nearly empty of e-liquid. This provides protection for the hookah device 202 by ensuring that the hookah device 202 maintains correct operation.

The electronics of the driver device of the hookah device 202 (distributed across the PCBs 256-258) are divided as discussed below. The following description refers to the control of one mist generator device 201 but it is to be appreciated that the driver device of the hookah device 202 controls each mist generator device 201 independently in the same way.

In order to obtain the most efficient aerosolization, with particle size below 1 um, the driver device provides the contacts pads receiving the ultrasonic transducer 215 (piezoelectrical ceramic disc (PZT)) with high adaptive frequency (approximately 3 MHz).

This section not only has to provide high frequency but also protect the ultrasonic transducer 215 against failures while providing constant optimized cavitation.

PZT mechanical deformation is linked to the AC Voltage amplitude that is applied to it, and in order to guarantee optimal functioning and delivery of the system at every sonication, the maximum deformation must be supplied to the PZT all the time.

However, in order to prevent the failure of the PZT, the active power transferred to it must be precisely controlled.

The processor 274 and the memory 275 are configured to control modulation of the active power given to the PZT at every instant without compromising the mechanical amplitude of vibration of the PZT.

By Pulse Width Modulation (PWM) of the AC voltage applied to the PZT, the mechanical amplitude of the vibration remains the same.

Indeed, the RMS voltage applied would be the same with effective Duty Cycle modulation as with Voltage modulation, but the active power transferred to the PZT would degrade. Indeed, given the formula below:

$$\text{Active Power displayed to the } PZT \text{ being } \mathrm{Pa} = \frac{2\sqrt{2}}{\pi} Irms * Vrms * \cos\varphi,$$

Where

φ is the shift in phase between current and voltage $I_{rms}$ is the root mean square Current $V_{rms}$ is the root mean square Voltage.

When considering the first harmonic, Irms is a function of the real voltage amplitude applied to the transducer, as the pulse width modulation alters the duration of voltage supplied to the transducer, controlling Irms.

The specific design of the PMIC uses a state-of-the-art design, enabling ultra-precise control of the frequency range and steps to apply to the PZT including a complete set of feedback loops and monitoring path for the control section to use.

In this arrangement, the driver device comprises a DC/DC boost converter and transformer that carry the necessary power to the PZT contact pads.

In this arrangement, the driver device comprises an AC driver for converting a voltage from the battery into an AC drive signal at a predetermined frequency to drive the ultrasonic transducer.

The driver device comprises an active power monitoring arrangement for monitoring the active power used by the ultrasonic transducer (as described above) when the ultrasonic transducer is driven by the AC drive signal. The active power monitoring arrangement provides a monitoring signal which is indicative of an active power used by the ultrasonic transducer.

The processor 274 within the driver device controls the AC driver and receives the monitoring signal drive from the active power monitoring arrangement, The memory 275 of driver device stores instructions which, when executed by the processor, cause the processor to:

A. control the AC driver to output an AC drive signal to the ultrasonic transducer at a sweep frequency.

B. calculate the active power being used by the ultrasonic transducer based on the monitoring signal;

C. control the AC driver to modulate the AC drive signal to maximize the active power being used by the ultrasonic transducer;

D. store a record in the memory of the maximum active power used by the ultrasonic transducer and the sweep frequency of the AC drive signal;

E. repeat steps A-D for a predetermined number of iterations with the sweep frequency incrementing or decrementing with each iteration such that, after the predetermined number of iterations has occurred, the sweep frequency has been incremented or decremented from a start sweep frequency to an end sweep frequency;

F. identify from the records stored in the memory the optimum frequency for the AC drive signal which is the sweep frequency of the AC drive signal at which a maximum active power is used by the ultrasonic transducer; and G. control the AC driver to output an AC drive signal to the ultrasonic transducer at the optimum frequency to drive the ultrasonic transducer to atomize a liquid.

In some arrangements, the active power monitoring arrangement comprises a current sensing arrangement for sensing a drive current of the AC drive signal driving the ultrasonic transducer, wherein the active power monitoring arrangement provides a monitoring signal which is indicative of the sensed drive current.

In some arrangements, the current sensing arrangement comprises an Analog-to-Digital Converter which converts the sensed drive current into a digital signal for processing by the processor.

In some arrangements, the start frequency is 2900 kHz and the end frequency is 3100 kHz. In other arrangements, the start frequency is 3100 kHz and the end frequency is 2900 kHz.

In some arrangements, the memory stores instructions which, when executed by the processor, cause the processor to: repeat steps A-D above with the sweep frequency being incremented from a start sweep frequency of 2900 kHz to an end sweep frequency of 2960 kHz.

In some arrangements, the memory stores instructions which, when executed by the processor, cause the processor to: repeat steps A-D above with the sweep frequency being incremented from a start sweep frequency of 2900 kHz to an end sweep frequency of 3100 kHz.

In some arrangements, the memory stores instructions which, when executed by the processor, cause the processor to: in step G, control the AC driver to output an AC drive signal to the ultrasonic transducer at frequency which is shifted by a predetermined shift amount from the optimum frequency.

In some arrangements, the predetermined shift amount is between 1-10% of the optimum frequency.

The pressure sensor used in the device serves two purposes. The first purpose is to prevent unwanted and accidental start of the sonic engine (driving the ultrasonic transducer). This functionality is implemented in the processing arrangement of the device, but optimized for low power, to constantly measure environmental parameters such as temperature and ambient pressure with internal compensation and reference setting in order to accurately detect and categories what is called a true inhalation.

The second purpose of the pressure sensor is to be able to monitor not only the exact duration of the inhalations by the user for precise inhalation volume measurement, but also to be able to determine the strength of the user inhalation. All in all, we are able to completely draw the pressure profile of every inhalation and anticipate the end of an inhalation for aerosolization optimization.

In some arrangements, the hookah device 202 comprises a Bluetooth™ Low Energy (BLE) microcontroller. Indeed, this enables the setting to provide extremely accurate inhalation times, optimized aerosolization, monitor numerous parameters to guarantee safe misting and prevent the use of non-genuine e-liquids or aerosol chambers and protect both the device against over-heating risks and the user against over-misting in one shot.

The use of the BLE microcontroller allows over-the-air update to continuously provide improved software to users based on anonymized data collection and trained AI for PZT modelling. The BLE microcontroller also enables a remote computing device to communicate with the hookah device 202 so that the remote computing device can control the operation of the hookah device 202. In one example, a plurality of hookah devices are controlled by one or more remote computing devices, for instance in a hookah or shisha bar to enable the manager of the bar to control the operation and/or monitor the state of each hookah device.

In one example, data indicative of the status of each mist generator device in each hookah device is transmitted by the hookah device to a remote computing device so that the remote computing device can monitor the status of each individual mist generator device. This enables a manager or user to track when each mist generator device is low on liquid or not operating correctly, so that the mist generator device can be replaced.

The hookah device 202 is a precise, reliable and a safe aerosolization solution for daily customer usage and, as such, must provide a controlled and trusted aerosolization.

This is performed through an internal method that can be broken apart into several sections as follows:

Sonication

In order to provide the most optimal aerosolization the ultrasonic transducer (PZT) or each mist generator device 201 needs to vibrate in the most efficient way.

Frequency

The electromechanical properties of piezoelectrical ceramics state that the component has the most efficiency at the resonant frequency. But also, vibrating a PZT at resonance for a long duration will inevitably end with the failure and breaking of the component which renders the aerosol chamber unusable.

Another important point to consider when using piezoelectrical materials is the inherent variability during manufacturing and its variability over temperature and lifetime.

Resonating a PZT at 3 MHz in order to create droplets of a size<1 um requires an adaptive method in order to locate and target the 'sweet spot' of the particular PZT inside every aerosol chamber used with the device for every single inhalation.

Sweep

Because the device has to locate the 'sweet spot' for every single inhalation and because of over-usage, the PZT temperature varies as the device uses an in-house double sweep method.

The first sweep is used when the device has not been used with a particular aerosol chamber for a time that is considered enough for all the thermal dissipation to occur and for the PZT to cool down to 'default temperature'. This procedure is also called a cold start. During this procedure the PZT needs a boost in order to produce the required aerosol. This is achieved by only going over a small subset of Frequencies between 2900 kHz to 2960 kHz which, considering extensive studies and experiments, covers the resonant point.

For each frequency in this range, the sonic engine in activated and the current going through the PZT is actively monitored and stored by the microcontroller via an Analog-to-Digital Converter (ADC), and converted back to current in order to be able to precisely deduct the Power used by the PZT.

This yields the cold profile of this PZT regarding frequency and the Frequency used throughout the inhalation is the one that uses the most current, meaning the lowest impedance Frequency.

The second sweep is performed during any subsequent inhalation and cover the entire range of frequencies between 2900 kHz to 3100 kHz due to the modification of the PZT profile with regards to temperature and deformation. This hot profile is used to determine the shift to apply.

Shift

Because the aerosolization must be optimal, the shift is not used during any cold inhalation and the PZT will hence vibrate at resonant frequency. This can only happen for a short and unrepeated duration of time otherwise the PZT would inevitably break.

The shift however is used during most of inhalations as a way to still target a low impedance frequency, thus resulting in quasi-optimal operation of the PZT while protecting it against failures.

Because the hot and cold profiles are stored during inhalation the microcontroller can then select the proper shifted frequency according to the measured values of current through the PZT during sweep and ensure a safe mechanical operation.

The selection of the direction to shift is crucial as the piezoelectrical component behaves in a different way if outside the duplet resonant/anti-resonant frequency or inside this range. The selected shift should always be in this range defined by Resonant to anti-Resonant frequencies as the PZT is inductive and not capacitive.

Finally, the percentage to shift is maintained below 10% in order to still remain close to the lowest impedance but far enough of the resonance.

Adjustment

Because of the intrinsic nature of PZTs, every inhalation is different. Numerous parameters other than the piezoelectrical element influence the outcome of the inhalation, like the amount of e-liquid remaining inside the aerosol chamber, the wicking state of the gauze or the battery level of the device.

As of this, the device permanently monitors the current used by the PZT inside the aerosol chamber and the microcontroller constantly adjusts the parameters such as the frequency and the Duty Cycle in order to provide the aerosol chamber with the most stable power possible within a pre-defined range that follows the studies and experimental results for most optimal safe aerosolization.

Battery Monitoring

In some arrangements, a battery is integrated within the hookah device 202. In these arrangements, the hookah device 202 is powered by a DC Li-Po battery which provides a required voltage to the hookah device 202. Due to the requirement of having a high discharge rate, the Li-Po battery of some arrangement is designed specifically for continuous current draw.

Because the battery voltage drops and varies a lot when activating the sonication section, the microcontroller constantly monitors the power used by the PZT inside the aerosol chamber to ensure a proper but also safe aerosolization.

And because the key to aerosolization is control, the device ensures first that the Control and Information section of the device always function and does not stop in the detriment of the sonication section.

This is why the adjustment method also takes into great account the real time battery level and, if need be, modifies the parameters like the Duty Cycle to maintain the battery at a safe level, and in the case of a low battery before starting the sonic engine, the Control and Information section will prevent the activation.

Power Control

As being said, the key to aerosolization is control and the method used in the device is a real time multi-dimensional function that takes into account the profile of the PZT, the current inside the PZT and the battery level of the device at all time.

All this is only achievable thanks to the use of a microcontroller that can monitor and control every element of the device to produce an optimal inhalation.

Interval

Because the device relies on a piezoelectrical component, the device prevents the activation of the sonication section if an inhalation stops. The safety delay in between two inhalations is adaptive depending on the duration of the previous one. This allows the gauze to wick properly before the next activation.

With this functioning, the device can safely operate and the aerosolization is rendered more optimal with no risk of breaking the PZT element nor exposing the user to toxic components.

Connectivity (BLE)

The device Control and Information section is composed of a wireless communication system in the form of a Bluetooth Low Energy capable microcontroller. The wireless communication system is in communication with the processor of the device and is configured to transmit and receive data between the driver device and a computing device, such as a smartphone.

The connectivity via Bluetooth Low Energy to a companion mobile application ensures that only small power for this communication is required thus allowing the device to remain functioning for a longer period of time if not used at all, compared to traditional wireless connectivity solutions like Wi-Fi, classic Bluetooth, GSM or even LTE-M and NB-IOT.

Most importantly, this connectivity is what enables the OTP as a feature and the complete control and safety of the inhalations. Every data from resonant frequency of an inhalation to the one used, or the negative pressure created by the user and the duration are stored and transferred over BLE for further analysis and improvements of the embedded software.

Finally, this connectivity enables the update of the embedded firmware inside the device and over the air (OTA), which guarantees that the latest versions can always be deployed rapidly. This gives great scalability to the device and insurance that the device is intended to be maintained.

In one example, the hookah device incorporates a mist inhaler device 200 which comprises an active power monitor which incorporates a current sensor, such as the current sensor 335 described above, for sensing an rms drive current of the AC drive signal driving the ultrasonic transducer 215. The active power monitor provides a monitoring signal which is indicative of the sensed drive current, as described above.

The additional functionality of this example enables the mist inhaler device 200 to monitor the operation of the ultrasonic transducer while the ultrasonic transducer is activated. The mist inhaler device 200 calculates an effectiveness value or quality index which is indicative of how effective the ultrasonic transducer is operating to atomise a liquid within the device. The device uses the effectiveness value to calculate the actual amount of mist that was generated over the duration of activation of the ultrasonic transducer.

Once the actual amount of mist has been calculated, the device is configured to calculate the actual amount of a drug which was present in the mist and hence the actual amount of a drug which was inhaled by a user based on the concentration of the drug in the liquid.

In practice, as described above, there are many different factors which affect the operation of an ultrasonic transducer and which have an impact on the amount of mist which is generated by the ultrasonic transducer and hence the actual amount of a drug which is delivered to a user.

The configuration of the mist inhaler device and a method of generating mist using the mist inhaler device of some examples will now be described in detail below.

In this example, the mist inhaler device incorporates the components of the mist inhaler device 200 described above, but the memory of the driver device 202 further stores instructions which, when executed by the processor, cause the processor to activate the mist generator device 200 for a first predetermined length of time. As described above, the mist generator device is activated by driving the ultrasonic transducer 215 in the mist generator device 200 with the AC drive signal so that the ultrasonic transducer 215 atomises liquid carried by the capillary element 222.

The executed instructions cause the processor to sense, using a current sensor, periodically during the first predetermined length of time the current of the AC drive signal flowing through the ultrasonic transducer 215 and storing periodically measured current values in the memory.

The executed instructions cause the processor to calculate an effectiveness value using the current values stored in the memory. The effectiveness value is indicative of the effectiveness of the operation of the ultrasonic transducer at atomising the liquid.

In one example, the executed instructions cause the processor to calculate the effectiveness value using this equation:

$$Q_I = \frac{\sum_{t=0}^{t=D} \frac{\sqrt{Q_{A(t)}^2 + Q_{F(t)}^2}}{\sqrt{2}}}{N}$$

where:
- $Q_I$ is the effectiveness value,
- $Q_F$ is a frequency sub-effectiveness value which is based on the monitored frequency value (the frequency at which the ultrasonic transducer 215 is being driven),
- $Q_A$ is an analogue to digital converter sub-effectiveness value which is based on the measured current value (the rms current flowing through the ultrasonic transducer 215),
- t=0 is the start of the first predetermined length of time,
- t=D is the end of the first predetermined length of time,
- N is the number of periodic measurements (samples) during the first predetermined length of time, and
- $\sqrt{2}$ is a normalization factor.

In one example, the memory stores instructions which, when executed by the processor, cause the processor to measure periodically during the first predetermined length of time the duty cycle of the AC drive signal driving the ultrasonic transducer and storing periodically measured duty cycle values in the memory. The mist inhaler device then modifies the analogue to digital converter sub-effectiveness value $Q_A$ based on the current values stored in the memory. Consequently, the mist inhaler device of this example takes into account variations in the duty cycle which may occur throughout the activation of the ultrasonic transducer 215 when the device calculates the effectiveness value. The mist inhaler device can therefore calculate the actual amount of mist which is generated accurately by taking into account variations in the duty cycle of the AC drive signal which may occur while the ultrasonic transducer is activated.

The effectiveness value is used by the mist inhaler device as a weighting to calculate the actual amount of mist generated by the mist inhaler device by proportionally reducing a value of a maximum amount of mist that would be generated if the device was operating optimally.

In one example, the memory stores instructions which, when executed by the processor, cause the processor to measure periodically during the first predetermined length of time the frequency of the AC drive signal driving the ultrasonic transducer 215 and storing periodically measured frequency values in the memory. The device then calculates the effectiveness value using the using the frequency values stored in the memory, in addition to the current values as described above.

In one example, the memory stores instructions which, when executed by the processor, cause the processor to calculate a maximum mist amount value that would be generated if the ultrasonic transducer 215 was operating optimally over the duration of the first predetermined length of time. In one example, the maximum mist amount value is calculate based on modelling which determines the maximum amount of mist which would be generated when the ultrasonic transducer was operating optimally.

Once the maximum mist amount value has been calculated, the mist inhaler device can calculate an actual mist amount value by reducing the maximum mist amount value proportionally based on the effectiveness value to determine the actual mist amount that was generated over the duration of the first predetermined length of time.

Once the actual mist amount has been calculated, the mist inhaler device can calculate a drug amount value which is indicative of the amount of a drug in the actual mist amount that was generated over the duration of the first predetermined length of time. The mist inhaler device then stores a record of the drug amount value in the memory.

In one example, the memory stores instructions which, when executed by the processor, cause the processor to selecting a second predetermined length of time in response to the effectiveness value. In this case, the second predetermined length of time is a length of time over which the ultrasonic transducer 215 is activated during a second inhalation or puff by a user. In one example, the second predetermined length of time is equal to the first predetermined length of time but with the time reduced or increased proportionally according to the effectiveness value. For instance, if the effectiveness value indicates that the ultrasonic transducer 215 is not operating effectively, the second predetermined length of time is made longer by the effectiveness value such that a desired amount of mist is generated during the second predetermined length of time.

When it comes to the next inhalation, the mist inhaler device activates the mist generator device for the second predetermined length of time so that the mist generator device generates a predetermined amount of mist during the second predetermined length of time. The mist inhaler device thus controls the amount of mist generated during the second predetermined length of time accurately, taking into account the various parameters which are reflected by the effectiveness value which affect the operation of the mist inhaler device.

In one example, the memory stores instructions which, when executed by the processor, cause the processor to activate the mist generator device for a plurality of predetermined lengths of time. For instance, the mist generator device is activated during a plurality of successive inhalations or puffs by a user.

The mist inhaler device stores a plurality of drug amount values in the memory, each drug amount value being indicative of the amount of a drug in the mist that was generated over the duration of a respective one of the predetermined lengths of time.

The mist inhaler of some examples of this disclosure is configured to transmit data indicative of the drug amount values from the mist generator device to a computing device (e.g. via Bluetooth™ Low Energy communication) for storage in a memory of the computing device (e.g. a smartphone). An executable application running on the computing device can thus log the amount of a drug which has been delivered to a user. The executable application can also control the operation of the mist inhaler device so that the application can modify the operation of each mist inhaler device in the hookah device to accommodate for a mist inhaler device not operating in an optimal manner.

Because the aerosolization of the e-liquid is achieved via the mechanical action of the piezoelectric disc and not due to the direct heating of the liquid, the individual components of the e-liquid (propylene glycol, vegetable glycerin, flavoring components, etc.) remain largely in-tact and are not broken into smaller, harmful components such as acrolein, acetaldehyde, formaldehyde, etc. at the high rate seen in traditional ENDS.

All of the above applications involving ultrasonic technology can benefit from the optimization achieved by the frequency controller which optimizes the frequency of sonication for optimal performance.

It is to be appreciated that the disclosures herein are not limited to use for nicotine delivery. The devices disclosed herein are for use with any drugs or other compounds (e.g. CBD), with the drug or compound being provided in a liquid within the liquid chamber of the device for aerosolization by the device.

The hookah device 202 of some arrangements is a healthier alternative to conventional hookah heads which burn tobacco using heat from charcoal or an electrical element. Nevertheless, the hookah device 202 of some arrangements still provides the same user experience as a conventional hookah due to the mist bubbles in the water of the hookah. Users are therefore likely to want to use the ultrasonic hookah device 202 of some arrangements instead of a conventional tobacco-burning hookah and thereby avoid the dangers of smoking tobacco in a hookah.

The foregoing outlines features of several arrangements, examples or embodiments so that those of ordinary skill in the art may better understand various aspects of the present disclosure. Those of ordinary skill in the art should appreciate that they may readily use the present disclosure as a basis for designing or modifying other processes and structures for carrying out the same purposes and/or achieving the same advantages of various examples or embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

Although the subject matter has been described in language specific to structural features or methodological acts, it is to be understood that the subject matter of the appended claims is not necessarily limited to the specific features or acts described above. Rather, the specific features and acts described above are disclosed as example forms of implementing at least some of the claims.

Various operations of examples or embodiments are provided herein. The order in which some or all of the operations are described should not be construed to imply that these operations are necessarily order dependent. Alternative ordering will be appreciated having the benefit of this description. Further, it will be understood that not all operations are necessarily present in each embodiment provided herein. Also, it will be understood that not all operations are necessary in some examples or embodiments.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application and the appended claims are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising". Also, unless specified otherwise, "first," "second," or the like are not intended to imply a temporal aspect, a spatial aspect, an ordering, etc. Rather, such terms are merely used as identifiers, names, etc. for features, elements, items, etc. For example, a first element and a second element generally correspond to element A and element B or two different or two identical elements or the same element.

Also, although the disclosure has been shown and described with respect to one or more implementations, equivalent alterations and modifications will occur to others of ordinary skill in the art based upon a reading and understanding of this specification and the annexed drawings. The disclosure comprises all such modifications and alterations and is limited only by the scope of the following claims. In particular regard to the various functions performed by the above described features (e.g., elements, resources, etc.), the terms used to describe such features are intended to correspond, unless otherwise indicated, to any features which performs the specified function of the described features (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

Examples or embodiments of the subject matter and the functional operations described herein can be implemented in digital electronic circuitry, or in computer software, firmware, or hardware, including the structures disclosed in this specification and their structural equivalents, or in combinations of one or more of them.

Some examples or embodiments are implemented using one or more modules of computer program instructions encoded on a computer-readable medium for execution by, or to control the operation of, a data processing apparatus. The computer-readable medium can be a manufactured product, such as hard drive in a computer system or an embedded system. The computer-readable medium can be acquired separately and later encoded with the one or more modules of computer program instructions, such as by delivery of the one or more modules of computer program instructions over a wired or wireless network. The computer-readable medium can be a machine-readable storage device, a machine-readable storage substrate, a memory device, or a combination of one or more of them.

The terms "computing device" and "data processing apparatus" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a runtime environment, or a combination of one or more of them. In addition, the apparatus can employ various different computing model infrastructures, such as web services, distributed computing and grid computing infrastructures.

The processes and logic flows described in this specification can be performed by one or more programmable processors executing one or more computer programs to perform functions by operating on input data and generating output.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices.

In the present specification "comprise" means "includes or consists of" and "comprising" means "including or consisting of".

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

REPRESENTATIVE FEATURES

Representative features are set out in the following clauses, which stand alone or may be combined, in any combination, with one or more features disclosed in the text and/or drawings of the specification.

1 A hookah device comprising:
  a plurality of ultrasonic mist generator devices, wherein each mist generator device incorporates:
    a mist generator housing which is elongate and comprises an air inlet port and a mist outlet port;
    a liquid chamber provided within the mist generator housing, the liquid chamber containing a liquid to be atomised;
    a sonication chamber provided within the mist generator housing;
    a capillary element extending between the liquid chamber and the sonication chamber such that a first portion of the capillary element is within the liquid chamber and a second portion of the capillary element is within the sonication chamber;
    an ultrasonic transducer having an atomisation surface, wherein part of the second portion of the capillary element is superimposed on part of the atomisation surface, and wherein when the ultrasonic transducer is driven by an AC drive signal the atomisation surface vibrates to atomise the liquid carried by the second portion of the capillary element to generate a mist comprising the atomised liquid and air within the sonication chamber; and an airflow arrangement which provides an air flow path between the air inlet port, the sonication chamber and the air outlet port, wherein the hookah device further comprises:
a plurality of H-bridge circuits, wherein each H-bridge circuit of the plurality of H-bridge circuits is connected to a respective one of the ultrasonic transducers and generates an AC drive signal to drive the ultrasonic transducer;
a microcontroller;
a data bus which is connected electrically to the microcontroller to communicate data to and from the microcontroller;
a plurality of microchips which are connected electrically to the data bus to receive data from and transmit data to the microcontroller, wherein each microchip of the plurality of microchips is connected to a respective one of the H-bridge circuits to control the H-bridge circuit to generate the AC drive signal, wherein each microchip is a single unit which comprises a plurality of interconnected embedded components and subsystems comprising:
an oscillator which generates:
  a main clock signal,
  a first phase clock signal which is high for a first time during the positive half-period of the main clock signal and low during the negative half-period of the main clock signal, and
  a second phase clock signal which is high for a second time during the negative half-period of the main clock signal and low during the positive half-period of the main clock signal, wherein the phases of the first phase clock signal and the second phase clock signal are centre aligned; a pulse width modulation (PWM) signal generator subsystem comprising:
  a delay locked loop which generates a double frequency clock signal using the first phase clock signal and the second phase clock signal, the double frequency clock signal being double the frequency of the main clock signal, wherein the delay locked loop controls the rising edge of the first phase clock signal and the second phase clock signal to be synchronous with the rising edge of the double frequency clock signal, and wherein the delay locked loop adjusts the frequency and the duty cycle of the first phase clock signal and the second phase clock signal in response to a driver control signal to produce a first phase output signal and a second phase output signal, wherein the first phase output signal and the second phase output signal are configured to drive the H-bridge circuit connected to the microchip to generate an AC drive signal to drive the ultrasonic transducer;
  a first phase output signal terminal which outputs the first phase output signal to the H-bridge circuit connected to the microchip;
  a second phase output signal terminal which outputs the second phase output signal to the H-bridge circuit connected to the microchip;
  a feedback input terminal which receives a feedback signal from the H-bridge circuit, the feedback signal being indicative of a parameter of the operation of the H-bridge circuit connected to the microchip or AC drive signal when the H-bridge circuit is driving the ultrasonic transducer with the AC drive signal to atomise the liquid;
an analogue to digital converter (ADC) subsystem comprising:
  a plurality of ADC input terminals which receive a plurality of respective analogue signals, wherein one ADC input terminal of the plurality of ADC input terminals is connected to the feedback input terminal such that the ADC subsystem receives the feedback signal from the H-bridge circuit connected to the microchip, and wherein the ADC subsystem samples analogue signals received at the plurality of ADC input terminals at a sampling frequency which is proportional to the frequency of the main clock signal and the ADC subsystem generates ADC digital signals using the sampled analogue signals;
a digital processor subsystem which receives the ADC digital signals from the ADC subsystem and processes the ADC digital signals to generate the driver control signal, wherein the digital processor subsystem communicates the driver control signal to the RWM signal generator subsystem to control the RWM signal generator subsystem; and
a digital to analogue converter (DAC) subsystem comprising:
  a digital to analogue converter (DAC) which converts a digital control signal generated by the digital processor subsystem into an analogue voltage control signal to control a voltage regulator circuit which generates a voltage for modulation by the H-bridge circuit connected to the microchip; and
  a DAC output terminal which outputs the analogue voltage control signal to control the voltage regulator circuit to generate a predetermined voltage for modulation by the H-bridge circuit connected to the microchip to drive the ultrasonic transducer in response to feedback signals which are indicative of the operation of the ultrasonic transducer; and
a hookah attachment arrangement which is configured to attach the hookah device to a hookah, the hookah attachment arrangement having a hookah outlet port which provides a fluid flow path from the mist outlet ports of the mist generator devices and out of the hookah device such that, when at least one of the mist generator devices is activated by the driver device, mist generated by each activated mist generator device flows along the fluid flow path and out of the hookah device to the hookah.

2. The hookah device of clause 1, wherein the microcontroller is configured to identify and control each mist generator device using a respective unique identifier for the mist generator device.

3. The hookah device of clause 1, wherein each mist generator device comprises:
an identification arrangement comprising:
  an integrated circuit having a memory which stores a unique identifier for the mist generator device; and
  an electrical connection which provides an electronic interface for communication with the integrated circuit.

4. The hookah device of clause 1, wherein the microcontroller is configured to control each microchip and each respective mist generator device to activate independently of the other mist generator devices.

5. The hookah device of clause 4, wherein the microcontroller is configured to control the mist generator devices to activate in a predetermined sequence.

6. The hookah device of clause 1, wherein the hookah device comprises:

a manifold having a manifold pipe which is in fluid communication with the mist outlet ports of the mist generator devices, wherein mist output from the mist outlet ports combines in the manifold pipe and flows through the manifold pipe and out from the hookah device.

7. The hookah device of clause 6, wherein the hookah device comprises four mist generator devices which are releasably coupled to the manifold at 90° relative to one another.

8. The hookah device of clause 1, wherein the feedback input terminal receives a feedback signal from the H-bridge circuit in the form of a voltage which indicative of an rms current of an AC drive signal which is driving the ultrasonic transducer.

9. The hookah device of clause 1, wherein each microchip further comprises:
   a temperature sensor which is embedded within the microchip, wherein the temperature sensor generates a temperature signal which is indicative of the temperature of the microchip, and wherein the temperature signal is received by a further ADC input terminal of the ADC subsystem and the temperature signal is sampled by the ADC.

10. The hookah device of clause 1, wherein the ADC subsystem samples signals received at the plurality of ADC input terminals sequentially with each signal being sampled by the ADC subsystem a respective predetermined number of times.

11. The hookah device of clause 1, wherein the device further comprises:
   a plurality of further microchips, wherein each further microchip of the plurality of further microchips is connected to a respective microchip of the plurality of microchips and comprises one H-bridge circuit of the plurality of H-bridge circuits, wherein each further microchip is a single unit which comprises a plurality of interconnected embedded components and subsystems comprising:
   a first power supply terminal; and
   a second power supply terminal, wherein
      the H-bridge circuit in the further microchip incorporates a first switch, a second switch, a third switch and a fourth switch, and wherein:
      the first switch and the third switch are connected in series between the first power supply terminal and the second power supply terminal;
      a first output terminal is connected electrically between the first switch and the third switch, wherein the first output terminal is connected to a first terminal of the ultrasonic transducer,
      the second switch and the fourth switch are connected in series between the first power supply terminal and the second power supply terminal, and
      a second output terminal is connected electrically between the second switch and the fourth switch, wherein the second output terminal is connected to a second terminal of the ultrasonic transducer;
   a first phase terminal which receives the first phase output signal from the pulse width modulation (PWM) signal generator subsystem;
   a second phase terminal which receives a second phase output signal from the PWM signal generator subsystem;
   a digital state machine which generates timing signals based on the first phase output signal and the second phase output signal and outputs the timing signals to the switches of the H-bridge circuit to control the switches to turn on and off in a sequence such that the H-bridge circuit outputs an AC drive signal for driving the ultrasonic transducer, wherein the sequence comprises a free-float period in which the first switch and the second switch are turned off and the third switch and the fourth switch are turned on in order to dissipate energy stored by the ultrasonic transducer;
   a current sensor which incorporates:
      a first current sense resistor which is connected in series between the first switch and the first power supply terminal;
      a first voltage sensor which measures the voltage drop across the first current sense resistor and provides a first voltage output which is indicative of the current flowing through the first current sense resistor;
      a second current sense resistor which is connected in series between the second switch and the first power supply terminal;
      a second voltage sensor which measures the voltage drop across the second current sensor resistor and provides a second voltage output which is indicative of the current flowing through the second current sense resistor; and
      a current sensor output terminal which provides an rms output voltage relative to ground which is equivalent to the first voltage output and the second voltage output,
   wherein the rms output voltage is indicative of an rms current flowing through the first switch or the second switch and the current flowing through the ultrasonic transducer which is connected between the first output terminal and the second output terminal.

12. The hookah device of clause 11, wherein the H-bridge circuit in each further microchip is configured to output a power of 22 W to 50 W to the ultrasonic transducer which is connected to the first output terminal and the second output terminal.

13. The hookah device of clause 11, wherein each further microchip comprises:
   a temperature sensor which is embedded within the further microchip, wherein the temperatures sensor measures the temperature of the further microchip and disables at least part of the further microchip in the event that the temperature sensor senses that the further microchip is at a temperature which is in excess of a predetermined threshold.

14. The hookah device of clause 11, wherein the device further comprises:
   a boost converter circuit which is configured to increase a power supply voltage to a boost voltage in response to the analogue voltage output signal from the DAC output terminal, wherein the boost converter circuit provides the boost voltage at the first power supply terminal such that the boost voltage is modulated by the switching of the switches of the H-bridge circuit.

15. The hookah device of clause 11, wherein the current sensor senses the current flowing through the resonant circuit during the free-float period and the digital state machine adapts the timing signals to switch on either the first switch or the second switch when the current sensor senses that the current flowing through the resonant circuit during the free-float period is zero.

16. The hookah device of clause 11, wherein, during a setup phase of operation of the device, the further microchip:

measures the length of time taken for the current flowing through the resonant circuit to fall to zero when the first switch and the second switch are turned off and the third switch and the fourth switch are turned on; and
sets the length of time of the free-float period to be equal to the measured length of time.

17. The hookah device of clause 1, wherein the device further comprises:
a memory storing instructions which, when executed by the microcontroller, cause the microchip to:
A. control the H-bridge circuit to output an AC drive signal to the ultrasonic transducer at a sweep frequency;
B. calculate the active power being used by the ultrasonic transducer based on the feedback signal;
C. control the H-bridge circuit to modulate the AC drive signal to maximise the active power being used by the ultrasonic transducer;
D. store a record in the memory of the maximum active power used by the ultrasonic transducer and the sweep frequency of the AC drive signal;
E. repeat steps A-D for a predetermined number of iterations with the sweep frequency incrementing or decrementing with each iteration such that, after the predetermined number of iterations has occurred, the sweep frequency has been incremented or decremented from a start sweep frequency to an end sweep frequency;
F. identify from the records stored in the memory the optimum frequency for the AC drive signal which is the sweep frequency of the AC drive signal at which a maximum active power is used by the ultrasonic transducer; and
G. control the H-bridge circuit to output an AC drive signal to the ultrasonic transducer at the optimum frequency to drive the ultrasonic transducer to atomise a liquid.

18. The hookah device of clause 17, wherein the start sweep frequency is 2900 kHz and the end sweep frequency is 3100 kHz.

19. A hookah comprising:
a water chamber;
an elongate stem having a first end which is attached to the water chamber, the stem comprising a mist flow path which extends from a second end of the stem, through the stem, to the first end; and
a hookah device comprising:
a plurality of ultrasonic mist generator devices, wherein each mist generator device incorporates:
a mist generator housing which is elongate and comprises an air inlet port and a mist outlet port;
a liquid chamber provided within the mist generator housing, the liquid chamber containing a liquid to be atomised;
a sonication chamber provided within the mist generator housing;
a capillary element extending between the liquid chamber and the sonication chamber such that a first portion of the capillary element is within the liquid chamber and a second portion of the capillary element is within the sonication chamber;
an ultrasonic transducer having an atomisation surface, wherein part of the second portion of the capillary element is superimposed on part of the atomisation surface, and wherein when the ultrasonic transducer is driven by an AC drive signal the atomisation surface vibrates to atomise the liquid carried by the second portion of the capillary element to generate a mist comprising the atomised liquid and air within the sonication chamber; and
an airflow arrangement which provides an air flow path between the air inlet port, the sonication chamber and the air outlet port, wherein the hookah device further comprises:
a plurality of H-bridge circuits, wherein each H-bridge circuit of the plurality of H-bridge circuits connects to a respective one of the ultrasonic transducers, wherein the H-bridge circuit generates an AC drive signal to drive the ultrasonic transducer;
a microcontroller;
a data bus which is connected electrically to the microcontroller to communicate data to and from the microcontroller;
a plurality of microchips which are connected electrically to the data bus to receive data from and transmit data to the microcontroller, wherein each microchip of the plurality of microchips connects connected to a respective one of the H-bridge circuits to control the H-bridge circuit to generate the AC drive signal, wherein each microchip is a single unit which comprises a plurality of interconnected embedded components and subsystems comprising:
an oscillator which generates:
a main clock signal,
a first phase clock signal which is high for a first time during the positive half-period of the main clock signal and low during the negative half-period of the main clock signal, and
a second phase clock signal which is high for a second time during the negative half-period of the main clock signal and low during the positive half-period of the main clock signal, wherein the phases of the first phase clock signal and the second phase clock signal are centre aligned;
a pulse width modulation (PWM) signal generator subsystem comprising:
a delay locked loop which generates a double frequency clock signal using the first phase clock signal and the second phase clock signal, the double frequency clock signal being double the frequency of the main clock signal, wherein the delay locked loop controls the rising edge of the first phase clock signal and the second phase clock signal to be synchronous with the rising edge of the double frequency clock signal, and wherein the delay locked loop adjusts the frequency and the duty cycle of the first phase clock signal and the second phase clock signal in response to a driver control signal to produce a first phase output signal and a second phase output signal, wherein the first phase output signal and the second phase output signal are configured to drive the H-bridge circuit connected to the microchip to generate an AC drive signal to drive the ultrasonic transducer; a first phase output signal terminal which outputs the first phase output signal to the H-bridge circuit connected to the microchip;
a second phase output signal terminal which outputs the second phase output signal to the H-bridge circuit connected to the microchip;
a feedback input terminal which receives a feedback signal from the H-bridge circuit, the feedback signal being indicative of a parameter of the operation of the H-bridge circuit connected to the microchip or AC drive signal when the H-bridge circuit is driving the ultrasonic transducer with the AC drive signal to atomise the liquid;

an analogue to digital converter (ADC) subsystem comprising:
a plurality of ADC input terminals which receive a plurality of respective analogue signals, wherein one ADC input terminal of the plurality of ADC input terminals is connected to the feedback input terminal such that the ADC subsystem receives the feedback signal from the H-bridge circuit connected to the microchip, and wherein the ADC subsystem samples analogue signals received at the plurality of ADC input terminals at a sampling frequency which is proportional to the frequency of the main clock signal and the ADC subsystem generates ADC digital signals using the sampled analogue signals;

a digital processor subsystem which receives the ADC digital signals from the ADC subsystem and processes the ADC digital signals to generate the driver control signal, wherein the digital processor subsystem communicates the driver control signal to the PWM signal generator subsystem to control the PWM signal generator subsystem; and a digital to analogue converter (DAC) subsystem comprising:
a digital to analogue converter (DAC) which converts a digital control signal generated by the digital processor subsystem into an analogue voltage control signal to control a voltage regulator circuit which generates a voltage for modulation by the H-bridge circuit connected to the microchip; and
a DAC output terminal which outputs the analogue voltage control signal to control the voltage regulator circuit to generate a predetermined voltage for modulation by the H-bridge circuit connected to the microchip to drive the ultrasonic transducer in response to feedback signals which are indicative of the operation of the ultrasonic transducer; and a hookah attachment arrangement which is attached to the stem of the hookah at the second end of the stem, the hookah attachment arrangement having a hookah outlet port which provides a fluid flow path from the mist outlet ports of the mist generator devices and out of the hookah device such that, when at least one of the mist generator devices is activated by the driver device, mist generated by each activated mist generator device flows along the fluid flow path and out of the hookah device to the hookah.

Although certain example embodiments of the invention have been described, the scope of the appended claims is not intended to be limited solely to these embodiments. The claims are to be construed literally, purposively, and/or to encompass equivalents.

The invention claimed is:

1. A hookah device for use with a hookah having an elongate stem and a water chamber with a first end of the stem attached to the water chamber, the hookah device comprising:
a plurality of ultrasonic mist generator devices which are each provided with a respective housing which comprises an air inlet port and a mist outlet port, a liquid chamber provided within the mist generator housing, the liquid chamber containing a liquid to be atomized, and a sonication chamber provided within the mist generator housing;
a driver device which is connected electrically to each of the plurality of mist generator devices, the driver device including a microcontroller configured to activate and control each of the plurality of the mist generator devices, wherein each mist generator device is releasably attached to the driver device so that each mist generator device is separable as an individual unit from the driver device; and
a hookah attachment arrangement which is configured to attach the hookah device to a second end of the stem of the hookah, the hookah attachment arrangement having a hookah outlet port which provides a fluid flow path from the mist outlet ports of the mist generator devices and out of the hookah device such that, when at least one of the mist generator devices is activated by the driver device, mist generated by each activated mist generator device flows along the fluid flow path and out of the hookah device to the hookah.

2. The hookah device of claim 1, wherein the driver device is configured to control the operation of the mist generator devices in response to data received from a computing device.

3. The hookah device of claim 2, wherein the computing device is a smartphone.

4. The hookah device of claim 3, wherein the smartphone comprises a companion mobile application.

5. The hookah device of claim 1, wherein the driver device is connected electrically to each of the mist generator devices by a data bus and the driver device is configured to identify and control each mist generator device using a respective unique identifier for the mist generator device.

6. The hookah device of claim 1, wherein each mist generator device comprises:
an identification arrangement comprising:
an integrated circuit having a memory which stores a unique identifier for the mist generator device; and
an electrical connection which provides an electronic interface for communication with the integrated circuit.

7. The hookah device of claim 1, wherein the microcontroller is configured to control each respective mist generator device to activate independently of the other mist generator devices.

8. The hookah device of claim 7, wherein the microcontroller is configured to control the mist generator devices to activate in a predetermined sequence.

9. The hookah device of claim 1, wherein the hookah device further comprises:
a manifold having a manifold pipe which is in fluid communication with the mist outlet ports of the mist generator devices, wherein mist output from the mist outlet ports combines in the manifold pipe and flows through the manifold pipe and out from the hookah device.

10. The hookah device of claim 9, wherein the hookah device further comprises four mist generator devices which are releasably coupled to the manifold at 90° relative to one another.

11. The hookah device of claim 1, wherein the driver device further comprises:
an AC driver which is configured to generate an AC drive signal at a predetermined frequency to drive a respective ultrasonic transducer in each mist generator device;

an active power monitoring arrangement which is configured to monitor the active power used by the ultrasonic transducer when the ultrasonic transducer is driven by the AC drive signal, wherein the active power monitoring arrangement is configured to provide a monitoring signal which is indicative of an active power used by the ultrasonic transducer;

a processor which is configured to control the AC driver and to receive the monitoring signal drive from the active power monitoring arrangement; and a memory storing instructions which, when executed by the processor, cause the processor to:
  A. control the AC driver to output an AC drive signal to the ultrasonic transducer at a predetermined sweep frequency;
  B. calculate the active power being used by the ultrasonic transducer based on the monitoring signal;
  C. control the AC driver to modulate the AC drive signal to maximize the active power being used by the ultrasonic transducer;
  D. store a record in the memory of the maximum active power used by the ultrasonic transducer and the sweep frequency of the AC drive signal;
  E. repeat steps A-D for a predetermined number of iterations with the sweep frequency incrementing with each iteration such that, after the predetermined number of iterations has occurred, the sweep frequency has been incremented from a start sweep frequency to an end sweep frequency;
  F. identify from the records stored in the memory the optimum frequency for the AC drive signal which is the sweep frequency of the AC drive signal at which a maximum active power is used by the ultrasonic transducer; and
  G. control the AC driver to output an AC drive signal to the ultrasonic transducer at the optimum frequency to drive the ultrasonic transducer to atomize a liquid.

12. The hookah device of claim 11, wherein the active power monitoring arrangement comprises:
  a current sensing arrangement which is configured to sense a drive current of the AC drive signal driving the ultrasonic transducer, wherein the active power monitoring arrangement is configured to provide a monitoring signal which is indicative of the sensed drive current.

13. The hookah device of claim 11, wherein the memory stores instructions which, when executed by the processor, cause the processor to:
  repeat steps A-D with the sweep frequency being incremented from a start sweep frequency of 2900 kHz to an end sweep frequency of 2960 KHz.

14. The hookah device of claim 11, wherein the memory stores instructions which, when executed by the processor, cause the processor to:
  repeat steps A-D with the sweep frequency being incremented from a start sweep frequency of 2900 kHz to an end sweep frequency of 3100 KHz.

15. The hookah device of claim 11, wherein the AC driver is configured to modulate the AC drive signal by pulse width modulation to maximize the active power being used by the ultrasonic transducer.

16. A hookah device for use with a hookah having an elongate stem and a water chamber with a first end of the stem attached to the water chamber, the hookah device comprising:

a plurality of ultrasonic mist generator devices which are each provided with a respective mist outlet port;

a driver device which is connected electrically to each of the mist generator devices and configured to activate the mist generator devices; and a hookah attachment arrangement which is configured to attach the hookah device to a second end of the stem of the hookah, the hookah attachment arrangement having a hookah outlet port which provides a fluid flow path from the mist outlet ports of the mist generator devices and out of the hookah device such that, when at least one of the mist generator devices is activated by the driver device, mist generated by each activated mist generator device flows along the fluid flow path and out of the hookah device to the hookah, wherein each mist generator device comprises:

a mist generator housing which is elongate and comprises an air inlet port and the said mist outlet port;

a liquid chamber provided within the mist generator housing, the liquid chamber containing a liquid to be atomized;

a sonication chamber provided within the mist generator housing;

a capillary element extending between the liquid chamber and the sonication chamber such that a first portion of the capillary element is within the liquid chamber and a second portion of the capillary element is within the sonication chamber;

an ultrasonic transducer having a generally planar atomization surface which is provided within the sonication chamber, the ultrasonic transducer being mounted within the mist generator housing such that the plane of the atomization surface is substantially parallel with a longitudinal length of the mist generator housing, wherein part of the second portion of the capillary element is superimposed on part of the atomization surface, and wherein the ultrasonic transducer is configured to vibrate the atomization surface to atomize a liquid carried by the second portion of the capillary element to generate a mist comprising the atomized liquid and air within the sonication chamber; and an airflow arrangement which provides an air flow path between the air inlet port, the sonication chamber and the air outlet port.

17. The hookah device of claim 16, wherein each mist generator device further comprises:
  a transducer holder which is held within the mist generator housing, wherein the transducer holder holds the ultrasonic transducer and retains the second portion of the capillary element superimposed on part of the atomization surface; and
  a divider portion which provides a barrier between the liquid chamber and the sonication chamber, wherein the divider portion comprises a capillary aperture through which part of the first portion of the capillary element extends.

18. The hookah device of claim 16, wherein the capillary element is 100% bamboo fiber.

19. The hookah device of claim 16, wherein the airflow arrangement is configured to change the direction of a flow of air along the air flow path such that the flow of air is substantially perpendicular to the atomization surface of the ultrasonic transducer as the flow of air passes into the sonication chamber.

20. The hookah device of claim 16, wherein the liquid chamber contains a liquid having a liquid viscosity between 1.05 Pa·s and 1.412 Pa·s and a liquid density between 1.1 g/ml and 1.3 g/ml.

21. The hookah device of claim 16, wherein the liquid chamber contains a liquid comprising approximately a 2:1 molar ratio of levulinic acid to nicotine.

22. A hookah comprising:
a water chamber;
an elongate stem having a first end which is attached to the water chamber, the stem comprising a mist flow path which extends from a second end of the stem, through the stem, to the first end; and
a hookah device attached to the stem of the hookah at the second end of the stem, the hookah device comprising:
a plurality of ultrasonic mist generator devices which are each provided with a respective housing which comprises an air inlet port and a mist outlet port, a liquid chamber provided within the mist generator housing, the liquid chamber containing a liquid to be atomized, and a sonication chamber provided within the mist generator housing;
a driver device which is connected electrically to each of plurality of the mist generator devices and configured to activate the mist generator devices, wherein each mist generator device is releasably attached to the driver device so that each mist generator device is separable as an individual unit from the driver device; and
a hookah attachment arrangement which is configured to attach the hookah device to a second end of the stem of the hookah, the hookah attachment arrangement having a hookah outlet port which provides a fluid flow path from the mist outlet ports of the mist generator devices and out of the hookah device such that, when at least one of the mist generator devices is activated by the driver device, mist generated by each activated mist generator device flows along the fluid flow path and out of the hookah device to the hookah.

23. A system comprising:
a plurality of hookah devices, each hookah device being a hookah device comprising:
a plurality of ultrasonic mist generator devices which are each provided with a respective housing which comprises an air inlet port and a mist outlet port, a liquid chamber provided within the mist generator housing, the liquid chamber containing a liquid to be atomized, and a sonication chamber provided within the mist generator housing;
a driver device which is connected electrically to each of the plurality of mist generator devices and configured to activate the mist generator devices, wherein each mist generator device is releasably attached to the driver device so that each mist generator device is separable as an individual unit from the driver device; and
a hookah attachment arrangement which is configured to attach the hookah device to a second end of the stem of the hookah, the hookah attachment arrangement having a hookah outlet port which provides a fluid flow path from the mist outlet ports of the mist generator devices and out of the hookah device such that, when at least one of the mist generator devices is activated by the driver device, mist generated by each activated mist generator device flows along the fluid flow path and out of the hookah device to the hookah; and
a computing device being configured to communicate wirelessly with each hookah device such that the computing device can control the operation of the plurality of hookah devices.

24. A hookah device for use with a hookah having an elongate stem and a water chamber with a first end of the stem attached to the water chamber, the hookah device comprising:
a plurality of ultrasonic mist generator devices which are each provided with a respective mist outlet port;
a driver device which is connected electrically to each of the mist generator devices and configured to activate the mist generator devices, wherein each mist generator device is releasably attached to the driver device so that each mist generator device is separable from the driver device; and
a hookah attachment arrangement which is configured to attach the hookah device to a second end of the stem of the hookah, the hookah attachment arrangement having a hookah outlet port which provides a fluid flow path from the mist outlet ports of the mist generator devices and out of the hookah device such that, when at least one of the mist generator devices is activated by the driver device, mist generated by each activated mist generator device flows along the fluid flow path and out of the hookah device to the hookah, wherein each mist generator device comprises:
an identification arrangement comprising:
an integrated circuit having a memory which stores a unique identifier for the mist generator device; and
an electrical connection which provides an electronic interface for communication with the integrated circuit.

* * * * *